US008637293B2

(12) United States Patent
Adney et al.

(10) Patent No.: US 8,637,293 B2
(45) Date of Patent: Jan. 28, 2014

(54) CELLOBIOHYDROLASE I ENZYMES

(75) Inventors: William S. Adney, Golden, CO (US); Michael E. Himmel, Littleton, CO (US); Stephen R. Decker, Berthoud, CO (US); Eric P. Knoshaug, Golden, CO (US); Mark R. Nimlos, Golden, CO (US); Michael F. Crowley, Lakewood, CO (US); Tina Jeoh, Davis, CA (US)

(73) Assignee: Alliance for Sustainable Energy, LLC, Golden, CO (US)

(*) Notice: Subject to any disclaimer, the term of this patent is extended or adjusted under 35 U.S.C. 154(b) by 0 days.

(21) Appl. No.: 12/123,352

(22) Filed: May 19, 2008

(65) Prior Publication Data

US 2009/0162916 A1 Jun. 25, 2009

Related U.S. Application Data

(63) Continuation-in-part of application No. 10/031,496, filed on Jan. 14, 2002, now Pat. No. 7,375,197, which is a continuation of application No. PCT/US00/19007, filed on Jul. 13, 2000.

(60) Provisional application No. 60/143,711, filed on Jul. 13, 1999.

(51) Int. Cl.
| C12N 9/26 | (2006.01) |
| C12N 1/20 | (2006.01) |
| C12N 15/00 | (2006.01) |
| C12P 21/06 | (2006.01) |
| C12P 21/04 | (2006.01) |
| C12Q 1/00 | (2006.01) |
| C12Q 1/68 | (2006.01) |
| C07H 21/04 | (2006.01) |

(52) U.S. Cl.
USPC ......... 435/201; 435/440; 435/69.1; 435/71.1; 435/252.3; 435/320.1; 435/6.1; 435/4; 536/23.2

(58) Field of Classification Search
USPC .................................. 435/201, 440; 536/23.2
See application file for complete search history.

(56) References Cited

U.S. PATENT DOCUMENTS

| 4,472,504 | A | 9/1984 | Gallo |
| 5,298,405 | A | 3/1994 | Nevalainen et al. |
| 5,874,276 | A | 2/1999 | Fowler et al. |
| 5,989,870 | A | 11/1999 | Nakari et al. |
| 6,011,147 | A | 1/2000 | Nakari et al. |
| 6,114,296 | A | 9/2000 | Schulein et al. |
| 7,375,197 | B2 | 5/2008 | Adney et al. |

FOREIGN PATENT DOCUMENTS

| EP | 0133035 | 2/1985 |
| EP | 0137280 | 4/1985 |
| WO | 94/04673 | 3/1994 |
| WO | 01/04284 | 1/2001 |

OTHER PUBLICATIONS

Boer et al. Characterization of Trichoderma reesei cellobiohydrolase Cel7A secreted from Pichia pastoris using two different promoters. Biotechnol Bioeng. Sep. 5, 2000;69(5):486-94.*
Receveur et al. Dimension, shape, and conformational flexibility of a two domain fungal cellulase in solution probed by small angle X-ray scattering. J Biol Chem. Oct. 25, 2002;277(43):40887-92. Epub Aug. 16, 2002.*
Harrison et al. Modified glycosylation of cellobiohydrolase I from a high cellulase-producing mutant strain of Trichoderma reesei. Eur J Biochem. Aug. 15, 1998;256(1):119-27.*
Branden et al. Introduction to Protein Structure, Garland Publishing Inc., New York, p. 247, 1991.*
Chen et al. Substitution of asparagine residues in Aspergillus awamori glucoamylase by site-directed mutagenesis to eliminate N-glycosylation and inactivation by deamidation. Biochem J. Jul. 1, 1994;301 ( Pt 1):275-81.*
Michener et al. Characterization of Glycosylation Sites of a Recombinant and Native Penicillium funiculosum Family 7 Celllobiohydrolase. 27th Symposium on Biotechnology for Fuels and Chemicals held in Denver, CO May 1-4, 2005.*
Adney et al. Probing the role of N-linked glycans in the stability and activity of fungal cellobiohydrolases by mutational analysis. Cellulose. vol. 16, No. 4, 699-709, 2009.*
Basco, et al., "Selective elongation of the oligosaccharide attached to the second potential glycosylation site of yeast exoglucanase: effects of the activity and properties of the enzyme", Biochemical Journal, Dec. 15, 1994, vol. 304, No. 3, pp. 917-922, Portland Press, London.
Boer, et al., "Characterization of Trichoderma reesei cellobiohydrolase Cel7A secreted from Pichia pastoris using two different promoters", Biotechnology Bioengineering, Sep. 5, 2000, vol. 69, No. 5, pp. 486-494.
Branden, et al., "Introduction to Protein Structure", Garland Publishing Inc., 1991, p. 247, New York.
Godbole, et al., "Cloning and Expression of Trichoderma reesei Cellobiohydrase I in Pichia pastoris", Biotechnology progress, 1999, vol. 15, pp. 828-833.

(Continued)

Primary Examiner — Yong Pak
(74) Attorney, Agent, or Firm — John C. Stolpa; Paul J. White

(57) ABSTRACT

Provided herein is an isolated Cel7A polypeptide comprising mutations in the catalytic domain of the polypeptide relative to the catalytic domain of a wild type Cel7A polypeptide, wherein the mutations reduce N-linked glycosylation of the isolated polypeptide relative to the wild type polypeptide. Also provided herein is an isolated Cel7A polypeptide comprising increased O-linked glycosylation of the linker domain relative to a linker domain of a wild type Cel7A polypeptide. The increased O-linked glycosylation is a result of the addition of and/or substitution of one or more serine and/or threonine residues to the linker domain relative to the linker domain of the wild type polypeptide. In some embodiments, the isolated Cel7A polypeptide comprising mutations in the catalytic domain of the polypeptide relative to the catalytic domain of a wild type Cel7A polypeptide further comprises increased O-linked glycosylation of the linker domain relative to a linker domain of a wild type Cel7A polypeptide. The mutations in the catalytic domain reduce N-linked glycosylation of the isolated polypeptide relative to the wild type polypeptide. The addition of and/or substitution of one or more serine and/or threonine residues to the linker domain relative to the linker domain of the wild type polypeptide increases O-linked glycosylation of the isolated polypeptide. Further provided are compositions comprising such polypeptides and nucleic acids encoding such polypeptides. Still further provided are methods for making such polypeptides.

16 Claims, 19 Drawing Sheets

(56) References Cited

OTHER PUBLICATIONS

Harrison, et al., "Modified glycosylation of cellobiohydrolase I from a high cellulase-poducing mutant strain of Trichoderma reesei", European journal of biochemistry / FEBS, Aug. 15, 1998, vol. 256, No. 1, pp. 119-127.

Maras, et al., "In vitro conversion of the carbohydrate moiety of fungal glycoproteins to mammalian-type oligosaccharides, "European Journal of Biochemistry, 1997, vol. 249, pp. 701-707, Berlin.

Receveur, et al., "Dimension, shape, and confomrational flexibility of a two domain fungal cellulase in solution probed by small angle X-ray scattering", Journal of Biological Chemistry, Oct. 25, 2002, vol. 277, No. 43, pp. 40887-40892.

Srisodsuk, et al., "Role of the Interdomain Linker Peptide of Trichoderma reesei Cellobiohydrolase I in Its Interaction with Crystalline Cellulose",The Journal of biological chemistry, 1993, vol. 268, No. 28, pp. 20756-20761.

"N- and O-linked Protein Glycosylation", Ionsource website, accessed by inventors Apr. 21, 2008, available at http://www.ionsource.com/Card/carbo/nolink.htm, printed on Dec. 21, 2009, pp. 1-3.

Anumula, "High sensitivity and high resolution methods for glycoprotein analysis", Glycobiology, 2000, vol. 10, Abstract 225, p. 1138.

Armand, et al., "A bifunctionalized flourogenictetrasachardie as a substrate to study cellulases", Journal of Biological Chemistry, 1997, vol. 272, No. 5, p. 2709-2713.

Boer, et al., "The relationship between thermal stability and pH optimum studied with wild-type and mutant Trichoderma reesei cellobiohydrolase Cel7A", European Journal of Biochemistry, Mar. 2003, vol. 270, No. 5, pp. 841-848.

Breyer, et al., "A structural basis for processivity", Protein Science, Sep. 2001, vol. 10, No. 9, pp. 1699-1711.

Cartee, et al., "The type 3 synthase from Streptococcus pneumoniae is a processive enzyme that synthesizes type 3 polysaccharide from the non-reducing end", Glycobiology, 1998, vol. 8, No. 11, Abstract 74, p. 1123.

Chen, et al., "Toward Improved Cellulases—Targeted Modifications of Trichoderma-Reesei Exocellobiohydrolasei using Site Specific Mutagenesis", Abstracts of Papers of the American Chemical Society, 1987, vol. 194, 188-MBTD.

Chen, et al., "3 Forms of Cellobiohydrolase-1 from Trichoderma-Reesei", Biochemistry and Molecular Biology International, Aug. 1993, vol. 30, No. 5, pp. 901-910.

Chen, et al., "Effect of replacing helical glycine residues with alanines on reversible and irreversible stability and production of Aspergillus awamori glucoamylase", Protein Engineering, 1996, vol. 9, pp. 499-505.

Chou, et al., "Kinetics of Processive Nucleic-Acid Polymerases and Nucleases", Analytical Biochemistry, Sep. 1994, vol. 221, No. 2, pp. 217-230.

Cui, et al., "Aspects of the use of complex media for submerged fermentation of Aspergillus awamori", Enzyme and Microbial Technology, Jul.-Aug. 1998, vol. 23, pp. 168-177.

Cui, et al., "Effect of agitation intensities on fungal morphology of submerged fermentation", Biotechnology and Bioengineering, Sep. 5, 1997, vol. 55, No. 5, pp. 715-726.

Cui, et al., "Effects of dissolved oxygen tension and mechanical forces on fungal morphology in submerged fermentation", Biotechnology and Bioengineering, Feb. 20, 1998, vol. 57, No. 4, pp. 409-419.

Cui, et al., "Influence of fermentation conditions and scale on the submerged fermentation of Aspergillus awamori", Enzyme and Microbial Technology, Jul.-Aug. 1998, vol. 23, pp. 157-167.

Cui, et al., "Modeling and Measurements of Fungal Growth and Morphology in Submerged Fermentations", Biotechnology and Bioengineering, Oct. 28, 1998, vol. 60, No. 2, pp. 216-229.

Decker, et al., "Automated filter paper assay for determination of cellulase activity", Applied Biochemistry and Biotechnology, Spring 2003, vol. 105, pp. 689-703.

Degroot, et al., "Agrobacterium tumefaciens-mediated transformation of filamentous fungi", Nature biotechnology, Sep. 1998, vol. 16, No. 9, pp. 839-842.

Dell, et al., "Glycoprotein Structure Determination by Mass Spectrometry", Science, Mar. 23, 20012001, vol. 291, No. 5512, pp. 2351-2356.

Elshafei, et al., "The saccharification of corn stover by cellulase from Penicillium funiculosum", Bioresource Technology, 1991, vol. 35, No. 1, pp. 73-80.

Eriksen, et al., "Effect of N-Linked glycosylation on secretion, activity, and stability of alpha-amylase from Aspergillus oryzae", Current Microbiology, Aug. 1998, vol. 37, No. 2, pp. 117-122.

Eriksson, et al., "Heterogeneity of homologously expressed Hypocrea jecorina (Trichoderma reesei) Cel7B catalytic module", European Journal of Biochemistry, Apr. 2004, vol. 271, No. 7, pp. 1266-1276.

Fägerstam, et al., "The Primary Structure of a 1,4-Beta-Glucon Cellobiohydrolase from the fungus Thrichodermareesei QM-9414", FEBS Letters, 1984, vol. 167, 309-315.

Fang, et al., "Protein engineering of Aspergillus awamori glucoamylase to increase its pH optimum", Protein Engineering, May 1998, vol. 11, No. 5, pp. 383-388.

Foreman, et al., "Transcriptional regulation of biomass-degrading enzymes in the filamentous fungus Trichoderma reesei", Journal of Biological Chemistry, Aug. 22, 2003, vol. 278, No. 34, pp. 31988-31997.

Gaur, et al., "Cellulase activity at different sites in two fungal species, Trichoderma harziamum and Penicillium funiculosum", Acta bontanica Indica, 1990, vol. 18, No. 1, pp. 141-143.

Goto, et al., "Expression and functional analysis of a hyperglycosylated glucoamylase in a parental host, Aspergillus awamori var. kawachi", Applied and Environmental Microbiology, Jul. 1997, vol. 63, No. 7, pp. 2940-2943.

Gouka, et al, "Glucoamylase gene fusions alleviate limitations for protein production in Aspergillus awamori at the transcriptional and (post)translational levels", Applied and Environmental Microbiology, Feb. 1997, vol. 63, No. 2, pp. 488-497.

Gouka, et al., "An expression system based on the promoter region of the Aspergillus awamori 1, 4-beta-endoxylanase a gene", Applied Microbiology and Biotechnology, 1996, vol. 46, No. 1, pp. 28-35.

Gouka, et al., "Analysis of heterologous protein in defined recombinant Aspergillus awamori strains", Applied and Environmental Microbiology, 1996, vol. 62, No. 6, pp. 1951-1957.

Gouka, et al., "Kinetics of mRNA and protein synthesis of genes controlled by the 1, 4-beta-endoxylanase A Promoter in controlled fermentations of Aspergillus awamori", Applied and Environmental Microbiology, Oct. 1996, Vo. 62, No. 10, pp. 3646-3649.

Haltiwanger, et al., "Role of glycosylation indevelopment", Annual Review of Biochemistry, 2004, vol. 73, pp. 491-537.

Helbert, et al., "Fluorescent cellulose microfibris as substrate for the detection of cellulase activity", Biomacromolecules, May-Jun. 2003, vol. 4, No. 3, pp. 481-487.

Hellendoorn, et al., "Intrinsic kinetic parameters of the pellet forming fungus Aspergillus awamori", Biotechnology and Bioengineering, Jun. 5, 1998, vol. 58, No. 5, pp. 478-485.

Henrissat, et al., "Structural and sequence-based classifications of glycoside hydrolases", Current Opinion in Structural Biology, Oct. 1997, vol. 7, No. 5, pp. 637-644.

Hestrin, "Synthesis of cellulose by Acetobacter xylinum. II. Preparation of freeze-dried cells capable of polymerizing glucose to cellulose", The Biochemical Journal, 1954, vol. 58, pp. 345-352.

Hijarrubia, et al., "Characterization of the bip gene of Aspergillus awamori encoding a protein with an HDEL retention signal homologous to the mammalian BiP involved in polypeptide secretion", Current Genetics, Aug. 1997, vol. 32, No. 2, pp. 139-146.

Himmel, et al., "Cellulase for commodity products from cellulosic biomass", Current Opinion in Biotechnology, Aug. 1999, vol. 10, No. 4, pp. 358-364.

Hui, et al., "Characterization of cellobiohydrates I (Cel7A) glycoforms from extracts of Trichoderma reesei using capillary isoelectric focusing and elctrospray mass spectrometry", Journal of Chromatography B-Analytical Technologies in the Biomedical and Life Sciences, 2001, vol. 752, No. 2, pp. 349-368.

(56) References Cited

OTHER PUBLICATIONS

Jacobson, et al., "Structure of a stabilizing disulfide bridge mutant that closes the active-site cleft of T4 lysozyme", Protein science : A publication of the Protein Society, 1992, vol. 1, pp. 46-57.

Johansen, et al., "Influence on product formation in Aspergillus awamori durging submerged fermentations", Biotechnology Progress, Mar.-Apr. 1998, vol. 14, No. 2, pp. 233-240.

Krystynowicz, et al., "Factors affecting the yield and properties of bacterial cellulose", Journal of Industrial Microbiology & Biotechnology, Oct. 2002, vol. 29, No. 4, pp. 189-195.

Lachke, et al., "Strain selection criteria for Penicillium funiculosum in enzymic hydrolysis of lignocellulosics", Biotechnology Letters, 1987, vol. 9, No. 2, pp. 147-150.

Lassig, et al., "Inhibition of cellobiohydrolase I from Trichoderma reesei by palladium", Archives of Biochemistry and Biophysics, Sep. 10, 1995, vol. 322, No. 1, pp. 119-126.

Laymon, et al., "Cloning and expression of full-length Trichoderma reesei cellobiohydrolase I cDNAs in *Escherichia coli*.", Applied Biochemistry and Biotechnology, Spring 1996, vols. 57/58, pp. 389-397.

Li, et al., "Effect of introducing proline residues on the stability of Aspergillus awamori", Protein Engineering, Oct. 1997, vol. 10, No. 10, pp. 1199-1204.

Li, et al., "Effect on thermostability and catalytic activity of introducing disulfide bonds into Aspergillus awamori glucoamylase", Protein Engineering, Aug. 1998, vol. 11, No. 89, pp. 661-667.

Manchanda, et al., "Studies on fermentation-broth rheology of a Penicillium strain with cellulose as substrate Enzymic conversion of cellulosic wastes into alcohol, Penicillium funiculosum", Journal of Chemical Technology and Biotechnology, 1982, vol. 32, No. 6, pp. 660-665.

"Maras, et al., "Structural characterization of N-linked oligosaccharides from cellobiohydrolase !secreted by the filamentous fungus Trichoderma reesei RUTC 30", European journal of biochemistry / FEBS, 1997, vol. 245, pp. 617-625".

Mcauley, et al., "Structure of a feruloyl esterase from Aspergillus niger", Acta Crystallographica Section D-Biological Crystallography, May 2004, vol. 60, Part 5, pp. 878-887.

Medve, et al., "Ion-exchange chromatrographic purification and quantitative analysis of Trichoderma reesei cellulases cellobiohydrolase, I II, and endoglucanase II by fast protein liquid chromatography", Journal of Chromatography A, 1998, vol. 808, Nos. 1-2, pp. 153-165.

Medve, et al., "Adsorption and synergism of cellobiohydrolase I and II of Trichoderma reesei during hydrolysis of microcrystalline cellulose", Biotechnology and Bioengineering, Nov. 5, 1994, vol. 44, No. 9, pp. 1064-1073.

Motoshima, et al., "Analysis of the stabilization of hen lysozyme by helix macrodipole and charged side chain interaction", Journal of Biochemistry (Tokyo), 1997, vol. 121, pp. 1076-1081.

Nascimento, et al., "Extracellular proteolytic processing of Aspergillus awamori GAI and GAII is supported by physico-chemical evidence", Applied Biochemistry and Biotechnology, Spring 1998, vols. 70-72, pp. 641-650.

Nicholson, et al., "Analysis of the interaction between charged side chains and the alpha- hellix dipole using designed thermostable mutants of phage T4 lysozyme", Biochemistry, 1991, vol. 30, pp. 9816-9828.

Okada, et al., "Efficient secretion of Trichoderma reesei cellobiohydrolase II in Schizosaccharomyces pombe and characterization of its products", 1998, vol. 49, pp. 301-308.

Penttilä, et al., "Efficient secretion of two fungal cellobiohydrolases by Saccharomyces cerevisiae", Gene, 1988, vol. 63, pp. 103-112.

Pjura, "Structure of a thermostable disulfide-bridge mutant of page T4 lysozyme shows that an engineered cross-link in a flexible region does not increase the rigidity of the folded protein", Biochemistry, 1990, vol. 29, pp. 2592-2598.

Presta, "Helix signals in proteins", Science, 1988, vol. 240, pp. 1632-1641.

Reinikainen, et al., "Investigation of the Function of Mutated Cellulose-Binding Domains of Trichoderma reesei Cellbiohydrolase I", Proteins, Structure Function Genetics, 1992, vol. 14, pp. 475-482.

Reverbel-Leroy, et al., "The Processive endocellulase Ce1F, a major component of the Clostridium cellulolyticum cellulosome: Purification and characterization of the recombinant form", Journal of Bacteriology, Jan. 1997, vol. 179, No. 1, pp. 46-52.

Richardson, et al., "Amino acid preferences for specific locations at the ends of alpha helices", Science, 1988, vol. 240, pp. 1648-1652.

Rowan, et al., "Catalytic macromolecular rotaxanes: Towards mimicking nature's processive catalysts", Abstracts of Papers of the American Chemical Society, 2003, vol. 225, pp. U637-U638, abstract 608.

Russell, "The crystal structure of citrate synthase from the thermophilic Archaeon, Thermoplasma acidophilum", Structure, Dec. 15, 1994, vol. 2, pp. 1157-1167.

Sahasrabudhe, et al., "Cloning of the Cellulase Gene from Penicillium-Funiculosum and Its Expression in *Escherichia-Coli*", FEMS Microbiology Letters, Jan. 1, 1990, vol. 54, Nos. 1-3, pp. 291-293.

Sakon, et al., "Crystal structures of thermostable family 5 endocellulase El from Acidothermus cellulolyticus in complex with cellotetraose", Biochemistry, 1996, vol. 35, pp. 10648-10660.

Siedenberg, et al., "Production of xylanase by Aspergillus awamori on synthetic medium in shake flask cultures", Process Biochemistry, Mar. 1998, vol. 33, No. 4, pp. 429-433.

Sreerama, et al., "Estimation of protein secondary structure from circular dichroism spectra: Inclusion of denatured proteins with native proteins in the analysis", Analytical Biochemistry, Dec. 15, 2000, vol. 287, No. 2, pp. 243-251.

Stites, et al., "Evidence for strained interactions between side-chains and the polypeptide backbone", Journal of Molecular Biology, 1994, vol. 235, pp. 27-32.

Van Arsdell, et al., "Cloning, Characterization and Expression in Saccharoyces cerevisiae of Endoglucanase I from Trichoderma reesei", BiolTechnology, 1987, vol. 5, pp. 60-64, Nature Publishing Company.

Van Gemeren, et al., "The effect of pre- and pro-sequences and multicopy integration on heterologous expression of the Fusarium solani pisi cutinase gene in Asoergillus awamori", Applied Microbiology and Biotechnology, Jul. 1996, vol. 45, No. 6, pp. 755-763.

Van Gemeren, et al., "The ER chaperone encoding bipA gene of black Aspergilli is induced by heat shock and unfolded proteins", Gene, Oct. 1, 1997, vol. 198, Nos. 1-2 pp. 43-52.

Van Gemeren, et al., "Expression and secretion of defined cutinase variants by Aspergillus awamori", Applied and Environmental Microbiology, Aug. 1998, vol. 64, No. 8, pp. 2794-2799.

Von Ossowski, et al., "Expression of a Fungal Cellobiohydrolase in Insect Cells", Biochemical and Biophysical Research Communications, 1997, vol. 233, pp. 25-29.

Von Ossowski, et al., "Engineering the exo-loop of Trichoderma reesei cellobiohydrolase, Cel7A. A comparison with Phanerochaete chrysosporium Ce17D", Journal of Molecular Biology, Oct. 31, 2003, vol. 333, No. 4, pp. 817-829.

Van Pouderoyen, et al., "Structural insights into the processivity of endopolygalacturonase I from Aspergillus niger", Febs Letters, Nov. 20, 2003, vol. 554, No. 3, pp. 462-466.

Varrot, et al., "Structural changes of the active site tunnel of Humicola insolens cellobiohydrolase, Cel6A, Upon oligosaccharide binding", Biochemistry, Jul. 13, 1999, vol. 38, No. 28, pp. 8884-8891.

Yan, et al., "Circular dichroism studies in conformation of cellobiohydrolase and endoglucanase from Trichoderma

(56) References Cited

OTHER PUBLICATIONS pseudokiningii S-38: effects of pH and ligand binding", Journal of Protein Chemistry, 1997, vol. 16, pp. 107-111.

Zurbriggen, et al., "Pilot scale production of a heterologous Trichoderma reesei cellulase by Saccharomyces cerevisiae", Journal of Biotechnology, 1990, vol. 13, No. 4, pp. 267-278.

European Search Report issued for European Application No. 00948637.4, dated Feb. 2, 2004.

International Preliminary Examination Report issued for International (PCT) Application No. PCT/US2000/019007, mailed Oct. 26, 2001.

International Search Report issued for International (PCT) Application No. PCT/US2000/019007, mailed Oct. 19, 2000.

* cited by examiner

FIGURE 1

Coding sequence of the *cbh 1* gene (SEQ ID NO: 4). Lower case letters represent the signal sequence, upper case letters the catalytic domain, bolded italics the linker region, and upper case underlined the cellulose-binding domain.

atgtatcggaagttggccgtcatctcggccttcttggccacagctcgtgctCAGTCGGCCTGCACTCTCCAAT
CGGA
GACTCACCCGCCTCTGACATGGCAGAAATGCTCGTCTGGTGGCACGTGCACT
CAACA
GACAGGCTCCGTGGTCATCGACGCCAACTGGCGCTGGACTCACGCTACGAAC
AGCAGCACGAACTGCTACGATGGCAACACTTGGAGCTCGACCCTATGTCCTG
ACAACGAGACCTGCGCGAAGAACTGCTGTCTGGACGGTGCCGCCTACGCGTC
CACGTACGGAGTTACCACGAGCGGTAACAGCCTCTCCATTGGCTTTGTCACCC
AGTCTGCGCAGAAGAACGTTGGCGCTCGCCTTTACCTTATGGCGAGCGACAC
GACCTACCAGGAATTCACCCTGCTTGGCAACGAGTTCTCTTTCGATGTTGATG
TTTCGCAGCTGCCGTGCGGCTTGAACGGAGCTCTCTACTTCGTGTCCATGGAC
GCGGATGGTGGCGTGAGCAAGTATCCCACCAACACCGCTGGCGCCAAGTACG
GCACGGGGTACTGTGACAGCCAGTGTCCCCGCGATCTGAAGTTCATCAATGG
CCAGGCCAACGTTGAGGGCTGGGAGCCGTCATCCAACAACGCGAACACGGG
CATTGGAGGACACGGAAGCTGCTGCTCTGAGATGGATATCTGGGAGGCCAAC
TCCATCTCCGAGGCTCTTACCCCCCACCCTTGCACGACTGTCGGCCAGGAGAT
CTGCGAGGGTGATGGGTGCGGCGGAACTTACTCCGATAACAGATATGGCGGC
ACTTGCGATCCCGATGGCTGCGACTGGAACCCATACCGCCTGGGCAACACCA
GCTTCTACGGCCCTGGCTCAAGCTTTACCCTCGATACCACCAAGAAATTGACC
GTTGTCACCCAGTTCGAGACGTCGGGTGCCATCAACCGATACTATGTCCAGA
ATGGCGTCACTTTCCAGCAGCCCAACGCCGAGCTTGGTAGTTACTCTGGCAA
CGAGCTCAACGATGATTACTGCACAGCTGAGGAGGCAGAATTCGGCGGATCC
TCTTTCTCAGACAAGGGCGGCCTGACTCAGTTCAAGAAGGCTACCTCTGGCG
GCATGGTTCTGGTCATGAGTCTGTGGGATGATTACTACGCCAACATGCTGTGG
CTGGACTCCACCTACCCGACAAACGAGACCTCCTCCACACCCGGTGCCGTGC
GCGGAAGCTGCTCCACCAGCTCCGGTGTCCCTGCTCAGGTCGAATCTCAGTCT
CCCAACGCCAAGGTCACCTTCTCCAACATCAAGTTCGGACCCATTGGCAGCA
CCGGCAACCCTAGCGGCGGCAAC***CCTCCCGGCGGAAACCCGCCTGGCACCAC
CACCACCCGCCGCCCAGCCACTACCACTGGAAGCTCTCCCGGACCT***<u>ACCCAGT
CTCACTACGGCCAGTGCGGCGGTATTGGCTACAGCGGCCCCACGGTCTGCGC
CAGCGGCACAACTTGCCAGGTCCTGAACCCTTACTACTCTCAGTGCCTGTAAA
GCTCC</u>

SDS-PAGE western blot using anti-CBH I showing the reduction in molecular weight of rCBH I expression clones as a function of the introduction of N>A modifications.

Plasmid map of fungal expression vector pPFE2/CBHI

Nucleotide sequence SEQ ID NO: 1, 5'-CCTCCCGGCGGAAACCCGCCTGGCACCACCACCACCCGCCGCCCA-3', coding for the linker region, PPGGNPPGTTTTRRP (SEQ ID NO: 2), of the CBH I protein, showing additional proline residues that effect conformation of the linker region in the protein structure.

_US 8,637,293 B2_

SEQUENCE LISTING

```
<160> NUMBER OF SEQ ID NOS: 111

<210> SEQ ID NO 1
<211> LENGTH: 45
<212> TYPE: DNA
<213> ORGANISM: Artificial
<220> FEATURE:
<223> OTHER INFORMATION: Nucleotide encoding linker

<400> SEQUENCE: 1
cctcccggcg aaacccgcc tggcaccacc accaccgcc gccca            45

<210> SEQ ID NO 2
<211> LENGTH: 15
<212> TYPE: PRT
<213> ORGANISM: Trichoderma reesei

<400> SEQUENCE: 2

Pro Pro Gly Gly Asn Pro Pro Gly Thr Thr Thr Thr Arg Arg Pro
1               5                   10                  15

<210> SEQ ID NO 3
<211> LENGTH: 24
<212> TYPE: DNA
<213> ORGANISM: Artificial sequence
<220> FEATURE:
<223> OTHER INFORMATION: Nucleotide encoding linker

<400> SEQUENCE: 3
ggcggaaacc cgcctggcac cacc                                24

<210> SEQ ID NO 4
<211> LENGTH: 1551
<212> TYPE: DNA
<213> ORGANISM: Trichoderma reesei

<400> SEQUENCE: 4
atgtatcgga agttggccgt catctcggcc ttcttggcca cagctcgtgc tcagtcggcc    60
tgcactctcc aatcggagac tcacccgcct ctgacatggc agaaatgctc gtctggtggc   120
acgtgcactc aacagacagg ctccgtggtc atcgacgcca actggcgctg gactcacgct   180
acgaacagca gcacgaactg ctacgatggc aacacttgga gctcgaccct atgtcctgac   240
aacgagacct gcgcgaagaa ctgctgtctg gacggtgccg cctacgcgtc cacgtacgga   300
gttaccacga gcggtaacag cctctccatt ggctttgtca cccagtctgc gcagaagaac   360
gttggcgctc gcctttacct tatggcgagc gacacgacct accaggaatt caccctgctt   420
ggcaacgagt tctctttcga tgttgatgtt tcgcagctgc cgtgcggctt gaacggagct   480
ctctacttcg tgtccatgga cgcggatggt ggcgtgagca gtatcccac caacaccgct   540 ggcgccaagt acggcacggg gtactgtgac agccagtgtc ccgcgatct gaagttcatc   600
```

```
aatggccagg ccaacgttga gggctgggag ccgtcatcca acaacgcgaa cacgggcatt    660
ggaggacacg gaagctgctg ctctgagatg gatatctggg aggccaactc catctccgag    720
gctcttaccc cccaccccttg cacgactgtc ggccaggaga tctgcgaggg tgatgggtgc    780
ggcggaactt actccgataa cagatatggc ggcacttgcg atcccgatgg ctgcgactgg    840
aacccatacc gcctgggcaa caccagcttc tacggccctg gctcaagctt taccctcgat    900
accaccaaga aattgaccgt tgtcacccag ttcgagacgt cgggtgccat caaccgatac    960
tatgtccaga tggcgtcac tttccagcag cccaacgccg agcttggtag ttactctggc   1020
aacgagctca cgatgatta ctgcacagct gaggaggcag aattcggcgg atcctctttc   1080
tcagacaagg gcggcctgac tcagttcaag aaggctacct ctggcggcat ggttctggtc   1140
atgagtctgt gggatgatta ctacgccaac atgctgtggc tggactccac ctacccgaca   1200
aacgagacct cctccacacc cggtgccgtg cgcggaagct gctccaccag ctccggtgtc   1260
cctgctcagg tcgaatctca gtctcccaac gccaaggtca ccttctccaa catcaagttc   1320
ggacccattg gcagcaccgg caaccctagc ggcggcaacc ctcccggcgg aaacccgcct   1380
ggcaccacca ccacccgccg cccagccact accactggaa gctctcccgg acctacccag   1440
tctcactacg gccagtgcgg cggtattggc tacagcggcc ccacggtctg cgccagcggc   1500
acaacttgcc aggtcctgaa cccttactac tctcagtgcc tgtaaagctc c            1551

<210> SEQ ID NO 5
<211> LENGTH: 514
<212> TYPE: PRT
<213> ORGANISM: Trichoderma reesei

<400> SEQUENCE: 5

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205
```

-continued

```
Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
        355                 360                 365

Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 6
<211> LENGTH: 514
<212> TYPE: PRT
<213> ORGANISM: Trichoderma reesei CBH1-N45A

<400> SEQUENCE: 6

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Ala Ser Ser
        50                  55                  60

Thr Asn Cys Tyr Asp Gly Asn Thr Trp Ser Ser Thr Leu Cys Pro Asp
```

```
                65                  70                  75                  80
Asn Glu Thr Cys Ala Lys Asn Cys Cys Leu Asp Gly Ala Ala Tyr Ala
                    85                  90                  95
Ser Thr Tyr Gly Val Thr Thr Ser Gly Asn Ser Leu Ser Ile Gly Phe
                    100                 105                 110
Val Thr Gln Ser Ala Gln Lys Asn Val Gly Ala Arg Leu Tyr Leu Met
                    115                 120                 125
Ala Ser Asp Thr Thr Tyr Gln Glu Phe Thr Leu Leu Gly Asn Glu Phe
                    130                 135                 140
Ser Phe Asp Val Asp Val Ser Gln Leu Pro Cys Gly Leu Asn Gly Ala
145                 150                 155                 160
Leu Tyr Phe Val Ser Met Asp Ala Asp Gly Gly Val Ser Lys Tyr Pro
                    165                 170                 175
Thr Asn Thr Ala Gly Ala Lys Tyr Gly Thr Gly Tyr Cys Asp Ser Gln
                    180                 185                 190
Cys Pro Arg Asp Leu Lys Phe Ile Asn Gly Gln Ala Asn Val Glu Gly
                    195                 200                 205
Trp Glu Pro Ser Ser Asn Asn Ala Asn Thr Gly Ile Gly Gly His Gly
                    210                 215                 220
Ser Cys Cys Ser Glu Met Asp Ile Trp Glu Ala Asn Ser Ile Ser Glu
225                 230                 235                 240
Ala Leu Thr Pro His Pro Cys Thr Thr Val Gly Gln Glu Ile Cys Glu
                    245                 250                 255
Gly Asp Gly Cys Gly Gly Thr Tyr Ser Asp Asn Arg Tyr Gly Gly Thr
                    260                 265                 270
Cys Asp Pro Asp Gly Cys Asp Trp Asn Pro Tyr Arg Leu Gly Asn Thr
                    275                 280                 285
Ser Phe Tyr Gly Pro Gly Ser Ser Phe Thr Leu Asp Thr Thr Lys Lys
                    290                 295                 300
Leu Thr Val Val Thr Gln Phe Glu Thr Ser Gly Ala Ile Asn Arg Tyr
305                 310                 315                 320
Tyr Val Gln Asn Gly Val Thr Phe Gln Gln Pro Asn Ala Glu Leu Gly
                    325                 330                 335
Ser Tyr Ser Gly Asn Glu Leu Asn Asp Asp Tyr Cys Thr Ala Glu Glu
                    340                 345                 350
Ala Glu Phe Gly Gly Ser Ser Phe Ser Asp Lys Gly Gly Leu Thr Gln
                    355                 360                 365
Phe Lys Lys Ala Thr Ser Gly Gly Met Val Leu Val Met Ser Leu Trp
                    370                 375                 380
Asp Asp Tyr Tyr Ala Asn Met Leu Trp Leu Asp Ser Thr Tyr Pro Thr
385                 390                 395                 400
Asn Glu Thr Ser Ser Thr Pro Gly Ala Val Arg Gly Ser Cys Ser Thr
                    405                 410                 415
Ser Ser Gly Val Pro Ala Gln Val Glu Ser Gln Ser Pro Asn Ala Lys
                    420                 425                 430
Val Thr Phe Ser Asn Ile Lys Phe Gly Pro Ile Gly Ser Thr Gly Asn
                    435                 440                 445
Pro Ser Gly Gly Asn Pro Pro Gly Gly Asn Pro Pro Gly Thr Thr Thr
                    450                 455                 460
Thr Arg Arg Pro Ala Thr Thr Thr Gly Ser Ser Pro Gly Pro Thr Gln
465                 470                 475                 480
Ser His Tyr Gly Gln Cys Gly Gly Ile Gly Tyr Ser Gly Pro Thr Val
                    485                 490                 495
```

```
Cys Ala Ser Gly Thr Thr Cys Gln Val Leu Asn Pro Tyr Tyr Ser Gln
                500                 505                 510
Cys Leu

<210> SEQ ID NO 7
<211> LENGTH: 514
<212> TYPE: PRT
<213> ORGANISM: Trichoderma reesei CBH1-N270A

<400> SEQUENCE: 7

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Asn Thr Gly Ser
            35                  40                  45

Val Val Ile Asp Ala Asn Trp Arg Trp Thr His Ala Thr Asn Ser Ser
50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
                100                 105                 110

Val Thr Gln Ser Ala Gln Lys Asn Val Gly Ala Arg Leu Tyr Leu Met
            115                 120                 125

Ala Ser Asp Thr Thr Tyr Gln Glu Phe Thr Leu Leu Gly Asn Glu Phe
130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
            195                 200                 205

Trp Glu Pro Ser Ser Asn Asn Ala Asn Thr Gly Ile Gly Gly His Gly
210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asn Pro Tyr Arg Leu Gly Ala Thr
            275                 280                 285

Ser Phe Tyr Gly Pro Gly Ser Ser Phe Thr Leu Asp Thr Thr Lys Lys
290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
                340                 345                 350

Ala Glu Phe Gly Gly Ser Ser Phe Ser Asp Lys Gly Gly Leu Thr Gln
```

```
                   355                 360                 365
Phe Lys Lys Ala Thr Ser Gly Gly Met Val Leu Val Met Ser Leu Trp
    370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
        435                 440                 445

Pro Ser Gly Gly Asn Pro Pro Gly Gly Asn Pro Pro Gly Thr Thr Thr
    450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
            500                 505                 510

Cys Leu

<210> SEQ ID NO 8
<211> LENGTH: 514
<212> TYPE: PRT
<213> ORGANISM: Trichoderma reesei CBH1-N384A

<400> SEQUENCE: 8

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
            20                  25                  30

Trp Gln Lys Cys Ser Ser Gly Gly Thr Cys Thr Gln Gln Thr Gly Ser
        35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Gly Asn Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220
```

```
Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
            245                 250                 255

Gly Asp Gly Cys Gly Gly Thr Tyr Ser Asp Asn Arg Tyr Gly Gly Thr
        260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
            340                 345                 350

Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Ala Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
            420                 425                 430

Val Thr Phe Ser Asn Ile Lys Phe Gly Pro Ile Gly Ser Thr Gly Asn
            435                 440                 445

Pro Ser Gly Gly Asn Pro Pro Gly Gly Asn Pro Pro Gly Thr Thr Thr
        450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495

Cys Ala Ser Gly Thr Thr Cys Gln Val Leu Asn Pro Tyr Tyr Ser Gln
                500                 505                 510

Cys Leu

<210> SEQ ID NO 9
<211> LENGTH: 28
<212> TYPE: DNA
<213> ORGANISM: Artificial
<220> FEATURE:
<223> OTHER INFORMATION: Primer for PCR

<400> SEQUENCE: 9
agagagtcta gacacggagc ttacaggc                                          28

<210> SEQ ID NO 10
<211> LENGTH: 26
<212> TYPE: DNA
<213> ORGANISM: Artificial
<220> FEATURE:
<223> OTHER INFORMATION: S8P Native sense strand

<400> SEQUENCE: 10
gcactctcca atcggagact cacccg                                            26
```

<210> SEQ ID NO 11
<211> LENGTH: 26
<212> TYPE: DNA
<213> ORGANISM: Artificial
<220> FEATURE:
<223> OTHER INFORMATION: S8P Mutagenic sense strand

<400> SEQUENCE: 11
gcactctcca accggagact cacccg                                    26

<210> SEQ ID NO 12
<211> LENGTH: 26
<212> TYPE: DNA
<213> ORGANISM: Artificial
<220> FEATURE:
<223> OTHER INFORMATION: S8P Mutagenic anti-sense strand

<400> SEQUENCE: 12
cgggtgagtc tccggttgga gagtgc                                    26

<210> SEQ ID NO 13
<211> LENGTH: 28
<212> TYPE: DNA
<213> ORGANISM: Artificial
<220> FEATURE:
<223> OTHER INFORMATION: N27P Native sense strand

<400> SEQUENCE: 13
ggcacgtgca ctcaacagac aggctccg                                  28

<210> SEQ ID NO 14
<211> LENGTH: 28
<212> TYPE: DNA
<213> ORGANISM: Artificial
<220> FEATURE:
<223> OTHER INFORMATION: N27P Mutagenic sense strand

<400> SEQUENCE: 14
ggcacgtgca ctccacagac aggctccg                                  28

<210> SEQ ID NO 15
<211> LENGTH: 28
<212> TYPE: DNA
<213> ORGANISM: Artificial
<220> FEATURE:
<223> OTHER INFORMATION: N27P Mutagenic anti-sense strand

<400> SEQUENCE: 15
cggagcctgt ctgtggagtg cacgtgcc                                  28

<210> SEQ ID NO 16
<211> LENGTH: 32
<212> TYPE: DNA
<213> ORGANISM: Artificial
<220> FEATURE:
<223> OTHER INFORMATION: A43P Native sense strand

<400> SEQUENCE: 16
ggcgctggac tcacgctacg aacagcagca cg                             32

<210> SEQ ID NO 17
<211> LENGTH: 32
<212> TYPE: DNA
<213> ORGANISM: Artificial
<220> FEATURE:
<223> OTHER INFORMATION: A43P Mutagenic sense strand

```
<400> SEQUENCE: 17
ggcgctggac tcaccctacg aacagcagca cg                                    32

<210> SEQ ID NO 18
<211> LENGTH: 32
<212> TYPE: DNA
<213> ORGANISM: Artificial
<220> FEATURE:
<223> OTHER INFORMATION: A43P Mutagenic anti-sense strand

<400> SEQUENCE: 18
cgtgctgctg ttcgtagggt gagtccagcg cc                                    32

<210> SEQ ID NO 19
<211> LENGTH: 26
<212> TYPE: DNA
<213> ORGANISM: Artificial
<220> FEATURE:
<223> OTHER INFORMATION: G75P native sense strand

<400> SEQUENCE: 19
gctgtctgga cggtgccgcc tacgcg                                           26

<210> SEQ ID NO 20
<211> LENGTH: 26
<212> TYPE: DNA
<213> ORGANISM: Artificial
<220> FEATURE:
<223> OTHER INFORMATION: G74P Mutagenic sense strand

<400> SEQUENCE: 20
gctgtctgga ccctgccgcc tacgcg                                           26

<210> SEQ ID NO 21
<211> LENGTH: 26
<212> TYPE: DNA
<213> ORGANISM: Artificial
<220> FEATURE:
<223> OTHER INFORMATION: G75P Mutagenic anti-sense strand

<400> SEQUENCE: 21
cgcgtaggcg gcagggtcca gacagc                                           26

<210> SEQ ID NO 22
<211> LENGTH: 24
<212> TYPE: DNA
<213> ORGANISM: Artificial
<220> FEATURE:
<223> OTHER INFORMATION: G94P Native sense strand

<400> SEQUENCE: 22
gcctctccat tggctttgtc accc                                             24

<210> SEQ ID NO 23
<211> LENGTH: 24
<212> TYPE: DNA
<213> ORGANISM: Artificial
<220> FEATURE:
<223> OTHER INFORMATION: G94P Mutagenic sense strand

<400> SEQUENCE: 23
gcctctccat tccctttgtc accc                                             24

<210> SEQ ID NO 24
<211> LENGTH: 24
```

```
<212> TYPE: DNA
<213> ORGANISM: Artificial
<220> FEATURE:
<223> OTHER INFORMATION: G94P Mutagenic anti-sense strand

<400> SEQUENCE: 24
gggtgacaaa gggaatggag aggc                                          24

<210> SEQ ID NO 25
<211> LENGTH: 24
<212> TYPE: DNA
<213> ORGANISM: Artificial
<220> FEATURE:
<223> OTHER INFORMATION: E190P Native sense strand

<400> SEQUENCE: 25
ggccaacgtt gagggctggg agcc                                          24

<210> SEQ ID NO 26
<211> LENGTH: 24
<212> TYPE: DNA
<213> ORGANISM: Artificial
<220> FEATURE:
<223> OTHER INFORMATION: E190P Mutagenic sense strand

<400> SEQUENCE: 26
ggccaacgtt ccgggctggg agcc                                          24

<210> SEQ ID NO 27
<211> LENGTH: 24
<212> TYPE: DNA
<213> ORGANISM: Artificial
<220> FEATURE:
<223> OTHER INFORMATION: E190 Mutagenic anti-sense strand

<400> SEQUENCE: 27
ggctcccagc ccggaacgtt ggcc                                          24

<210> SEQ ID NO 28
<211> LENGTH: 27
<212> TYPE: DNA
<213> ORGANISM: Artificial
<220> FEATURE:
<223> OTHER INFORMATION: S195P Native sense strand

<400> SEQUENCE: 28
ggctgggagc cgtcatccaa caacgcg                                       27

<210> SEQ ID NO 29
<211> LENGTH: 27
<212> TYPE: DNA
<213> ORGANISM: Artificial
<220> FEATURE:
<223> OTHER INFORMATION: S195P Mutagenic sense strand

<400> SEQUENCE: 29
ggctgggagc cgccatccaa caacgcg                                       27

<210> SEQ ID NO 30
<211> LENGTH: 27
<212> TYPE: DNA
<213> ORGANISM: Artificial
<220> FEATURE:
<223> OTHER INFORMATION: S195P Mutagenic anti-sense strand

<400> SEQUENCE: 30
cgcgttgttg gatggcggct cccagcc                                       27
```

```
<210> SEQ ID NO 31
<211> LENGTH: 32
<212> TYPE: DNA
<213> ORGANISM: Artificial
<220> FEATURE:
<223> OTHER INFORMATION: K287P Native sense strand

<400> SEQUENCE: 31
cgataccacc aagaaattga ccgttgtcac cc                                       32

<210> SEQ ID NO 32
<211> LENGTH: 32
<212> TYPE: DNA
<213> ORGANISM: Artificial
<220> FEATURE:
<223> OTHER INFORMATION: K287P Mutagenic sense strand

<400> SEQUENCE: 32
cgataccacc aagccattga ccgttgtcac cc                                       32

<210> SEQ ID NO 33
<211> LENGTH: 32
<212> TYPE: DNA
<213> ORGANISM: Artificial
<220> FEATURE:
<223> OTHER INFORMATION: K287P Mutagenic anti-sense strand

<400> SEQUENCE: 33
gggtgacaac ggtcaatggc ttggtggtat cg                                       32

<210> SEQ ID NO 34
<211> LENGTH: 28
<212> TYPE: DNA
<213> ORGANISM: Artificial
<220> FEATURE:
<223> OTHER INFORMATION: A299P Native sense strand

<400> SEQUENCE: 34
cgagacgtcg ggtgccatca accgatac                                            28

<210> SEQ ID NO 35
<211> LENGTH: 28
<212> TYPE: DNA
<213> ORGANISM: Artificial
<220> FEATURE:
<223> OTHER INFORMATION: A299P Mutagenic sense strand

<400> SEQUENCE: 35
cgagacgtcg ggtcccatca accgatac                                            28

<210> SEQ ID NO 36
<211> LENGTH: 28
<212> TYPE: DNA
<213> ORGANISM: Artificial
<220> FEATURE:
<223> OTHER INFORMATION: A299P Mutagenic anti-sense strand

<400> SEQUENCE: 36
gtatcggttg atgggacccg acgtctcg                                            28

<210> SEQ ID NO 37
<211> LENGTH: 35
<212> TYPE: DNA
<213> ORGANISM: Artificial
<220> FEATURE:
<223> OTHER INFORMATION: Q312P/N315P Native sense strand
```

<400> SEQUENCE: 37
ggcgtcactt tccagcagcc caacgccgag cttgg       35

<210> SEQ ID NO 38
<211> LENGTH: 35
<212> TYPE: DNA
<213> ORGANISM: Artificial
<220> FEATURE:
<223> OTHER INFORMATION: Q312P/N315P Mutagenic sense strand

<400> SEQUENCE: 38
ggcgtcactt tcccgcagcc ccccgccgag cttgg       35

<210> SEQ ID NO 39
<211> LENGTH: 35
<212> TYPE: DNA
<213> ORGANISM: Artificial
<220> FEATURE:
<223> OTHER INFORMATION: Q312P/N315P Mutagenic anti-sense strand

<400> SEQUENCE: 39
ccaagctcgg cgggggggctg cgggaaagtg acgcc       35

<210> SEQ ID NO 40
<211> LENGTH: 26
<212> TYPE: DNA
<213> ORGANISM: Artificial
<220> FEATURE:
<223> OTHER INFORMATION: G359P Native sense strand

<400> SEQUENCE: 40
ggctacctct ggcggcatgg ttctgg       26

<210> SEQ ID NO 41
<211> LENGTH: 26
<212> TYPE: DNA
<213> ORGANISM: Artificial
<220> FEATURE:
<223> OTHER INFORMATION: G359P Mutagenic sense strand

<400> SEQUENCE: 41
ggctacctct cccggcatgg ttctgg       26

<210> SEQ ID NO 42
<211> LENGTH: 26
<212> TYPE: DNA
<213> ORGANISM: Artificial
<220> FEATURE:
<223> OTHER INFORMATION: G359P Mutagenic anti-sense strand

<400> SEQUENCE: 42
ccagaaccat gccgggagag gtagcc       26

<210> SEQ ID NO 43
<211> LENGTH: 34
<212> TYPE: DNA
<213> ORGANISM: Artificial
<220> FEATURE:
<223> OTHER INFORMATION: S398P/S401P Native sense strand

<400> SEQUENCE: 43
gcggaagctg ctccaccagc tccggtgtcc ctgc       34

<210> SEQ ID NO 44
<211> LENGTH: 34

```
<212> TYPE: DNA
<213> ORGANISM: Artificial
<220> FEATURE:
<223> OTHER INFORMATION: S398P/S410P Mutagenic sense strand

<400> SEQUENCE: 44
gcggaagctg ccccaccagc cccggtgtcc ctgc                              34

<210> SEQ ID NO 45
<211> LENGTH: 34
<212> TYPE: DNA
<213> ORGANISM: Artificial
<220> FEATURE:
<223> OTHER INFORMATION: S398P/S401P Mutagenic anti-sense strand

<400> SEQUENCE: 45
gcagggacac cggggctggt ggggcagctt ccgc                              34

<210> SEQ ID NO 46
<211> LENGTH: 22
<212> TYPE: DNA
<213> ORGANISM: Artificial
<220> FEATURE:
<223> OTHER INFORMATION: A414P Native sense strand

<400> SEQUENCE: 46
gtctcccaac gccaaggtca cc                                           22

<210> SEQ ID NO 47
<211> LENGTH: 22
<212> TYPE: DNA
<213> ORGANISM: Artificial
<220> FEATURE:
<223> OTHER INFORMATION: A414P Mutagenic sense strand

<400> SEQUENCE: 47
gtctcccaac cccaaggtca cc                                           22

<210> SEQ ID NO 48
<211> LENGTH: 22
<212> TYPE: DNA
<213> ORGANISM: Artificial
<220> FEATURE:
<223> OTHER INFORMATION: A414P Mutagenic anti-sense strand

<400> SEQUENCE: 48
ggtgaccttg ggggttgggag ac                                          22

<210> SEQ ID NO 49
<211> LENGTH: 32
<212> TYPE: DNA
<213> ORGANISM: Artificial
<220> FEATURE:
<223> OTHER INFORMATION: N431P/S433P Native sense strand

<400> SEQUENCE: 49
ggcagcaccg gcaaccctag cggcggcaac cc                                32

<210> SEQ ID NO 50
<211> LENGTH: 32
<212> TYPE: DNA
<213> ORGANISM: Artificial
<220> FEATURE:
<223> OTHER INFORMATION: N431P/S433P Mutagenic sense strand

<400> SEQUENCE: 50
ggcagcaccg gcccccctcc cggcggcaac cc                                32
```

```
<210> SEQ ID NO 51
<211> LENGTH: 32
<212> TYPE: DNA
<213> ORGANISM: Artificial
<220> FEATURE:
<223> OTHER INFORMATION: N431P/S433P Mutagenic anti-sense strand

<400> SEQUENCE: 51 ggguutgccgc cgggaggggg gccggtgctg cc                                32

<210> SEQ ID NO 52
<211> LENGTH: 36
<212> TYPE: DNA
<213> ORGANISM: Artificial
<220> FEATURE:
<223> OTHER INFORMATION: S99G Native sense strand

<400> SEQUENCE: 52
ggctttgtca cccagtctgc gcagaagaac gttggc                             36

<210> SEQ ID NO 53
<211> LENGTH: 36
<212> TYPE: DNA
<213> ORGANISM: Artificial
<220> FEATURE:
<223> OTHER INFORMATION: S99G Mutagenic sense strand

<400> SEQUENCE: 53
ggctttgtca cccagggtgc gcagaagaac gttggc                             36

<210> SEQ ID NO 54
<211> LENGTH: 36
<212> TYPE: DNA
<213> ORGANISM: Artificial
<220> FEATURE:
<223> OTHER INFORMATION: S99G Mutagenic anti-sense strand

<400> SEQUENCE: 54
gccaacgttc ttctgcgcac cctgggtgac aaagcc                             36

<210> SEQ ID NO 55
<211> LENGTH: 20
<212> TYPE: DNA
<213> ORGANISM: Artificial
<220> FEATURE:
<223> OTHER INFORMATION: R251A Native sense strand

<400> SEQUENCE: 55
ccgataacag atatggcggc                                               20

<210> SEQ ID NO 56
<211> LENGTH: 20
<212> TYPE: DNA
<213> ORGANISM: Artificial
<220> FEATURE:
<223> OTHER INFORMATION: R251A Mutagenic sense strand

<400> SEQUENCE: 56
ccgataacgc ctatggcggc                                               20

<210> SEQ ID NO 57
<211> LENGTH: 20
<212> TYPE: DNA
<213> ORGANISM: Artificial
<220> FEATURE:
<223> OTHER INFORMATION: R251A Mutagenic anti-sense strand
```

<400> SEQUENCE: 57
gccgccatag gcgttatcgg                                                 20

<210> SEQ ID NO 58
<211> LENGTH: 30
<212> TYPE: DNA
<213> ORGANISM: Artificial
<220> FEATURE:
<223> OTHER INFORMATION: R394A Native sense strand

<400> SEQUENCE: 58
cccggtgccg tgcgcggaag ctgctccacc                                      30

<210> SEQ ID NO 59
<211> LENGTH: 30
<212> TYPE: DNA
<213> ORGANISM: Artificial
<220> FEATURE:
<223> OTHER INFORMATION: R394A Mutagenic sense strand

<400> SEQUENCE: 59
cccggtgccg tggccggaag ctgctccacc                                      30

<210> SEQ ID NO 60
<211> LENGTH: 30
<212> TYPE: DNA
<213> ORGANISM: Artificial
<220> FEATURE:
<223> OTHER INFORMATION: R394A Mutagenic anti-sense strand

<400> SEQUENCE: 60
ggtggagcag cttccggcca cggcaccggg                                      30

<210> SEQ ID NO 61
<211> LENGTH: 35
<212> TYPE: DNA
<213> ORGANISM: Artificial
<220> FEATURE:
<223> OTHER INFORMATION: F338A Native sense strand

<400> SEQUENCE: 61
gctgaggagg cagaattcgg cggatcctct ttctc                                35

<210> SEQ ID NO 62
<211> LENGTH: 35
<212> TYPE: DNA
<213> ORGANISM: Artificial
<220> FEATURE:
<223> OTHER INFORMATION: F338A Mutagenic sense strand

<400> SEQUENCE: 62
gctgaggagg cagaagccgg cggatcctct ttctc                                35

<210> SEQ ID NO 63
<211> LENGTH: 35
<212> TYPE: DNA
<213> ORGANISM: Artificial
<220> FEATURE:
<223> OTHER INFORMATION: F338A Mutagenic anti-sense strand

<400> SEQUENCE: 63
gagaaagagg atccgccggc ttctgcctcc tcagc                                35

<210> SEQ ID NO 64
<211> LENGTH: 29

```
<212> TYPE: DNA
<213> ORGANISM: Artificial
<220> FEATURE:
<223> OTHER INFORMATION: R267A Native sense strand

<400> SEQUENCE: 64
ggaacccata ccgcctgggc aacaccagc                                29

<210> SEQ ID NO 65
<211> LENGTH: 29
<212> TYPE: DNA
<213> ORGANISM: Artificial
<220> FEATURE:
<223> OTHER INFORMATION: R267A Mutagenic sense strand

<400> SEQUENCE: 65
ggaacccata cgccctgggc aacaccagc                                29

<210> SEQ ID NO 66
<211> LENGTH: 29
<212> TYPE: DNA
<213> ORGANISM: Artificial
<220> FEATURE:
<223> OTHER INFORMATION: R267A Mutagenic anti-sense strand

<400> SEQUENCE: 66
gctggtgttg cccagggcgt atgggttcc                                29

<210> SEQ ID NO 67
<211> LENGTH: 34
<212> TYPE: DNA
<213> ORGANISM: Artificial
<220> FEATURE:
<223> OTHER INFORMATION: E285A Native sense strand

<400> SEQUENCE: 67
cctacccgac aaacgagacc tcctccacac ccgg                          34

<210> SEQ ID NO 68
<211> LENGTH: 34
<212> TYPE: DNA
<213> ORGANISM: Artificial
<220> FEATURE:
<223> OTHER INFORMATION: E385A Mutagenic sense strand

<400> SEQUENCE: 68
cctacccgac aaacgccacc tcctccacac ccgg                          34

<210> SEQ ID NO 69
<211> LENGTH: 34
<212> TYPE: DNA
<213> ORGANISM: Artificial
<220> FEATURE:
<223> OTHER INFORMATION: E385A Mutagenic anti-sense strand

<400> SEQUENCE: 69
ccgggtgtgg aggaggtggc gtttgtcggg tagg                          34

<210> SEQ ID NO 70
<211> LENGTH: 32
<212> TYPE: DNA
<213> ORGANISM: Artificial
<220> FEATURE:
<223> OTHER INFORMATION: N45A Native sense strand

<400> SEQUENCE: 70
ggactcacgc tacggccagc agcacgaact gc                            32
```

<210> SEQ ID NO 71
<211> LENGTH: 32
<212> TYPE: DNA
<213> ORGANISM: Artificial
<220> FEATURE:
<223> OTHER INFORMATION: N45A Mutagenic sense strand

<400> SEQUENCE: 71
ggactcacgc tacgaacagc agcacgaact gc        32

<210> SEQ ID NO 72
<211> LENGTH: 32
<212> TYPE: DNA
<213> ORGANISM: Artificial
<220> FEATURE:
<223> OTHER INFORMATION: N45A Mutagenic anti-sense strand

<400> SEQUENCE: 72
gcagttcgtg ctgctggccg tagcgtgagt cc        32

<210> SEQ ID NO 73
<211> LENGTH: 36
<212> TYPE: DNA
<213> ORGANISM: Artificial
<220> FEATURE:
<223> OTHER INFORMATION: N270A Native sense strand

<400> SEQUENCE: 73
cccataccgc ctgggcaaca ccagcttcta cggccc        36

<210> SEQ ID NO 74
<211> LENGTH: 36
<212> TYPE: DNA
<213> ORGANISM: Artificial
<220> FEATURE:
<223> OTHER INFORMATION: N270A Mutagenic sense strand

<400> SEQUENCE: 74
cccataccgc ctgggcgcca ccagcttcta cggccc        36

<210> SEQ ID NO 75
<211> LENGTH: 36
<212> TYPE: DNA
<213> ORGANISM: Artificial
<220> FEATURE:
<223> OTHER INFORMATION: N270A Mutagenic anti-sense strand

<400> SEQUENCE: 75
gggccgtaga agctggtggc gcccaggcgg tatggg        36

<210> SEQ ID NO 76
<211> LENGTH: 41
<212> TYPE: DNA
<213> ORGANISM: Artificial
<220> FEATURE:
<223> OTHER INFORMATION: N384A Native sense strand

<400> SEQUENCE: 76
ggactccacc tacccgacaa acgagacctc ctccacaccc g        41

<210> SEQ ID NO 77
<211> LENGTH: 41
<212> TYPE: DNA
<213> ORGANISM: Artificial
<220> FEATURE:
<223> OTHER INFORMATION: N384A Mutagenic sense strand

```
<400> SEQUENCE: 77
ggactccacc tacccgacag ccgagacctc ctccacaccc g                          41

<210> SEQ ID NO 78
<211> LENGTH: 41
<212> TYPE: DNA
<213> ORGANISM: Artificial
<220> FEATURE:
<223> OTHER INFORMATION: N384A Mutagenic anti-sense strand

<400> SEQUENCE: 78
cgggtgtgga ggaggtctcg gctgtcgggt aggtggagtc c                          41

<210> SEQ ID NO 79
<211> LENGTH: 23
<212> TYPE: DNA
<213> ORGANISM: Artificial
<220> FEATURE:
<223> OTHER INFORMATION: E337R Native sense strand

<400> SEQUENCE: 79
gctgaggagg cagaattcgg cgg                                              23

<210> SEQ ID NO 80
<211> LENGTH: 23
<212> TYPE: DNA
<213> ORGANISM: Artificial
<220> FEATURE:
<223> OTHER INFORMATION: E337R Mutagenic sense strand

<400> SEQUENCE: 80
gctgaggagg cacgcttcgg cgg                                              23

<210> SEQ ID NO 81
<211> LENGTH: 23
<212> TYPE: DNA
<213> ORGANISM: Artificial
<220> FEATURE:
<223> OTHER INFORMATION: E337R Mutagenic anti-sense strand

<400> SEQUENCE: 81
ccgccgaagc gtgcctcctc agc                                              23

<210> SEQ ID NO 82
<211> LENGTH: 27
<212> TYPE: DNA
<213> ORGANISM: Artificial
<220> FEATURE:
<223> OTHER INFORMATION: N327D Native sense strand

<400> SEQUENCE: 82
ggcaacgagc tcaacgatga ttactgc                                          27

<210> SEQ ID NO 83
<211> LENGTH: 27
<212> TYPE: DNA
<213> ORGANISM: Artificial
<220> FEATURE:
<223> OTHER INFORMATION: N327D Mutagenic sense strand

<400> SEQUENCE: 83
ggcaacgagc tcgacgatga ttactgc                                          27

<210> SEQ ID NO 84
<211> LENGTH: 27
```

-continued

<212> TYPE: DNA
<213> ORGANISM: Artificial
<220> FEATURE:
<223> OTHER INFORMATION: N327D Mutagenic anti-sense strand

<400> SEQUENCE: 84
gcagtaatca tcgtcgagct cgttgcc                                             27

<210> SEQ ID NO 85
<211> LENGTH: 35
<212> TYPE: DNA
<213> ORGANISM: Artificial
<220> FEATURE:
<223> OTHER INFORMATION: A405D Native sense strand

<400> SEQUENCE: 85
ccggtgtccc tgctcaggtc gaatctcagt ctccc                                    35

<210> SEQ ID NO 86
<211> LENGTH: 35
<212> TYPE: DNA
<213> ORGANISM: Artificial
<220> FEATURE:
<223> OTHER INFORMATION: A405D Mutagenic sense strand

<400> SEQUENCE: 86
ccggtgtccc tgatcaggtc gaatctcagt ctccc                                    35

<210> SEQ ID NO 87
<211> LENGTH: 35
<212> TYPE: DNA
<213> ORGANISM: Artificial
<220> FEATURE:
<223> OTHER INFORMATION: A405D Mutagenic anti-sense strand

<400> SEQUENCE: 87
gggagactga gattcgacct gatcagggac accgg                                    35

<210> SEQ ID NO 88
<211> LENGTH: 30
<212> TYPE: DNA
<213> ORGANISM: Artificial
<220> FEATURE:
<223> OTHER INFORMATION: Q410R Native sense strand

<400> SEQUENCE: 88
gctcaggtcg aatctcagtc tcccaacgcc                                          30

<210> SEQ ID NO 89
<211> LENGTH: 30
<212> TYPE: DNA
<213> ORGANISM: Artificial
<220> FEATURE:
<223> OTHER INFORMATION: Q410R Mutagenic sense strand

<400> SEQUENCE: 89
gctcaggtcg aatctcgctc tcccaacgcc                                          30

<210> SEQ ID NO 90
<211> LENGTH: 30
<212> TYPE: DNA
<213> ORGANISM: Artificial
<220> FEATURE:
<223> OTHER INFORMATION: Q410R Mutagenic anti-sense strand

<400> SEQUENCE: 90
ggcgttggga gagcgagatt cgacctgagc                                          30

<210> SEQ ID NO 91
<211> LENGTH: 29
<212> TYPE: DNA
<213> ORGANISM: Artificial
<220> FEATURE:
<223> OTHER INFORMATION: N64D Native sense strand

<400> SEQUENCE: 91
ccctatgtcc tgacaacgag acctgcgcg                                29

<210> SEQ ID NO 92
<211> LENGTH: 29
<212> TYPE: DNA
<213> ORGANISM: Artificial
<220> FEATURE:
<223> OTHER INFORMATION: N64D Mutagenic sense strand

<400> SEQUENCE: 92
ccctatgtcc tgacgacgag acctgcgcg                                29

<210> SEQ ID NO 93
<211> LENGTH: 29
<212> TYPE: DNA
<213> ORGANISM: Artificial
<220> FEATURE:
<223> OTHER INFORMATION: N64D Mutagenic anti-sense strand

<400> SEQUENCE: 93
cgcgcaggtc tcgtcgtcag gacataggg                                29

<210> SEQ ID NO 94
<211> LENGTH: 44
<212> TYPE: DNA
<213> ORGANISM: Artificial
<220> FEATURE:
<223> OTHER INFORMATION: N64D Native sense strand

<400> SEQUENCE: 94
gctcgaccct atgtcctgac aacgagacct gcgcgaagaa ctgc                44

<210> SEQ ID NO 95
<211> LENGTH: 44
<212> TYPE: DNA
<213> ORGANISM: Artificial
<220> FEATURE:
<223> OTHER INFORMATION: N64D Mutagenic sense strand

<400> SEQUENCE: 95
gctcgaccct atgtcctgac gacgagacct gcgcgaagaa ctgc                44

<210> SEQ ID NO 96
<211> LENGTH: 44
<212> TYPE: DNA
<213> ORGANISM: Artificial
<220> FEATURE:
<223> OTHER INFORMATION: N64D Mutagenic anti-sense strand

<400> SEQUENCE: 96
gcagttcttc gcgcaggtct cgtcgtcagg acatagggtc gagc                44

<210> SEQ ID NO 97
<211> LENGTH: 35
<212> TYPE: DNA
<213> ORGANISM: Artificial
<220> FEATURE:
<223> OTHER INFORMATION: Primer

<400> SEQUENCE: 97

```
aaagaagcgc ggccgcgcct gcactctcca atcgg                                35
```

<210> SEQ ID NO 98
<211> LENGTH: 1500
<212> TYPE: DNA
<213> ORGANISM: Trichoderma reesei

<400> SEQUENCE: 98

```
cagtcggcct gcactctcca atcggagact cacccgcctc tgacatggca gaaatgctcg     60
tctggtggca cgtgcactca acagacaggc tccgtggtca tcgacgccaa ctggcgctgg    120
actcacgcta cgaacagcag cacgaactgc tacgatggca cacttggag ctcgacccta     180
tgtcctgaca cgagacctg cgcgaagaac tgctgtctgg acggtgccgc ctacgcgtcc     240
acgtacggag ttaccacgag cggtaacagc ctctccattg gctttgtcac ccagtctgcg    300
cagaagaacg ttggcgctcg cctttacctt atggcgagcg acgaccta ccaggaattc      360
accctgcttg caacgagtt ctctttcgat gttgatgttt cgcagctgcc gtgcggcttg     420
aacggagctc tctacttcgt gtccatggac gcggatggtg gcgtgagcaa gtatcccacc    480
aacaccgctg gcgccaagta cggcacgggg tactgtgaca gccagtgtcc ccgcgatctg    540
aagttcatca atggccaggc caacgttgag ggctgggagc cgtcatccaa caacgcgaac    600
acgggcattg gaggacacgg aagctgctgc tctgagatgg atatctggga ggccaactcc    660
atctccgagg ctcttacccc ccaccctttgc acgactgtcg gccaggagat ctgcgagggt    720
gatgggtgcg gcggaactta ctccgataac agatatggcg gcacttgcga tcccgatggc    780
tgcgactgga acccataccg cctgggcaac accagcttct acggccctgg ctcaagcttt    840
accctcgata ccaccaagaa attgaccgtt gtcacccagt tcgagacgtc gggtgccatc    900
aaccgatact atgtccagaa tggcgtcact ttccagcagc ccaacgccga gcttggtagt    960
tactctggca acgagctcaa cgatgattac tgcacagctg aggaggcaga attcggcgga   1020
tcctctttct cagacaaggg cggcctgact cagttcaaga aggctacctc tggcggcatg   1080
gttctggtca tgagtctgtg ggatgattac tacgccaaca tgctgtggct ggactccacc   1140
tacccgacaa cgagacctc ctccacaccc ggtgccgtgc gcggaagctg ctccaccagc   1200
tccggtgtcc ctgctcaggt cgaatctcag tctcccaacg ccaaggtcac cttctccaac   1260
atcaagttcg gacccattgg cagcaccggc aaccctagcg gcggcaaccc tcccggcgga   1320
aacccgcctg gcaccaccac caccgccgc ccagccacta ccactggaag ctctcccgga   1380
cctacccagt ctcactacgg ccagtgcggc ggtattggct acagcggccc cacggtctgc   1440
gccagcggca caacttgcca ggtcctgaac ccttactact ctcagtgcct gtaaagctcc   1500
```

<210> SEQ ID NO 99
<211> LENGTH: 497
<212> TYPE: PRT
<213> ORGANISM: Trichoderma reesei

<400> SEQUENCE: 99

```
Gln Ser Ala Cys Thr Leu Gln Ser Glu Thr His Pro Pro Leu Thr Trp
 1               5                  10                  15

Gln Lys Cys Ser Ser Gly Gly Thr Cys Thr Gln Gln Thr Gly Ser Val
                20                  25                  30

Val Ile Asp Ala Asn Trp Arg Trp Thr His Ala Thr Asn Ser Ser Thr
            35                  40                  45
```

-continued

```
Asn Cys Tyr Asp Gly Asn Thr Trp Ser Ser Thr Leu Cys Pro Asp Asn
 50                      55                  60
Glu Thr Cys Ala Lys Asn Cys Cys Leu Asp Gly Ala Ala Tyr Ala Ser
 65                  70                  75                  80
Thr Tyr Gly Val Thr Thr Ser Gly Asn Ser Leu Ser Ile Gly Phe Val
                     85                  90                  95
Thr Gln Ser Ala Gln Lys Asn Val Gly Ala Arg Leu Tyr Leu Met Ala
                100                 105                 110
Ser Asp Thr Thr Tyr Gln Glu Phe Thr Leu Leu Gly Asn Glu Phe Ser
            115                 120                 125
Phe Asp Val Asp Val Ser Gln Leu Pro Cys Gly Leu Asn Gly Ala Leu
        130                 135                 140
Tyr Phe Val Ser Met Asp Ala Asp Gly Gly Val Ser Lys Tyr Pro Thr
145                 150                 155                 160
Asn Thr Ala Gly Ala Lys Tyr Gly Thr Gly Tyr Cys Asp Ser Gln Cys
                165                 170                 175
Pro Arg Asp Leu Lys Phe Ile Asn Gly Gln Ala Asn Val Glu Gly Trp
            180                 185                 190
Glu Pro Ser Ser Asn Asn Ala Asn Thr Gly Ile Gly Gly His Gly Ser
        195                 200                 205
Cys Cys Ser Glu Met Asp Ile Trp Glu Ala Asn Ser Ile Ser Glu Ala
210                 215                 220
Leu Thr Pro His Pro Cys Thr Thr Val Gly Gln Glu Ile Cys Glu Gly
225                 230                 235                 240
Asp Gly Cys Gly Gly Thr Tyr Ser Asp Asn Arg Tyr Gly Gly Thr Cys
                245                 250                 255
Asp Pro Asp Gly Cys Asp Trp Asn Pro Tyr Arg Leu Gly Asn Thr Ser
            260                 265                 270
Phe Tyr Gly Pro Gly Ser Ser Phe Thr Leu Asp Thr Thr Lys Lys Leu
        275                 280                 285
Thr Val Val Thr Gln Phe Glu Thr Ser Gly Ala Ile Asn Arg Tyr Tyr
290                 295                 300
Val Gln Asn Gly Val Thr Phe Gln Gln Pro Asn Ala Glu Leu Gly Ser
305                 310                 315                 320
Tyr Ser Gly Asn Glu Leu Asn Asp Asp Tyr Cys Thr Ala Glu Glu Ala
                325                 330                 335
Glu Phe Gly Gly Ser Ser Phe Ser Asp Lys Gly Gly Leu Thr Gln Phe
            340                 345                 350
Lys Lys Ala Thr Ser Gly Gly Met Val Leu Val Met Ser Leu Trp Asp
        355                 360                 365
Asp Tyr Tyr Ala Asn Met Leu Trp Leu Asp Ser Thr Tyr Pro Thr Asn
370                 375                 380
Glu Thr Ser Ser Thr Pro Gly Ala Val Arg Gly Ser Cys Ser Thr Ser
385                 390                 395                 400
Ser Gly Val Pro Ala Gln Val Glu Ser Gln Ser Pro Asn Ala Lys Val
                405                 410                 415
Thr Phe Ser Asn Ile Lys Phe Gly Pro Ile Gly Ser Thr Gly Asn Pro
            420                 425                 430
Ser Gly Gly Asn Pro Pro Gly Gly Asn Pro Pro Gly Thr Thr Thr Thr
        435                 440                 445
Arg Arg Pro Ala Thr Thr Thr Gly Ser Ser Pro Gly Pro Thr Gln Ser
450                 455                 460
His Tyr Gly Gln Cys Gly Gly Ile Gly Tyr Ser Gly Pro Thr Val Cys
465                 470                 475                 480
```

Ala Ser Gly Thr Thr Cys Gln Val Leu Asn Pro Tyr Tyr Ser Gln Cys
            485                 490                 495

Leu

<210> SEQ ID NO 100
<211> LENGTH: 514
<212> TYPE: PRT
<213> ORGANISM: Trichoderma viride

<400> SEQUENCE: 100

Met Tyr Gln Lys Leu Ala Leu Ile Ser Ala Phe Leu Ala Thr Ala Arg
1               5                   10                  15

Ala Gln Ser Ala Cys Thr Leu Gln Ala Glu Thr His Pro Pro Leu Thr
            20                  25                  30

Trp Gln Lys Cys Ser Ser Gly Gly Thr Cys Thr Gln Gln Thr Gly Ser
            35                  40                  45

Val Val Ile Asp Ala Asn Trp Arg Trp Thr His Ala Thr Asn Ser Ser
    50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
                85                  90                  95

Ser Thr Tyr Gly Val Thr Thr Ser Ala Asp Ser Leu Ser Ile Gly Phe
            100                 105                 110

Val Thr Gln Ser Ala Gln Lys Asn Val Gly Ala Arg Leu Tyr Leu Met
        115                 120                 125

Ala Ser Asp Thr Thr Tyr Gln Glu Phe Thr Leu Leu Gly Asn Glu Phe
    130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
            180                 185                 190

Cys Pro Arg Asp Leu Lys Phe Ile Asn Gly Gln Ala Asn Val Glu Gly
        195                 200                 205

Trp Glu Pro Ser Ser Asn Asn Ala Asn Thr Gly Ile Gly Gly His Gly
    210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Asp
                245                 250                 255

Gly Asp Ser Cys Gly Gly Thr Tyr Ser Gly Asp Arg Tyr Gly Gly Thr
            260                 265                 270

Cys Asp Pro Asp Gly Cys Asp Trp Asn Pro Tyr Arg Leu Gly Asn Thr
        275                 280                 285

Ser Phe Tyr Gly Pro Gly Ser Ser Phe Thr Leu Asp Thr Thr Lys Lys
    290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Asp Tyr Ser Gly Asn Ser Leu Asp Asp Tyr Cys Ala Ala Glu Glu
            340                 345                 350

```
Ala Glu Phe Gly Gly Ser Ser Phe Ser Asp Lys Gly Gly Leu Thr Gln
            355                 360                 365

Phe Lys Lys Ala Thr Ser Gly Gly Met Val Leu Val Met Ser Leu Trp
370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
            405                 410                 415

Ser Ser Gly Val Pro Ala Gln Leu Glu Ser Asn Ser Pro Asn Ala Lys
            420                 425                 430

Val Val Tyr Ser Asn Ile Lys Phe Gly Pro Ile Gly Ser Thr Gly Asn
            435                 440                 445

Ser Ser Gly Gly Asn Pro Pro Gly Gly Asn Pro Pro Gly Thr Thr Thr
            450                 455                 460

Thr Arg Arg Pro Ala Thr Ser Thr Gly Ser Ser Pro Gly Pro Thr Gln
465                 470                 475                 480

Thr His Tyr Gly Gln Cys Gly Gly Ile Gly Tyr Ser Gly Pro Thr Val
            485                 490                 495

Cys Ala Ser Gly Ser Thr Cys Gln Val Leu Asn Pro Tyr Tyr Ser Gln
            500                 505                 510

Cys Leu

<210> SEQ ID NO 101
<211> LENGTH: 504
<212> TYPE: PRT
<213> ORGANISM: Hypocrea lixii

<400> SEQUENCE: 101

Met Tyr Arg Lys Leu Ala Val Ile Ser Ala Phe Leu Ala Ala Ala Arg
1               5                   10                  15

Ala Gln Gln Val Cys Thr Gln Ala Glu Thr His Pro Pro Leu Thr
            20                  25                  30

Trp Gln Lys Cys Thr Ala Ser Gly Cys Thr Pro Gln Gln Gly Ser Val
                35                  40                  45

Val Leu Asp Ala Asn Trp Arg Trp Thr His Asp Thr Lys Ser Thr Thr
50                  55                  60

Asn Cys Tyr Asp Gly Asn Thr Trp Ser Ser Thr Leu Cys Pro Asp Asp
65                  70                  75                  80

Ala Thr Cys Ala Lys Asn Cys Cys Leu Asp Gly Ala Asn Tyr Ser Gly
                85                  90                  95

Thr Tyr Gly Val Thr Thr Ser Gly Asp Ala Leu Thr Leu Gln Phe Val
            100                 105                 110

Thr Ala Ser Asn Val Gly Ser Arg Leu Tyr Leu Met Ala Asn Asp Ser
            115                 120                 125

Thr Tyr Gln Glu Phe Thr Leu Ser Gly Asn Glu Phe Ser Phe Asp Val
        130                 135                 140

Asp Val Ser Gln Leu Pro Cys Gly Leu Asn Gly Ala Leu Tyr Phe Val
145                 150                 155                 160

Ser Met Asp Ala Asp Gly Gly Gln Ser Lys Tyr Pro Gly Asn Ala Ala
                165                 170                 175

Gly Ala Lys Tyr Gly Thr Gly Tyr Cys Asp Ser Gln Cys Pro Arg Asp
            180                 185                 190

Leu Lys Phe Ile Asn Gly Gln Ala Asn Val Glu Gly Trp Glu Pro Ser
        195                 200                 205

Ser Asn Asn Ala Asn Thr Gly Val Gly Gly His Gly Ser Cys Cys Ser
```

```
            210                 215                 220
Glu Met Asp Ile Trp Glu Ala Asn Ser Ile Ser Glu Ala Leu Thr Pro
225                 230                 235                 240

His Pro Cys Glu Thr Val Gly Gln Thr Met Cys Ser Gly Asp Ser Cys
                245                 250                 255

Gly Gly Thr Tyr Ser Asn Asp Arg Tyr Gly Gly Thr Cys Asp Pro Asp
                260                 265                 270

Gly Cys Asp Trp Asn Pro Tyr Arg Leu Gly Asn Thr Ser Phe Tyr Gly
                275                 280                 285

Pro Gly Ser Ser Phe Ala Leu Asp Thr Lys Lys Leu Thr Val Val
    290                 295                 300

Thr Gln Phe Ala Thr Asp Gly Ser Ile Ser Arg Tyr Tyr Val Gln Asn
305                 310                 315                 320

Gly Val Lys Phe Gln Gln Pro Asn Ala Gln Val Gly Ser Tyr Ser Gly
                325                 330                 335

Asn Thr Ile Asn Thr Asp Tyr Cys Ala Ala Glu Gln Thr Ala Phe Gly
                340                 345                 350

Gly Thr Ser Phe Thr Asp Lys Gly Gly Leu Ala Gln Ile Asn Lys Ala
                355                 360                 365

Phe Gln Gly Gly Met Val Leu Val Met Ser Leu Trp Asp Asp Tyr Ala
    370                 375                 380

Val Asn Met Leu Trp Leu Asp Ser Thr Tyr Pro Thr Asn Ala Thr Ala
385                 390                 395                 400

Ser Thr Pro Gly Ala Lys Arg Gly Ser Cys Ser Thr Ser Ser Gly Val
                405                 410                 415

Pro Ala Gln Val Glu Ala Gln Ser Pro Asn Ser Lys Val Ile Tyr Ser
                420                 425                 430

Asn Ile Arg Phe Gly Pro Ile Gly Ser Thr Gly Gly Asn Thr Gly Ser
                435                 440                 445

Asn Pro Pro Gly Thr Ser Thr Thr Arg Ala Pro Ser Ser Thr Gly
    450                 455                 460

Ser Ser Pro Thr Ala Thr Gln Thr His Tyr Gly Gln Cys Gly Gly Thr
465                 470                 475                 480

Gly Trp Thr Gly Pro Thr Arg Cys Ala Ser Gly Tyr Thr Cys Gln Val
                485                 490                 495

Leu Asn Pro Phe Tyr Ser Gln Cys
                500

<210> SEQ ID NO 102
<211> LENGTH: 516
<212> TYPE: PRT
<213> ORGANISM: Phanerochaete chrysosporium

<400> SEQUENCE: 102

Met Phe Arg Thr Ala Thr Leu Leu Ala Phe Thr Met Ala Ala Met Val
1               5                   10                  15

Phe Gly Gln Gln Val Gly Thr Asn Thr Ala Glu Asn His Arg Thr Leu
                20                  25                  30

Thr Ser Gln Lys Cys Thr Lys Ser Gly Gly Cys Ser Asn Leu Asn Thr
                35                  40                  45

Lys Ile Val Leu Asp Ala Asn Trp Arg Trp Leu His Ser Thr Ser Gly
    50                  55                  60

Tyr Thr Asn Cys Tyr Thr Gly Asn Gln Trp Asp Ala Thr Leu Cys Pro
65              70                  75                  80

Asp Gly Lys Thr Cys Ala Ala Asn Cys Ala Leu Asp Gly Ala Asp Tyr
```

```
                 85                  90                  95
Thr Gly Thr Tyr Gly Ile Thr Ala Ser Gly Ser Ser Leu Lys Leu Gln
                100                 105                 110

Phe Val Thr Gly Ser Asn Val Gly Ser Arg Val Tyr Leu Met Ala Asp
                115                 120                 125

Asp Thr His Tyr Gln Met Phe Gln Leu Leu Asn Gln Glu Phe Thr Phe
                130                 135                 140

Asp Val Asp Met Ser Asn Leu Pro Cys Gly Leu Asn Gly Ala Leu Tyr
145                 150                 155                 160

Leu Ser Ala Met Asp Ala Asp Gly Gly Met Ala Lys Tyr Pro Thr Asn
                165                 170                 175

Lys Ala Gly Ala Lys Tyr Gly Thr Gly Tyr Cys Asp Ser Gln Cys Pro
                180                 185                 190

Arg Asp Ile Lys Phe Ile Asn Gly Glu Ala Asn Val Glu Gly Trp Asn
                195                 200                 205

Ala Thr Ser Ala Asn Ala Gly Thr Gly Asn Tyr Gly Thr Cys Cys Thr
                210                 215                 220

Glu Met Asp Ile Trp Glu Ala Asn Asn Asp Ala Ala Ala Tyr Thr Pro
225                 230                 235                 240

His Pro Cys Thr Thr Asn Ala Gln Thr Arg Cys Ser Gly Ser Asp Cys
                245                 250                 255

Thr Arg Asp Thr Gly Leu Cys Asp Ala Asp Gly Cys Asp Phe Asn Ser
                260                 265                 270

Phe Arg Met Gly Asp Gln Thr Phe Leu Gly Lys Gly Leu Thr Val Asp
                275                 280                 285

Thr Ser Lys Pro Phe Thr Val Val Thr Gln Phe Ile Thr Asn Asp Gly
                290                 295                 300

Thr Ser Ala Gly Thr Leu Thr Glu Ile Arg Arg Leu Tyr Val Gln Asn
305                 310                 315                 320

Gly Lys Val Ile Gln Asn Ser Ser Val Lys Ile Pro Gly Ile Asp Pro
                325                 330                 335

Val Asn Ser Ile Thr Asp Asn Phe Cys Ser Gln Gln Lys Thr Ala Phe
                340                 345                 350

Gly Asp Thr Asn Tyr Phe Ala Gln His Gly Gly Leu Lys Gln Val Gly
                355                 360                 365

Glu Ala Leu Arg Thr Gly Met Val Leu Ala Leu Ser Ile Trp Asp Asp
                370                 375                 380

Tyr Ala Ala Asn Met Leu Trp Leu Asp Ser Asn Tyr Pro Thr Asn Lys
385                 390                 395                 400

Asp Pro Ser Thr Pro Gly Val Ala Arg Gly Thr Cys Ala Thr Thr Ser
                405                 410                 415

Gly Val Pro Ala Gln Ile Glu Ala Gln Ser Pro Asn Ala Tyr Val Val
                420                 425                 430

Phe Ser Asn Ile Lys Phe Gly Asp Leu Asn Thr Thr Tyr Thr Gly Thr
                435                 440                 445

Val Ser Ser Ser Ser Val Ser Ser Ser His Ser Ser Thr Ser Thr Ser
                450                 455                 460

Ser Ser His Ser Ser Ser Ser Thr Pro Pro Thr Gln Pro Thr Gly Val
465                 470                 475                 480

Thr Val Pro Gln Trp Gly Gln Cys Gly Gly Ile Gly Tyr Thr Gly Ser
                485                 490                 495

Thr Thr Cys Ala Ser Pro Tyr Thr Cys His Val Leu Asn Pro Tyr Tyr
                500                 505                 510
```

```
Ser Gln Cys Tyr
        515

<210> SEQ ID NO 103
<211> LENGTH: 536
<212> TYPE: PRT
<213> ORGANISM: Volvariella volvacea

<400> SEQUENCE: 103

Met Arg Ala Ser Leu Leu Ala Phe Ser Leu Asn Ser Ala Ala Gly Gln
1               5                   10                  15

Gln Ala Gly Thr Leu Gln Thr Lys Asn His Pro Ser Leu Thr Ser Gln
            20                  25                  30

Lys Cys Arg Gln Gly Gly Cys Pro Gln Val Asn Thr Thr Ile Val Leu
        35                  40                  45

Asp Ala Asn Trp Arg Trp Thr His Ser Thr Ser Gly Ser Thr Asn Cys
    50                  55                  60

Tyr Thr Gly Asn Thr Trp Gln Ala Thr Leu Cys Pro Asp Gly Lys Thr
65                  70                  75                  80

Cys Ala Ala Asn Cys Ala Leu Asp Gly Ala Asp Tyr Thr Gly Thr Tyr
                85                  90                  95

Gly Val Thr Thr Ser Gly Asn Ser Leu Thr Leu Gln Phe Val Thr Gln
            100                 105                 110

Ser Asn Val Gly Ala Arg Leu Gly Tyr Leu Met Ala Asp Asp Thr Thr
        115                 120                 125

Tyr Gln Met Phe Asn Leu Leu Asn Gln Glu Phe Trp Phe Asp Val Asp
    130                 135                 140

Met Ser Asn Leu Pro Cys Gly Leu Asn Gly Ala Leu Tyr Phe Ser Ala
145                 150                 155                 160

Met Ala Arg Thr Ala Ala Trp Met Pro Met Val Val Cys Ala Ser Thr
                165                 170                 175

Pro Leu Ile Ser Thr Arg Arg Ser Thr Ala Arg Leu Leu Arg Leu Pro
            180                 185                 190

Val Pro Pro Arg Ser Arg Tyr Gly Arg Gly Ile Cys Asp Ser Gln Cys
        195                 200                 205

Pro Arg Asp Ile Lys Phe Ile Asn Gly Glu Ala Asn Val Gln Gly Trp
    210                 215                 220

Gln Pro Ser Pro Asn Asp Thr Asn Ala Gly Thr Gly Asn Tyr Gly Ala
225                 230                 235                 240

Cys Cys Asn Lys Met Asp Val Trp Glu Ala Asn Ser Ile Ser Thr Ala
                245                 250                 255

Tyr Thr Pro His Pro Cys Thr Gln Arg Gly Leu Val Arg Cys Ser Gly
            260                 265                 270

Thr Ala Cys Gly Gly Gly Ser Asn Arg Tyr Gly Ser Ile Cys Asp His
        275                 280                 285

Asp Gly Leu Gly Phe Gln Asn Leu Phe Gly Met Gly Arg Thr Arg Val
    290                 295                 300

Arg Ala Arg Val Gly Arg Val Lys Gln Phe Asn Arg Ser Ser Arg Val
305                 310                 315                 320

Val Glu Pro Ile Ser Trp Thr Lys Gln Thr Thr Leu His Leu Gly Asn
                325                 330                 335

Leu Pro Trp Lys Ser Ala Asp Cys Asn Val Gln Asn Gly Arg Val Ile
            340                 345                 350

Gln Asn Ser Lys Val Asn Ile Pro Gly Met Pro Ser Thr Met Asp Ser
        355                 360                 365
```

```
Val Thr Thr Glu Phe Cys Asn Ala Gln Lys Thr Ala Phe Asn Asp Thr
    370                 375                 380

Phe Ser Phe Gln Gln Lys Gly Gly Met Ala Asn Met Ser Glu Ala Leu
385                 390                 395                 400

Arg Arg Gly Met Val Leu Val Leu Ser Ile Trp Asp Asp His Ala Ala
                405                 410                 415

Asn Met Leu Trp Leu Asp Ser Ile Thr Ser Ala Ala Cys Arg Ser
                420                 425                 430

Thr Pro Ser Glu Val His Ala Thr Pro Leu Arg Glu Ser Gln Ile Arg
            435                 440                 445

Ser Ser His Ser Arg Gln Thr Arg Tyr Val Thr Phe Thr Asn Ile Lys
    450                 455                 460

Phe Gly Pro Phe Asn Ser Thr Gly Thr Thr Tyr Thr Thr Gly Ser Val
465                 470                 475                 480

Pro Thr Thr Ser Thr Ser Thr Gly Thr Thr Gly Ser Ser Thr Pro Pro
                485                 490                 495

Gln Pro Thr Gly Val Thr Val Pro Gln Gly Gln Cys Gly Gly Ile Gly
                500                 505                 510

Tyr Thr Gly Pro Thr Thr Cys Ala Ser Pro Thr Thr Cys His Val Leu
            515                 520                 525

Asn Pro Tyr Tyr Ser Gln Cys Tyr
            530                 535

<210> SEQ ID NO 104
<211> LENGTH: 453
<212> TYPE: PRT
<213> ORGANISM: Talaromyces emersonii

<400> SEQUENCE: 104

Met Leu Arg Arg Ala Leu Leu Leu Ser Ser Ser Ala Ile Leu Ala Val
1               5                   10                  15

Lys Ala Gln Gln Ala Gly Thr Ala Thr Ala Glu Asn His Pro Pro Leu
                20                  25                  30

Thr Trp Gln Glu Cys Thr Ala Pro Gly Ser Cys Thr Thr Gln Asn Gly
            35                  40                  45

Ala Val Val Leu Asp Ala Asn Trp Arg Trp Val His Asp Val Asn Gly
        50                  55                  60

Tyr Thr Asn Cys Tyr Thr Gly Asn Thr Trp Asp Pro Thr Tyr Cys Pro
65                  70                  75                  80

Asp Asp Glu Thr Cys Ala Gln Asn Cys Ala Leu Asp Gly Ala Asp Tyr
                85                  90                  95

Glu Gly Thr Tyr Gly Val Thr Ser Ser Gly Ser Ser Leu Lys Leu Asn
            100                 105                 110

Phe Val Thr Gly Ser Asn Val Gly Ser Arg Leu Tyr Leu Leu Gln Asp
        115                 120                 125

Asp Ser Thr Tyr Gln Ile Phe Lys Leu Leu Asn Arg Glu Phe Ser Phe
    130                 135                 140

Asp Val Asp Val Ser Asn Leu Pro Cys Gly Leu Asn Gly Ala Leu Tyr
145                 150                 155                 160

Phe Val Ala Met Asp Ala Asp Gly Gly Val Ser Lys Tyr Pro Asn Asn
                165                 170                 175

Lys Ala Gly Ala Lys Tyr Gly Thr Gly Tyr Cys Asp Ser Gln Cys Pro
            180                 185                 190

Arg Asp Leu Lys Phe Ile Asp Gly Glu Ala Asn Val Glu Gly Trp Gln
        195                 200                 205
```

Pro Ser Ser Asn Asn Ala Asn Thr Gly Ile Gly Asp His Gly Ser Cys
    210                 215                 220

Cys Ala Glu Met Asp Val Trp Glu Ala Asn Ser Ile Ser Asn Ala Val
225                 230                 235                 240

Thr Pro His Pro Cys Asp Thr Pro Gly Gln Thr Met Cys Ser Gly Asp
                245                 250                 255

Asp Cys Gly Gly Thr Tyr Ser Asn Asp Arg Tyr Ala Gly Thr Cys Asp
            260                 265                 270

Pro Asp Gly Cys Asp Phe Asn Pro Tyr Arg Met Gly Asn Thr Ser Phe
        275                 280                 285

Tyr Gly Pro Gly Lys Ile Ile Asp Thr Thr Lys Pro Phe Thr Val Val
    290                 295                 300

Thr Gln Phe Leu Thr Asp Asp Gly Thr Asp Thr Gly Thr Leu Ser Glu
305                 310                 315                 320

Ile Lys Arg Phe Tyr Ile Gln Asn Ser Asn Val Ile Pro Gln Pro Asn
                325                 330                 335

Ser Asp Ile Ser Gly Val Thr Gly Asn Ser Ile Thr Thr Glu Phe Cys
            340                 345                 350

Thr Ala Gln Lys Gln Ala Phe Gly Asp Thr Asp Phe Ser Gln His
        355                 360                 365

Gly Gly Leu Ala Lys Met Gly Ala Ala Met Gln Gln Gly Met Val Leu
    370                 375                 380

Val Met Ser Leu Trp Asp Asp Tyr Ala Ala Gln Met Leu Trp Leu Asp
385                 390                 395                 400

Ser Asp Tyr Pro Thr Asp Ala Asp Pro Thr Thr Pro Gly Ile Ala Arg
                405                 410                 415

Gly Thr Cys Pro Thr Asp Ser Gly Val Pro Ser Asp Val Glu Ser Gln
            420                 425                 430

Ser Pro Asn Ser Tyr Val Thr Tyr Ser Asn Ile Lys Phe Gly Pro Ile
        435                 440                 445

Asn Ser Thr Phe Thr
    450

<210> SEQ ID NO 105
<211> LENGTH: 537
<212> TYPE: PRT
<213> ORGANISM: Penicillium janthinellum
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 105

Met Lys Gly Ser Ile Ser Tyr Gln Ile Tyr Lys Gly Ala Leu Leu Leu
1               5                   10                  15

Ser Ala Leu Leu Asn Ser Val Ser Ala Gln Gln Val Gly Thr Leu Thr
            20                  25                  30

Ala Glu Thr His Pro Ala Leu Thr Trp Ser Lys Cys Thr Ala Gly Xaa
        35                  40                  45

Cys Ser Gln Val Ser Gly Ser Val Val Ile Asp Ala Asn Trp Pro Xaa
    50                  55                  60

Val His Ser Thr Ser Gly Ser Thr Asn Cys Tyr Thr Gly Asn Thr Trp
65                  70                  75                  80

Asp Ala Thr Leu Cys Pro Asp Asp Val Thr Cys Ala Ala Asn Cys Ala

```
                    85                  90                  95
Val Asp Gly Ala Arg Arg Gln His Leu Arg Val Thr Thr Ser Gly Asn
                100                 105                 110

Ser Leu Arg Ile Asn Phe Val Thr Thr Ala Ser Gln Lys Asn Ile Gly
            115                 120                 125

Ser Arg Leu Tyr Leu Leu Glu Asn Asp Thr Thr Tyr Gln Lys Phe Asn
        130                 135                 140

Leu Leu Asn Gln Glu Phe Thr Phe Asp Val Asp Val Ser Asn Leu Pro
145                 150                 155                 160

Cys Gly Leu Asn Gly Ala Leu Tyr Phe Val Asp Met Asp Ala Asp Gly
                165                 170                 175

Gly Met Ala Lys Tyr Pro Thr Asn Lys Ala Gly Ala Lys Tyr Gly Thr
                180                 185                 190

Gly Tyr Cys Asp Ser Gln Cys Pro Arg Asp Leu Lys Phe Ile Asn Gly
            195                 200                 205

Gln Ala Asn Val Asp Gly Trp Thr Pro Ser Lys Asn Asp Val Asn Ser
        210                 215                 220

Gly Ile Gly Asn His Gly Ser Cys Cys Ala Glu Met Asp Ile Trp Glu
225                 230                 235                 240

Ala Asn Ser Ile Ser Asn Ala Val Thr Pro His Pro Cys Asp Thr Pro
                245                 250                 255

Ser Gln Thr Met Cys Thr Gly Gln Arg Cys Gly Gly Thr Tyr Ser Thr
                260                 265                 270

Asp Arg Tyr Gly Gly Thr Cys Asp Pro Asp Gly Cys Asp Phe Asn Pro
            275                 280                 285

Tyr Arg Met Gly Val Thr Asn Phe Tyr Gly Pro Gly Glu Thr Ile Asp
        290                 295                 300

Thr Lys Ser Pro Phe Thr Val Val Thr Gln Phe Leu Thr Asn Asp Gly
305                 310                 315                 320

Thr Ser Thr Gly Thr Leu Ser Glu Ile Lys Arg Phe Tyr Val Gln Gly
                325                 330                 335

Gly Lys Val Ile Gly Asn Pro Gln Ser Thr Ile Val Gly Val Ser Gly
                340                 345                 350

Asn Ser Ile Thr Asp Ser Trp Cys Asn Ala Gln Lys Ser Ala Phe Gly
            355                 360                 365

Asp Thr Asn Glu Phe Ser Lys His Gly Gly Met Ala Gly Met Gly Ala
        370                 375                 380

Gly Leu Ala Asp Gly Met Val Leu Val Met Ser Leu Trp Asp Asp His
385                 390                 395                 400

Ala Ser Asp Met Leu Trp Leu Asp Ser Thr Tyr Pro Thr Asn Ala Thr
                405                 410                 415

Ser Thr Thr Pro Gly Ala Lys Arg Gly Thr Cys Asp Ile Ser Arg Arg
                420                 425                 430

Pro Asn Thr Val Glu Ser Thr Tyr Pro Asn Ala Tyr Val Ile Tyr Ser
            435                 440                 445

Asn Ile Lys Thr Gly Pro Leu Asn Ser Thr Phe Thr Gly Gly Thr Thr
        450                 455                 460

Ser Ser Ser Ser Thr Thr Thr Thr Ser Lys Ser Thr Ser Thr Ser Ser
465                 470                 475                 480

Ser Ser Ser Lys Thr Thr Thr Val Thr Thr Thr Thr Ser Ser
                485                 490                 495

Gly Ser Ser Gly Thr Gly Ala Arg Asp Trp Ala Gln Cys Gly Gly Asn
                500                 505                 510
```

Gly Trp Thr Gly Pro Thr Thr Cys Val Ser Pro Tyr Thr Cys Thr Lys
            515                 520                 525

Gln Asn Asp Trp Tyr Ser Gln Cys Leu
    530                 535

<210> SEQ ID NO 106
<211> LENGTH: 430
<212> TYPE: PRT
<213> ORGANISM: Aspergillus nidulans

<400> SEQUENCE: 106

Met Ala Leu Leu Leu Ser Leu Ser Leu Leu Ala Thr Thr Ile Ser Ala
1               5                   10                  15

Gln Gln Ile Gly Thr Pro Glu Ile Arg Pro Arg Leu Thr Thr Tyr His
            20                  25                  30

Cys Thr Ser Ala Asn Gly Cys Thr Glu Gln Asn Thr Ser Val Val Leu
        35                  40                  45

Asp Ala Ala Thr His Pro Ile His Asp Ala Ser Asn Pro Ser Val Ser
    50                  55                  60

Cys Thr Thr Ser Asn Gly Leu Asn Pro Ala Leu Cys Pro Asp Lys Gln
65                  70                  75                  80

Thr Cys Ala Asp Asn Cys Val Ile Asp Gly Ile Thr Asp Tyr Ala Ala
                85                  90                  95

His Gly Val Glu Thr His Gly Ser Arg Leu Thr Leu Thr Gln Tyr Arg
            100                 105                 110

Asn Val Asn Gly Ala Leu Ser Ser Val Ser Pro Arg Val Tyr Leu Val
        115                 120                 125

Asp Glu Ser Asp Pro Asp Glu Gln Glu Tyr Arg Ala Leu Ser Leu Leu
    130                 135                 140

Ala Gln Glu Phe Thr Phe Thr Val Asn Val Ser Ala Leu Pro Cys Gly
145                 150                 155                 160

Met Asn Gly Ala Leu Tyr Leu Ser Glu Met Ser Pro Ser Gly Gly Arg
                165                 170                 175

Ser Ala Leu Asn Pro Ala Gly Ala Ser Tyr Gly Thr Gly Tyr Cys Asp
            180                 185                 190

Ala Gln Cys Tyr Val Asn Pro Trp Ile Asn Gly Glu Gly Asn Ile Asn
        195                 200                 205

Gly Tyr Gly Ala Cys Cys Asn Glu Met Asp Ile Trp Glu Ala Asn Ser
    210                 215                 220

Arg Ser Thr Gly Phe Thr Pro His Ala Cys Leu Tyr Glu Pro Glu Glu
225                 230                 235                 240

Thr Glu Gly Arg Gly Val Tyr Glu Cys Ala Ser Glu Asp Glu Cys Asp
                245                 250                 255

Ser Ala Gly Glu Asn Asp Gly Ile Cys Asp Lys Trp Gly Cys Gly Phe
            260                 265                 270

Asn Pro Tyr Ala Leu Gly Asn Thr Glu Tyr Tyr Gly Arg Gly Gln Gly
        275                 280                 285

Phe Glu Val Asp Thr Lys Glu Pro Phe Thr Val Thr Gln Phe Leu
    290                 295                 300

Thr Asp Asp Gly Thr Ser Thr Gly Ala Leu Thr Glu Ile Arg Arg Leu
305                 310                 315                 320

Tyr Ile Gln Asn Gly Gln Val Ile Glu Asn Ala Val Val Ser Ser Gly
                325                 330                 335

Ala Asp Ser Leu Thr Asp Ser Leu Cys Ala Ser Thr Ala Ser Trp Phe
            340                 345                 350

```
Asp Ser Tyr Gly Gly Met Glu Gly Met Gly Arg Ala Leu Gly Arg Gly
        355                 360                 365

Met Val Leu Ala Met Ser Ile Trp Asn Asp Ala Gly Gly Tyr Met Gln
370                 375                 380

Trp Leu Asp Gly Asp Ala Gly Pro Cys Asn Ala Thr Glu Gly Ala
385                 390                 395                 400

Pro Glu Phe Ile Glu Glu His Thr Pro Trp Thr Arg Val Val Phe Glu
                405                 410                 415

Asp Leu Lys Trp Gly Asp Ile Gly Ser Thr Phe Gln Ala Ser
                420                 425                 430

<210> SEQ ID NO 107
<211> LENGTH: 529
<212> TYPE: PRT
<213> ORGANISM: Penicillium funiculosum

<400> SEQUENCE: 107

Met Ser Ala Leu Asn Ser Phe Asn Met Tyr Lys Ser Ala Leu Ile Leu
1               5                   10                  15

Gly Ser Leu Leu Ala Thr Ala Gly Ala Gln Gln Ile Gly Thr Tyr Thr
            20                  25                  30

Ala Glu Thr His Pro Ser Leu Ser Trp Ser Thr Cys Lys Ser Gly Gly
        35                  40                  45

Ser Cys Thr Thr Asn Ser Gly Ala Ile Thr Leu Asp Ala Asn Trp Arg
    50                  55                  60

Trp Val His Gly Val Asn Thr Ser Thr Asn Cys Tyr Thr Gly Asn Thr
65                  70                  75                  80

Trp Asn Thr Ala Ile Cys Asp Thr Asp Ala Ser Cys Ala Gln Asp Cys
                85                  90                  95

Ala Leu Asp Gly Ala Asp Tyr Ser Gly Thr Tyr Gly Ile Thr Thr Ser
            100                 105                 110

Gly Asn Ser Leu Arg Leu Asn Phe Val Thr Gly Ser Asn Val Gly Ser
        115                 120                 125

Arg Thr Tyr Leu Met Ala Asp Asn Thr His Tyr Gln Ile Phe Asp Leu
    130                 135                 140

Leu Asn Gln Glu Phe Thr Phe Thr Val Asp Val Ser Asn Leu Pro Cys
145                 150                 155                 160

Gly Leu Asn Gly Ala Leu Tyr Phe Val Thr Met Asp Ala Asp Gly Gly
                165                 170                 175

Val Ser Lys Tyr Pro Asn Asn Lys Ala Gly Ala Gln Tyr Gly Val Gly
            180                 185                 190

Tyr Cys Asp Ser Gln Cys Pro Arg Asp Leu Lys Phe Ile Ala Gly Gln
        195                 200                 205

Ala Asn Val Glu Gly Trp Thr Pro Ser Thr Asn Asn Ser Asn Thr Gly
    210                 215                 220

Ile Gly Asn His Gly Ser Cys Cys Ala Glu Leu Asp Ile Trp Glu Ala
225                 230                 235                 240

Asn Ser Ile Ser Glu Ala Leu Thr Pro His Pro Cys Asp Thr Pro Gly
                245                 250                 255

Leu Thr Val Cys Thr Ala Asp Asp Cys Gly Gly Thr Tyr Ser Ser Asn
            260                 265                 270

Arg Tyr Ala Gly Thr Cys Asp Pro Asp Gly Cys Asp Phe Asn Pro Tyr
        275                 280                 285

Arg Leu Gly Val Thr Asp Phe Tyr Gly Ser Gly Lys Thr Val Asp Thr
    290                 295                 300
```

```
Thr Lys Pro Phe Thr Val Val Thr Gln Phe Val Thr Asp Asp Gly Thr
305                 310                 315                 320

Ser Ser Gly Ser Leu Ser Glu Ile Arg Arg Tyr Tyr Val Gln Asn Gly
            325                 330                 335

Val Val Ile Pro Gln Pro Ser Ser Lys Ile Ser Gly Ile Ser Gly Asn
        340                 345                 350

Val Ile Asn Ser Asp Phe Cys Ala Ala Glu Leu Ser Ala Phe Gly Glu
    355                 360                 365

Thr Ala Ser Phe Thr Asn His Gly Gly Leu Lys Asn Met Gly Ser Ala
370                 375                 380

Leu Glu Ala Gly Met Val Leu Val Met Ser Leu Trp Asp Asp Tyr Ser
385                 390                 395                 400

Val Asn Met Leu Trp Leu Asp Ser Thr Tyr Pro Ala Asn Glu Thr Gly
                405                 410                 415

Thr Pro Gly Ala Ala Arg Gly Ser Cys Pro Thr Thr Ser Gly Asn Pro
            420                 425                 430

Lys Thr Val Glu Ser Gln Ser Gly Ser Ser Tyr Val Val Phe Ser Asp
        435                 440                 445

Ile Lys Val Gly Pro Phe Asn Ser Thr Phe Ser Gly Gly Thr Ser Thr
    450                 455                 460

Gly Gly Ser Thr Thr Thr Thr Ala Ser Gly Thr Thr Ser Thr Lys Ala
465                 470                 475                 480

Ser Thr Thr Ser Thr Ser Ser Thr Ser Thr Gly Thr Gly Val Ala Ala
                485                 490                 495

His Trp Gly Gln Cys Gly Gly Gln Gly Trp Thr Gly Pro Thr Thr Cys
            500                 505                 510

Ala Ser Gly Thr Thr Cys Thr Val Val Asn Pro Tyr Tyr Ser Gln Cys
        515                 520                 525

Leu

<210> SEQ ID NO 108
<211> LENGTH: 538
<212> TYPE: PRT
<213> ORGANISM: Thielavia australiensis

<400> SEQUENCE: 108

Met Tyr Ala Lys Phe Ala Thr Leu Ala Ala Leu Val Ala Gly Ala Ser
1               5                   10                  15

Ala Gln Ala Val Cys Ser Leu Thr Ala Glu Thr His Pro Ser Leu Thr
            20                  25                  30

Trp Gln Lys Cys Thr Ala Pro Gly Ser Cys Thr Asn Val Ala Gly Ser
        35                  40                  45

Ile Thr Ile Asp Ala Asn Trp Arg Trp Thr His Gln Thr Ser Ser Ala
    50                  55                  60

Thr Asn Cys Tyr Ser Gly Ser Lys Trp Asp Ser Ser Ile Cys Thr Thr
65                  70                  75                  80

Gly Thr Asp Cys Ala Ser Lys Cys Cys Ile Asp Gly Ala Glu Tyr Ser
                85                  90                  95

Ser Thr Tyr Gly Ile Thr Thr Ser Gly Asn Ala Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Lys Leu Leu Gly Asn Glu
    130                 135                 140

Phe Thr Phe Asp Val Asp Val Ser Asn Leu Gly Cys Gly Leu Asn Gly
```

```
                145                 150                 155                 160
Ala Leu Tyr Phe Val Ser Met Asp Ala Asp Gly Gly Met Ser Lys Tyr
                    165                 170                 175

Ser Gly Asn Lys Ala Gly Ala Lys Tyr Gly Thr Gly Tyr Cys Asp Ala
                    180                 185                 190

Gln Cys Pro Arg Asp Leu Lys Phe Ile Asn Gly Glu Ala Asn Val Glu
                    195                 200                 205

Gly Trp Glu Ser Ser Thr Asn Asp Ala Asn Ala Gly Ser Gly Lys Tyr
                    210                 215                 220

Gly Ser Cys Cys Thr Glu Met Asp Val Trp Glu Ala Asn Asn Met Ala
225                 230                 235                 240

Thr Ala Phe Thr Pro His Pro Cys Thr Thr Ile Gly Gln Thr Arg Cys
                    245                 250                 255

Glu Gly Asp Thr Cys Gly Gly Thr Tyr Ser Ser Asp Arg Tyr Ala Gly
                    260                 265                 270

Val Cys Asp Pro Asp Gly Cys Asp Phe Asn Ser Tyr Arg Gln Gly Asn
                    275                 280                 285

Lys Thr Phe Tyr Gly Lys Gly Met Thr Val Asp Thr Thr Lys Lys Ile
            290                 295                 300

Thr Val Val Thr Gln Phe Leu Lys Asn Ser Ala Gly Glu Leu Ser Glu
305                 310                 315                 320

Ile Lys Arg Phe Tyr Ala Gln Asp Gly Lys Val Ile Pro Asn Ser Glu
                    325                 330                 335

Ser Thr Ile Ala Gly Ile Pro Gly Asn Ser Ile Thr Lys Ala Tyr Cys
                    340                 345                 350

Asp Ala Gln Lys Thr Val Phe Gln Asn Thr Asp Asp Phe Thr Ala Lys
                    355                 360                 365

Gly Gly Leu Val Gln Met Gly Lys Ala Leu Ala Gly Asp Met Val Leu
                    370                 375                 380

Val Met Ser Val Trp Asp Asp His Ala Val Asn Met Leu Trp Leu Asp
385                 390                 395                 400

Ser Thr Tyr Pro Thr Asp Gln Val Gly Val Ala Gly Ala Glu Arg Gly
                    405                 410                 415

Ala Cys Pro Thr Thr Ser Gly Val Pro Ser Asp Val Glu Ala Asn Ala
                    420                 425                 430

Pro Asn Ser Asn Val Ile Phe Ser Asn Ile Arg Phe Gly Pro Ile Gly
                    435                 440                 445

Ser Thr Val Gln Gly Leu Pro Ser Ser Gly Thr Ser Ser Ser Ser
                    450                 455                 460

Ser Ala Ala Pro Gln Ser Thr Ser Thr Lys Ala Ser Thr Thr Thr Ser
465                 470                 475                 480

Ala Val Arg Thr Thr Ser Thr Ala Thr Thr Lys Thr Thr Ser Ser Ala
                    485                 490                 495

Pro Ala Gln Gly Thr Asn Thr Ala Lys His Trp Gln Gln Cys Gly Gly
                    500                 505                 510

Asn Gly Trp Thr Gly Pro Thr Val Cys Glu Ser Pro Tyr Lys Cys Thr
                    515                 520                 525

Lys Gln Asn Asp Trp Tyr Ser Gln Cys Leu
            530                 535

<210> SEQ ID NO 109
<211> LENGTH: 526
<212> TYPE: PRT
<213> ORGANISM: Chrysosporium lucknowense
<220> FEATURE:
```

```
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid

<400> SEQUENCE: 109
```

| | | | | | | | | | | | | | | |
|---|---|---|---|---|---|---|---|---|---|---|---|---|---|---|
| Met | Tyr | Ala | Lys | Phe | Ala | Thr | Leu | Ala | Ala | Leu | Val | Ala | Gly | Ala | Ala |
| 1 | | | | 5 | | | | | 10 | | | | | 15 | |
| Ala | Gln | Asn | Ala | Cys | Thr | Leu | Thr | Ala | Glu | Asn | His | Pro | Ser | Leu | Thr |
| | | | 20 | | | | | 25 | | | | | 30 | | |
| Trp | Ser | Lys | Cys | Thr | Ser | Gly | Gly | Ser | Cys | Thr | Ser | Val | Gln | Gly | Ser |
| | | 35 | | | | | 40 | | | | | 45 | | | |
| Ile | Thr | Ile | Asp | Ala | Asn | Trp | Arg | Trp | Thr | His | Arg | Thr | Asp | Ser | Ala |
| | 50 | | | | | 55 | | | | | 60 | | | | |
| Thr | Asn | Cys | Tyr | Glu | Gly | Asn | Lys | Trp | Asp | Thr | Ser | Tyr | Cys | Ser | Asp |
| 65 | | | | | 70 | | | | | 75 | | | | | 80 |
| Gly | Pro | Ser | Cys | Ala | Ser | Lys | Cys | Cys | Ile | Asp | Gly | Ala | Asp | Tyr | Ser |
| | | | | 85 | | | | | 90 | | | | | 95 | |
| Ser | Thr | Tyr | Gly | Ile | Thr | Thr | Ser | Gly | Asn | Ser | Leu | Asn | Leu | Lys | Phe |
| | | | 100 | | | | | 105 | | | | | 110 | | |
| Val | Thr | Lys | Gly | Gln | Tyr | Ser | Thr | Asn | Ile | Gly | Ser | Arg | Thr | Tyr | Leu |
| | | 115 | | | | | 120 | | | | | 125 | | | |
| Met | Glu | Ser | Asp | Thr | Lys | Tyr | Gln | Met | Phe | Gln | Leu | Leu | Gly | Asn | Glu |
| | 130 | | | | | 135 | | | | | 140 | | | | |
| Phe | Thr | Phe | Asp | Val | Asp | Val | Ser | Asn | Leu | Gly | Cys | Gly | Leu | Asn | Gly |
| 145 | | | | | 150 | | | | | 155 | | | | | 160 |
| Ala | Leu | Tyr | Phe | Val | Ser | Met | Asp | Ala | Asp | Gly | Gly | Met | Ser | Lys | Tyr |
| | | | | 165 | | | | | 170 | | | | | 175 | |
| Ser | Gly | Asn | Lys | Ala | Gly | Ala | Lys | Tyr | Gly | Thr | Gly | Tyr | Cys | Asp | Ser |
| | | | 180 | | | | | 185 | | | | | 190 | | |
| Gln | Cys | Pro | Arg | Asp | Leu | Lys | Phe | Ile | Asn | Gly | Glu | Ala | Asn | Val | Glu |
| | | 195 | | | | | 200 | | | | | 205 | | | |
| Asn | Trp | Gln | Ser | Ser | Thr | Asn | Asp | Ala | Asn | Ala | Gly | Thr | Gly | Lys | Tyr |
| | 210 | | | | | 215 | | | | | 220 | | | | |
| Gly | Ser | Cys | Cys | Ser | Glu | Met | Asp | Val | Trp | Glu | Ala | Asn | Asn | Met | Ala |
| 225 | | | | | 230 | | | | | 235 | | | | | 240 |
| Ala | Ala | Phe | Thr | Pro | His | Pro | Cys | Xaa | Val | Ile | Gly | Gln | Ser | Arg | Cys |
| | | | | 245 | | | | | 250 | | | | | 255 | |
| Glu | Gly | Asp | Ser | Cys | Gly | Gly | Thr | Tyr | Ser | Thr | Asp | Arg | Tyr | Ala | Gly |
| | | | 260 | | | | | 265 | | | | | 270 | | |
| Ile | Cys | Asp | Pro | Asp | Gly | Cys | Asp | Phe | Asn | Ser | Tyr | Arg | Gln | Gly | Asn |
| | | 275 | | | | | 280 | | | | | 285 | | | |
| Lys | Thr | Phe | Tyr | Gly | Lys | Gly | Met | Thr | Val | Asp | Thr | Thr | Lys | Lys | Ile |
| | 290 | | | | | 295 | | | | | 300 | | | | |
| Thr | Val | Val | Thr | Gln | Phe | Leu | Lys | Asn | Ser | Ala | Gly | Glu | Leu | Ser | Glu |
| 305 | | | | | 310 | | | | | 315 | | | | | 320 |
| Ile | Lys | Arg | Phe | Tyr | Val | Gln | Asn | Gly | Lys | Val | Ile | Pro | Asn | Ser | Glu |
| | | | | 325 | | | | | 330 | | | | | 335 | |
| Ser | Thr | Ile | Pro | Gly | Val | Glu | Gly | Asn | Ser | Ile | Thr | Gln | Asp | Trp | Cys |
| | | | 340 | | | | | 345 | | | | | 350 | | |
| Asp | Arg | Gln | Lys | Ala | Ala | Phe | Gly | Asp | Val | Thr | Asp | Xaa | Gln | Asp | Lys |
| | | 355 | | | | | 360 | | | | | 365 | | | |
| Gly | Gly | Met | Val | Gln | Met | Gly | Lys | Ala | Leu | Ala | Gly | Pro | Met | Val | Leu |

```
                        370                 375                 380
Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
            435                 440                 445

Ser Thr Val Ser Gly Leu Pro Asp Gly Ser Gly Asn Pro Asn Pro
        450                 455                 460

Pro Val Ser Ser Thr Pro Val Pro Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
                500                 505                 510

Tyr Thr Cys Thr Lys Leu Asn Asp Trp Tyr Ser Gln Cys Leu
            515                 520                 525

<210> SEQ ID NO 110
<211> LENGTH: 528
<212> TYPE: PRT
<213> ORGANISM: Penicillium funiculosum

<400> SEQUENCE: 110

Met Ala Leu Asn Ser Phe Asn Met Tyr Lys Ser Ala Leu Leu Leu Gly
1               5                   10                  15

Ser Leu Leu Ala Thr Ala Gly Ala Gln Gln Ile Gly Thr Tyr Thr Ala
            20                  25                  30

Glu Thr His Pro Ser Leu Ser Trp Ser Thr Cys Lys Ser Gly Gly Ser
        35                  40                  45

Cys Thr Thr Asn Ser Gly Ala Ile Thr Leu Asp Ala Asn Trp Arg Trp
    50                  55                  60

Val His Gly Val Asn Thr Ser Thr Asn Cys Tyr Thr Gly Asn Thr Trp
65                  70                  75                  80

Asn Ser Ala Ile Cys Asp Thr Asp Ala Ser Cys Ala Gln Asp Cys Ala
                85                  90                  95

Leu Asp Gly Ala Asp Tyr Ser Gly Thr Tyr Gly Ile Thr Thr Ser Gly
            100                 105                 110

Asn Ser Leu Arg Leu Asn Phe Val Thr Gly Ser Asn Val Gly Ser Arg
        115                 120                 125

Thr Tyr Leu Met Ala Asp Asn Thr His Tyr Gln Ile Phe Asp Leu Leu
    130                 135                 140

Asn Gln Glu Phe Thr Phe Thr Val Asp Val Ser His Leu Pro Cys Gly
145                 150                 155                 160

Leu Asn Gly Ala Leu Tyr Phe Val Thr Met Asp Ala Asp Gly Gly Val
                165                 170                 175

Ser Lys Tyr Pro Asn Asn Lys Ala Gly Ala Gln Tyr Gly Val Gly Tyr
            180                 185                 190

Cys Asp Ser Gln Cys Pro Arg Asp Leu Lys Phe Ile Ala Gly Gln Ala
        195                 200                 205

Asn Val Glu Gly Trp Thr Pro Ser Ala Asn Asn Ala Asn Thr Gly Ile
    210                 215                 220

Gly Asn His Gly Ala Cys Cys Ala Glu Leu Asp Ile Trp Glu Ala Asn
```

```
                225                 230                 235                 240
Ser Ile Ser Glu Ala Leu Thr Pro His Pro Cys Asp Thr Pro Gly Leu
                245                 250                 255

Ser Val Cys Thr Thr Asp Ala Cys Gly Gly Thr Tyr Ser Ser Asp Arg
                260                 265                 270

Tyr Ala Gly Thr Cys Asp Pro Asp Gly Cys Asp Phe Asn Pro Tyr Arg
                275                 280                 285

Leu Gly Val Thr Asp Phe Tyr Gly Ser Gly Lys Thr Val Asp Thr Thr
                290                 295                 300

Lys Pro Phe Thr Val Val Thr Gln Phe Val Thr Asn Asp Gly Thr Ser
305                 310                 315                 320

Thr Gly Ser Leu Ser Glu Ile Arg Arg Tyr Tyr Val Gln Asn Gly Val
                325                 330                 335

Val Ile Pro Gln Pro Ser Ser Lys Ile Ser Gly Ile Ser Gly Asn Val
                340                 345                 350

Ile Asn Ser Asp Tyr Cys Ala Ala Glu Ile Ser Thr Phe Gly Gly Thr
                355                 360                 365

Ala Ser Phe Ser Lys His Gly Gly Leu Thr Asn Met Ala Ala Gly Met
                370                 375                 380

Glu Ala Gly Met Val Leu Val Met Ser Leu Trp Asp Asp Tyr Ala Val
385                 390                 395                 400

Asn Met Leu Trp Leu Asp Ser Thr Tyr Pro Thr Asn Ala Thr Gly Thr
                405                 410                 415

Pro Gly Ala Ala Arg Gly Thr Cys Ala Thr Thr Ser Gly Asp Pro Lys
                420                 425                 430

Thr Val Glu Ser Gln Ser Gly Ser Ser Tyr Val Thr Phe Ser Asp Ile
                435                 440                 445

Arg Val Gly Pro Phe Asn Ser Thr Phe Ser Gly Gly Ser Ser Thr Gly
                450                 455                 460

Gly Ser Thr Thr Thr Thr Ala Ser Arg Thr Thr Thr Thr Ser Ala Ser
465                 470                 475                 480

Ser Thr Ser Thr Ser Ser Thr Ser Thr Gly Thr Gly Val Ala Gly His
                485                 490                 495

Trp Gly Gln Cys Gly Gly Gln Gly Trp Thr Gly Pro Thr Thr Cys Val
                500                 505                 510

Ser Gly Thr Thr Cys Thr Val Val Asn Pro Tyr Tyr Ser Gln Cys Leu
                515                 520                 525

<210> SEQ ID NO 111
<211> LENGTH: 514
<212> TYPE: PRT
<213> ORGANISM: Trichoderma reesei

<400> SEQUENCE: 111

Met Tyr Arg Lys Leu Ala Val Ile Ser Ala Phe Leu Ala Thr Ala Arg
1               5                   10                  15

Ala Gln Ser Ala Cys Thr Leu Gln Ser Glu Thr His Pro Pro Leu Thr
                20                  25                  30

Trp Gln Lys Cys Ser Ser Gly Gly Thr Cys Thr Gln Gln Thr Gly Ser
                35                  40                  45

Val Val Ile Asp Ala Asn Trp Arg Trp Thr His Ala Thr Asn Ser Ser
                50                  55                  60

Thr Asn Cys Tyr Asp Gly Asn Thr Trp Ser Ser Thr Leu Cys Pro Asp
65                  70                  75                  80

Asn Glu Thr Cys Ala Lys Asn Cys Cys Leu Asp Gly Ala Ala Tyr Ala
```

```
                85                  90                  95
Ser Thr Tyr Gly Val Thr Thr Ser Gly Asn Ser Leu Ser Ile Gly Phe
                100                 105                 110

Val Thr Gln Ser Ala Gln Lys Asn Val Gly Ala Arg Leu Tyr Leu Met
                115                 120                 125

Ala Ser Asp Thr Thr Tyr Gln Glu Phe Thr Leu Leu Gly Asn Glu Phe
                130                 135                 140

Ser Phe Asp Val Asp Val Ser Gln Leu Pro Cys Gly Leu Asn Gly Ala
145                 150                 155                 160

Leu Tyr Phe Val Ser Met Asp Ala Asp Gly Gly Val Ser Lys Tyr Pro
                165                 170                 175

Thr Asn Thr Ala Gly Ala Lys Tyr Gly Thr Gly Tyr Cys Asp Ser Gln
                180                 185                 190

Cys Pro Arg Asp Leu Lys Phe Ile Asn Gly Gln Ala Asn Val Glu Gly
                195                 200                 205

Trp Glu Pro Ser Ser Asn Asn Ala Asn Thr Gly Ile Gly Gly His Gly
                210                 215                 220

Ser Cys Cys Ser Glu Met Asp Ile Trp Glu Ala Asn Ser Ile Ser Glu
225                 230                 235                 240

Ala Leu Thr Pro His Pro Cys Thr Thr Val Gly Gln Glu Ile Cys Glu
                245                 250                 255

Gly Asp Gly Cys Gly Gly Thr Tyr Ser Asp Asn Arg Tyr Gly Gly Thr
                260                 265                 270

Cys Asp Pro Asp Gly Cys Asp Trp Asn Pro Tyr Arg Leu Gly Asn Thr
                275                 280                 285

Ser Phe Tyr Gly Pro Gly Ser Ser Phe Thr Leu Asp Thr Thr Lys Lys
                290                 295                 300

Leu Thr Val Val Thr Gln Phe Glu Thr Ser Gly Ala Ile Asn Arg Tyr
305                 310                 315                 320

Tyr Val Gln Asn Gly Val Thr Phe Gln Gln Pro Asn Ala Glu Leu Gly
                325                 330                 335

Ser Tyr Ser Gly Asn Glu Leu Asn Asp Asp Tyr Cys Thr Ala Glu Glu
                340                 345                 350

Ala Glu Phe Gly Gly Ser Ser Phe Ser Asp Lys Gly Gly Leu Thr Gln
                355                 360                 365

Phe Lys Lys Ala Thr Ser Gly Gly Met Val Leu Val Met Ser Leu Trp
                370                 375                 380

Asp Asp Tyr Tyr Ala Asn Met Leu Trp Leu Asp Ser Thr Tyr Pro Thr
385                 390                 395                 400

Asn Glu Thr Ser Ser Thr Pro Gly Ala Val Arg Gly Ser Cys Ser Thr
                405                 410                 415

Ser Ser Gly Val Pro Ala Gln Val Glu Ser Gln Ser Pro Asn Ala Lys
                420                 425                 430

Val Thr Phe Ser Asn Ile Lys Phe Gly Pro Ile Gly Ser Thr Gly Asn
                435                 440                 445

Pro Ser Gly Gly Asn Pro Gly Gly Asn Pro Gly Thr Thr Thr
                450                 455                 460

Thr Arg Arg Pro Ala Thr Thr Thr Gly Ser Ser Pro Gly Pro Thr Gln
465                 470                 475                 480

Ser His Tyr Gly Gln Cys Gly Gly Ile Gly Tyr Ser Gly Pro Thr Val
                485                 490                 495
```

```
Cys Ala Ser Gly Thr Thr Cys Gln Val Leu Asn Pro Tyr Tyr Ser Gln
            500                 505                 510

Cys Leu
```

CELLOBIOHYDROLASE I ENZYMES

CROSS REFERENCES

The present application is a continuation-in-part of U.S. patent application Ser. No. 10/031,496 filed Jan. 14, 2002 (now U.S. Pat. No. 7,375,197, issued May 20, 2008), which is a continuation of PCT Application No. PCT/US00/19007 filed Jul. 13, 2000, which claims priority to U.S. Provisional Application No. 60/143,711 filed Jul. 13, 1999. Each of these applications is incorporated by reference in its entirety as though fully set forth herein.

The United States Government has rights in this invention under Contract No. DE-AC36-99GO10337 between the United States Department of Energy and the National Renewable Energy Laboratory, a division of the Midwest Research Institute.

BACKGROUND

The surface chemistry of acid pretreated-biomass, used in ethanol production, is different from that found in plant tissues, naturally digested by fungal cellulase enzymes, in two important ways: (1) pretreatment heats the substrate past the phase-transition temperature of lignin; and (2) pretreated biomass contains less acetylated hemicellulose. Thus, it is believed, that the cellulose fibers of pretreated-biomass are coated with displaced and modified lignin. This alteration results in a non-specific binding of the protein with the biomass, which impedes enzymatic activity. Therefore, for the efficient production of ethanol from a pretreated biomass such as corn stover, wood or other biomass it is desirable to enhance the catalytic activity of glycosyl hydrolases and particularly the cellobiohydrolases.

*Trichoderma reesei* CBH I (SEQ ID NO: 5) is a mesophilic cellulase which plays a major role in the hydrolysis of cellulose. An artificial ternary cellulase system consisting of a 90:10:2 mixture of *T. reesei* CBH 1, *Acidothermus cellulolyticus* EI, and *Aspergillus niger* β-D-glucosidase is capable of releasing as much reducing sugar from pretreated yellow poplar as the native *T. reesei* system after 120 h. This result is encouraging for the ultimate success of engineered cellulase systems, because this artificial enzyme system was tested at 50° C., a temperature far below that considered optimal for EI, in order to spare the more heat labile enzymes CBH I and β-D-glucosidase. To increase the efficiency of such artificial enzyme systems it is desirable to engineer new *T. reesei* CBH I variant enzymes capable of active expression in heterologous hosts. The use of the heterologous host *Aspergillus awamori*, could provide an excellent capacity for synthesis and secretion of *T. reesi* CBH I because of its ability to correctly fold and post-translationally modify proteins of eukaryolic origin. Moreover, *A. awamori* is believed to be an excellent test-bed for *Trichoderma* coding sequences and resolves some of the problems associated with site directed mutagenesis and genetic engineering in *Trichoderma*.

In consideration of the foregoing, it is therefore desirable to provide variant cellulase enzymes having enzymatic activity when expressed in a heterologous host, and to provide variant cellulase enzymes that have improved thermal tolerance over the native as produced by *Trichoderma reesei*.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

Briefly, provided herein is a method for making an active cellobiohydrolase in a heterologous host, the method comprising reducing glycosylation of the cellobiohydrolase, reducing glycosylation further comprising reducing an N-glycosylation site amino acid residue with a non-glycosyl accepting amino acid residue. Further provided is a cellobiohydrolase, comprising reduced glycosylation variant cellobiohydrolase enzymes.

Further provided is an isolated Cel7A polypeptide comprising one or more mutations in the catalytic domain of the polypeptide relative to the catalytic domain of a wild type Cel7A polypeptide, wherein the one or more mutations reduce N-linked glycosylation of the isolated polypeptide relative to the wild type polypeptide. In some embodiments, the Cel7A polypeptide catalytic domain comprises 1 mutation. In other embodiments, the Cel7A polypeptide comprises 2 mutations. In still other embodiments, the Cel7A polypeptide catalytic domain comprises 3 mutations. In further embodiments, the Cel7A polypeptide catalytic domain comprises 4 or more mutations.

Also provided herein is an isolated Cel7A polypeptide comprising increased O-linked glycosylation of the linker domain relative to a linker domain of a wild type Cel7A polypeptide. The increased O-linked glycosylation is a result of the addition of and/or substitution of one or more serine and/or threonine residues in the linker domain relative to the linker domain of the wild type polypeptide.

In some embodiments, the isolated Cel7A polypeptide comprises mutations in the catalytic domain of the polypeptide relative to the catalytic domain of a wild type Cel7A polypeptide and further comprises increased O-linked glycosylation of the linker domain relative to a linker domain of a wild type Cel7A polypeptide. The mutations in the catalytic domain reduce N-linked glycosylation of the isolated polypeptide relative to the wild type polypeptide. The addition of and/or substitution of one or more serine and/or threonine residues to the linker domain relative to the linker domain of the wild type polypeptide increases O-linked glycosylation of the isolated polypeptide.

Still further provided is a composition comprising an isolated Cel7A polypeptide, wherein the polypeptide comprises a catalytic domain having mutations relative to a wild type Cel7A polypeptide, wherein the mutations reduce N-linked glycosylation of the isolated polypeptide relative to the wild type polypeptide.

Provided herein is an isolated nucleic acid molecule comprising a nucleic acid sequence encoding a Cel7A polypeptide, wherein the Cel7A polypeptide catalytic domain comprises mutations with respect to a wild-type Cel7A, and wherein the mutations reduce N-linked glycosylation of the Cel7A polypeptide relative to the wild type Cel7A polypeptide.

Still further provided is a method of making an active cellobiohydrolase comprising modifying a wild type cellobiohydrolase to reduce N-linked glycosylation within the catalytic core, wherein the modification comprises replacing one or more N-linked glycosylation site amino acids with a non-glycosyl accepting amino acid.

In some embodiments, the above active cellobiohydrolase is further modified by increasing O-linked glycosylation of the linker domain relative to a linker domain of a wild type Cel7A polypeptide. The increased O-linked glycosylation is a result of the addition of and/or substitution of one or more serine and/or threonine residues to the linker domain relative to the linker domain of the wild type polypeptide.

Also provided is a method of making an active cellobiohydrolase comprising modifying a wild type cellobiohydrolase to increase O-linked glycosylation of the linker domain relative to a linker domain of a wild type Cel7A polypeptide, wherein the increased O-linked glycosylation is a result of the addition of and/or substitution of one or more serine and/or threonine residues to the linker domain relative to the linker domain of the wild type polypeptide.

Provided herein are exemplary cellobiohydrolases from organisms such as *Trichoderma viride*, *Trichoderma reesei*, *Hypocrea lixii*, *Phanerochaete chrysosporhim*, *Volvariella volvacea*, *Talaromyces emersonii*, *Penicillium funiculosum*, *Penicillium janthinellum*, *Aspergillus nidulans*, *Thielavia australiensis*, and *Chrysosporium lucknowense*.

In addition to the exemplary aspects and embodiments described above, further aspects and embodiments will become apparent by reference to the drawings and by study of the following descriptions.

BRIEF DESCRIPTION OF THE FIGURES

FIG. 1. Coding sequence of the cbhI gene (SEQ ID NO: 4). Lower case letters represent the signal sequence, upper case letters the catalytic domain, bolded italics the linker region, and upper case underlined the cellulose-binding domain.

Figure 2:
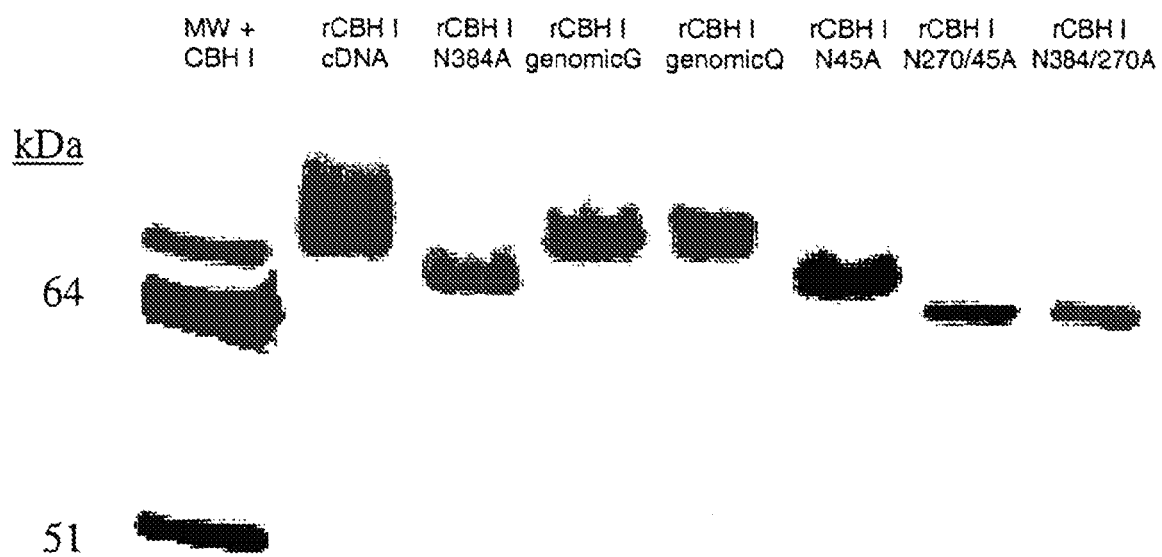
FIG. 2. SDS-PAGE Western blot with anti-CBH I antibody showing the reduction on molecular weight of rCBH I expression clones as a function of introduction of N to A modifications.

Exemplary embodiments are illustrated in referenced figures of the drawings. It is intended that the embodiments and figures disclosed herein are to be considered illustrative rather than limiting.

DESCRIPTION

Filamentous fungi produce enzyme mixtures capable of degrading the cellulose and hemicellulose in plant cell walls. These cell wall deconstruction enzymes are important for processes designed to produce ethanol and other products from biomass. Those species that degrade biomass produce a diverse collection of cellulose-degrading enzymes that include at least one glycosyl hydrolase family 7 cellobiohydrolase specific for the reducing end of cellulose. In *Trichoderma reesei* and *Penicillium funiculosum*, these enzymes are designated Cel7A. As used throughout the specification and in the claims, Cel7A includes or is interchangeable with any glycosyl hydrolase family 7 enzyme with cellobiohydrolase activity. Cellobiohydrolases from the Glycosyl Hydrolase family 7 are found exclusively in fungi that are known to degrade microcrystalline cellulose, a highly ordered form of cellulose. As a component of commercial cellulase formulations, cellobiohydrolases may be important for the economics of biomass conversion processes.

Protein glycosylation, a natural posttranslationa event, occurs during the secretion and maturation process of these enzymes and results in the addition of glycans to either asparagines (N-linked) or serines and threonines (O-linked). The catalytic domains of all family 7 cellobiohydrolases contain N-linked glycosylation and the linker peptides of these enzymes are also decorated with O-linked glycans.

Glycosyl hydrolase family 7 protein folding is based on their primary amino acid sequence and is highly conserved between organisms. Some also have high sequence homology and as such the two enzymes from *T. reesei* and *P. funiculosum*. Typically, cellobiohydrolase general folding patterns are conserved more than their primary amino acid sequences.

Further examples of organisms with glycosyl hydrolase family 7 enzymes include, but are not limited to, *Trichoderma viride, Hypocrea lixii, Phanerochaete chrysosporium, Volvariella volvacea, Talaromyces emersonii, Penicillium janthinellum, Aspergillus nidulans, Thielavia australiensis*, and *Chrysosporium lucknowense*. There are currently more than 50 known members of Glycosyl Hydrolase family 7 and these members can be further reduced to more than 8 subgroups based on peptide sequence homology.

Embodiments described herein include isolated polypeptides, compositions comprising isolated polypeptides, nucleic acid molecules, and methods of making active cellobiohydrolases.

DEFINITIONS

The following definitions are provided to facilitate understanding of certain terms.

The term "amino acid" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylation, covalent attachment of flavin, ADP-ribosylation, cross-linking, iodination, methylation, and the like.

The phrases "catalytic core" and "catalytic domain" are used interchangeably herein. The structure of the Cel7 catalytic domain creates an active site tunnel which is important to the mechanism of the enzyme.

The phrase "nucleic acid sequence" refers to the order or sequence of linear polymers of nucleotides linked by 3',5' phosphodiester linkages. A nucleic acid sequence can be either DNA or RNA.

The terms "protein", "peptide", and "polypeptide" are used interchangeably to denote an amino acid polymer or a set of two or more interacting or bound amino acid polymers.

"Expression" refers to transcription and translation occurring within a host cell. The level of expression of a DNA molecule in a host cell may be determined on the basis of either the amount or corresponding mRNA that is present within the cell or the amount of DNA molecule encoded protein produced by the host cell.

The phrase "foreign DNA" refers to any DNA transferred from foreign origin. Exemplary foreign DNAs include but are not limited to DNA from foreign species, recombinant DNA, mutagenized DNA, shuffled DNA, etc. Foreign DNA can be transferred in many ways known to those skilled in the art, including, for example, in the form of a plasmid, cosmid, insertion element, transposon, chromosome, or naked DNA such as in homologous recombination.

"Host microorganism" refers to a microorganism useful for the expression of proteins encoded by foreign DNA or other low molecular weight nucleic acid.

"Plasmid" refers to an extrachromosomal, circular DNA molecule capable of replication in bacteria. When the word plasmid is used herein, it is understood that any other foreign DNA can be substituted.

"Promoter" refers to the region of DNA at the upstream (5-prime) end of a gene or operon that serves as the initiation site for transcription.

A percent "sequence identity" for any subject nucleic acid or amino acid sequence (e.g., any of the cellobiohydrolase polypeptides described herein) relative to another nucleic acid or amino acid sequence can be determined as follows: determine the number of matched positions in aligned nucleic acid sequences, divide the number of matched positions by the total number of aligned nucleotides, and multiply by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (B12seq) program from the stand-alone version of BLASTZ containing BLASTN version 2.0.14 and BLASTP version 2.0.14. This stand-alone version of BLASTZ can be obtained from the U.S. government's National Center for Biotechnology Information web site. Instructions explaining how to use the B12seq program can be found in the readme file accompanying BLASTZ.

B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to −1; -r is set to 2; and all other options are left at their default setting. The following command will generate an output file containing a comparison between two sequences: C:\B12seq-i c:\seq 1.txt -j c:\seq2.txt -p blastn -o c:\output.txt -q -1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (i) a 500 amino acid target sequence is compared to a subject amino acid sequence, (ii) the B12seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., (180/200)× 100=90). In some embodiments, the amino acid sequence of a wild type Cel7A polypeptide as described herein has at least about 35% sequence identity to the amino acid sequence of SEQ ID NOs 100-111. In other embodiments, the amino acid sequence of a polypeptide modified as described herein has greater than 45% sequence identity (e.g., >50, >55, >60, >65, >75%, >80%, >90%, or >95%) to the amino acid sequence of SEQ ID NOs 110-111.

It will be appreciated that different regions within a single nucleic acid molecule or amino acid sequence that aligns with an identified sequence can each have their own percent identity.

The identification of conserved regions in a template, or subject, polypeptide can facilitate polypeptide sequence analysis. Conserved regions can be identified by locating a region within the primary amino acid sequence of a template polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains at sanger.ac.uk/Pfam/ on the World Wide Web and genome.wustl.edu/Pfam/ on the World Wide Web. From the Pfam database, consensus sequences of protein motifs and domains can be aligned with the template polypeptide sequence to determine conserved region(s).

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment. It is therefore understood, as those skilled in the art will appreciate, that more than the specific exemplary sequences are contemplated herein.

"Wild-type" refers to the typical form of an organism, strain, gene, or characteristic as it occurs in nature.

Modification to the Catalytic Domain of Cellobiohydrolase I.

When expressed in a eukaryotic heterologous host, such as in fungi and other yeasts, plants, or algae, the enzymes tend to be hyperglycosylated at N-linked sites that can impact the functionality of the enzyme, often resulting in reduced activity on biomass. The removal of N-linked glycosylation sites using protein engineering (or enzymatically using endoglycosidases) reduces hyperglycosylation and improves the activity of recombinant Cel7A from organisms such as T. reesei and P. funiculosum. Specifically, surface sites around the active site tunnel (core of the catalytic domain) were determined by the inventors to be very sensitive to hyperglycosylation. Replacing asparagines with amino acids not known to perturb the peptide backbone, such as substitution with glycine or alanine, eliminates the possibility for glycan addition at theses sites and resulted in an improvement in activity. A direct pair-wise amino acid comparison of these two enzymes shows they have high amino acid homology and contain analogous N-linked glycosylation sites on the catalytic domain. When expressed in Aspergillus awamori, variations in specific N-linked glycan sites were found to impact their thermal stability and specific performance on cellulose. The significance of the N-linked glycans on the catalytic core of these enzymes was investigated using a systematic approach based on adding and/or removing N-linked glycosylation motifs by site directed mutagenesis. Modified sequences expressed in A. awamori were purified to homogeneity and subjected to activity and stability testing. As described herein, N-linked glycans existing (or introduced) near the active site tunnel of Cel7A enzymes have the most significant impact on enzyme stability and activity. This comparative approach is applicable to other fungal Cel7A enzymes of industrial importance including, for example, Cel7A enzymes from *Trichoderma viride, Hypocrea lixii, Phaneroehaete chrysosporium, Volvariella volvacea, Talaromyces emersonii, Penicillium janthinellum, Aspergillus nidulans, Thielavia australiensis*, and *Chrysosporium lucknowense.*

Modification to the Linker Peptide of Cellobiohydrolase I.

The linker region of the protein is also naturally glycosylated to various extents. While not wishing to be bound by theory, glycosylation on the linker region may impact the susceptibility of this region to proteases and may play a role in defining the solution structure of this peptide. If cleaved between the catalytic domain and the linker peptide, the truncated enzyme has significantly reduced activity on crystalline cellulose. Engineering the native linker region or substituting this region with heterologous linker regions to regulate the addition of glycan reduces the undesirable truncation of the protein due to proteolysis. This is especially important when the enzyme is expressed in heterologous hosts, such as fungi and other yeasts, plants, or algae. As demonstrated herein, the linker region of the *P. funiculosum* is more heavily glycosylated than the linker region of the *T. reesei* enzyme and less susceptible to proteolysis by the general protease, papain. Addition of O-linked glycosylation sites to the linker region using protein engineering reduces the susceptibility of the linker peptide to proteolytic cleavage.

Methods of Engineering Active Cellobiohydrolases

Provided herein is a method of making an active cellobiohydrolase comprising modifying a wild type cellobiohydrolase to reduce N-linked glycosylation within the catalytic core, wherein the modification comprises replacing one or more N-linked glycosylation site amino acids with a non-glycosyl accepting amino acid.

In some embodiments, the active cellobiohydrolase is further modified by increasing O-linked glycosylation of the linker domain relative to a linker domain of a wild type Cel7A polypeptide. The increased O-linked glycosylation is a result of the addition of and/or substitution of one or more serine and/or threonine residues to the linker domain relative to the linker domain of the wild type polypeptide.

Also provided is a method of making an active cellobiohydrolase comprising modifying a wild type cellobiohydrolase to increase O-linked glycosylation of the linker domain relative to a linker domain of a wild type Cel7A polypeptide, wherein the increased O-linked glycosylation is a result of the addition of and/or substitution of one or more serine and/or threonine residues to the linker domain relative to the linker domain of the wild type polypeptide.

Exemplary wild type Cel7A cellobiohydrolases useful according to the methods described include, but are not limited to, the polypeptides encoded by SEQ ID NOs 100-111. Tables 6 and 8 show the N-linked glycosylation sites in bold for each sequence which are independently substituted with an amino acid that is not susceptible to N-linked glycosylation. Illustratively, an asparagine subject to N-linked glycosylation is exchanged for an amino acids such as, for example, glycine or alanine. Those skilled in the art understand that Cel7 or glycosyl hydrolase cellobiohydrolases originating from other organisms including fungi and other yeasts, plants, and algae are similarly useful according to the methods described herein.

In some embodiments, a wild type cellobiohydrolase as described herein has at least about 35% overall amino acid sequence identity with the polypeptides encoded by SEQ ID NOs 100-111, e.g., at least about 35%, 40%, 45%, 50%, 55%, 60%, 65%, 70%, 75%, 80%, 85%, 90%, 91%, 92%, 93%, 94% 95%, 96%, 97%, 98%, or 99% sequence identity. However, homology in tertiary structure of the enzyme, i.e. the protein folding, can be more important than sequence identity in this family of enzymes.

Modification of wild type Cel7A cellobiohydrolases can be achieved through protocols known to those skilled in the art. In some aspects, the modification of wild type cellobiohydrolases is achieved through the use of site directed mutagenesis. Various mutagenesis kits for site directed mutagenesis are available to those skilled in the art and the methods for site directed mutagenesis are well known.

Aspects and embodiments as described with respect to the above methods are applicable to polypeptides, nucleic acid molecules, and compositions illustrated throughout the specification and claims.

Polypeptides, Nucleic Acid Molecules, and Compositions

In some embodiments an isolated Cel7A polypeptide is provided comprising one or more mutations in the catalytic domain of the polypeptide relative to the catalytic domain of a wild type Cel7A polypeptide. The one or more mutations reduce N-linked glycosylation of the isolated polypeptide relative to the wild type polypeptide.

As described above, exemplary wild type Cel7A cellobiohydrolases useful according to the method described include, but are not limited to, the polypeptides encoded by SEQ ID NOs 100-111. Tables 6 and 8 show the N-linked glycosylation sites in bold for each sequence which are independently substituted with an amino acid that is not susceptible to N-linked glycosylation. Such amino acids include, for example, glycine and alanine. Those skilled in the art understand that fungal Cel7A cellobiohydrolases produced in other organisms such as fungi and yeasts, plants, and algae are similarly useful according to the methods described herein.

Molecular dynamic computer models using the software package CHARM indicate that the asparagines with closest proximity to the active site tunnel have the highest likelihood to contain glycan that will negatively impact activity. Targeting these sites will allow the greatest probability to improve the activity when expressed in a hererologous host such as yeast, plants or algae.

In some aspects, the isolated polypeptide with reduced N-linked glycosylation of the catalytic domain has improved cellulase activity relative to its respective wild type Cel7A polypeptide. Improved relative activity can be determined using, for example, cellulose hydrolysis assays as demonstrated in the Examples below. In other aspects, the isolated polypeptide has improved thermal stability relative to its respective wild type Cel7A polypeptide.

Polypeptides generated according to the methods described herein can be expressed in a heterologous host cell such as, for example, *Aspergillus awamori* and *Trichoderma reesei*. Other organisms including, but not limited to, yeast such as *Saccharomyces cerevisiae, Pichia pastoris, Kluyveromyces lactis*, and plants such as Arabidopsis, barley, citrus, cotton, maize, poplar, rice, soybean, sugarcane, wheat, switch grass, alfafa, miscanthus, and trees, such as hardwoods and softwoods are contemplated herein as hosts for CBHI expression.

Other embodiments provide an an isolated Cel7A polypeptide comprising increased O-linked glycosylation of the linker domain relative to a linker domain of a wild type Cel7A polypeptide. The increased O-linked glycosylation is a result of the addition of and/or substitution of one or more serine and/or threonine residues to the linker domain relative to the linker domain of the wild type polypeptide.

Illustratively, SEQ ID NOs 110 and 111 as shown in Table 6 show the location of the linker domain in italicized text. The linker domain of the *P. funiculosum* Cel7A enzyme is about 29 amino acids in length. In some aspects, any one or more of the 29 residues can be replaced independently with a serine or threonine residue. In other aspects, one or more serine or threonine residues are added to the 29 amino acid sequence at any point in the sequence. In still other aspects, any one or more of the 29 amino acid residues are replaced independently with a serine or threonine residue and one or more serine or threonine residues are added to the sequence at any position in the sequence. Similarly, the linker domain of the *T. reesei* Cel7A enzyme is about 36 amino acids in length. In some aspects, any one or more of the 36 residues can be replaced independently with a serine or threonine residue. In other aspects, one or more serine or threonine residues are added to the 36 amino acid sequence at any point in the sequence. In still other aspects, any one or more of the 36 amino acid residues are replaced independently with a serine or threonine residue and one or more serine or threonine residues are added to the sequence at any position in the sequence.

In some aspects, the isolated polypeptide with increased O-linked glycosylation of the linker domain has improved cellulase activity relative to its respective wild type Cel7A polypeptide. As described above, improved relative activity can be determined using, for example, cellulose hydrolysis assays as demonstrated in the Examples. In other aspects, the isolated polypeptide has improved thermal stability relative to its respective wild type Cel7A polypeptide.

In some embodiments, the isolated Cel7A polypeptide comprising mutations in the catalytic domain of the polypeptide relative to the catalytic domain of a wild type Cel7A polypeptide further comprises increased O-linked glycosylation of the linker domain relative to a linker domain of a wild type Cel7A polypeptide. The mutations in the catalytic domain reduce N-linked glycosylation of the isolated polypeptide relative to the wild type polypeptide. The addition of and/or substitution of one or more serine and/or threonine residues to the linker domain relative to the linker domain of the wild type polypeptide increases O-linked glycosylation of the isolated polypeptide.

Provided herein is a composition comprising an isolated Cel7A polypeptide, wherein the polypeptide comprises a catalytic domain having one or more mutations relative to a wild type Cel7A polypeptide, wherein the one or more mutations reduce N-linked glycosylation of the isolated polypeptide relative to the wild type polypeptide.

Also provided is a composition comprising an isolated Cel7A polypeptide, wherein the polypeptide comprises a linker domain with increased O-linked glycosylation relative to a linker domain of a wild type Cel7A polypeptide. The increased O-linked glycosylation is a result of the addition of and/or substitution of one or more serine and/or threonine residues to the linker domain relative to the linker domain of the wild type polypeptide.

In other embodiments the composition comprises an isolated Cel7A polypeptide wherein the polypeptide comprises a catalytic domain with reduced N-linked glycosylation and a linker domain with increased O-linked glycosylation.

Provided herein is an isolated nucleic acid molecule comprising a nucleic acid sequence encoding a Cel7A polypeptide, wherein the Cel7A polypeptide comprises one or more mutations with respect to a wild-type Cel7A, and wherein the one or more mutations reduce N-linked glycosylation of the Cel7A polypeptide relative to the wild type Cel7A polypeptide.

Further provided is an isolated nucleic acid molecule comprising a nucleic acid sequence encoding a Cel7A polypeptide, wherein the Cel7A polypeptide linker domain comprises increased O-linked glycosylation relative to a linker domain of a wild type Cel7A polypeptide. The increased O-linked glycosylation is a result of the addition of and/or substitution of one or more serine and/or threonine residues to the linker domain relative to the linker domain of the wild type polypeptide.

Unless specifically defined otherwise, all technical or scientific terms used herein have the same meaning as commonly understood by one of ordinary skill in the art. Although any methods and materials similar or equivalent to those described herein can be used in the practice or testing of the embodiments described herein, exemplary methods and materials are now described.

Aspects and embodiments as described with respect to the above polypeptides, nucleic acid molecules, and compositions are applicable to the methods illustrated throughout the specification and claims.

EXAMPLES

The following examples are provided for illustrative purposes only and are not intended as limiting in any manner.

Example 1

Acquisition of the CBH I Encoding Sequence

Acquisition of the gene was done by either cDNA cloning or by PCR of the gene from genomic DNA. CBH I cDNA was isolated from a *T. reesei* strain RUT C-30 cDNA library constructed using a PCR-generated probe based on published CBH I gene sequences (Shoemaker, et al., 1983). The cDNA's were cloned (using the Zap Express cDNA kit from Stratagene; cat. #200403) into the XhoI and EcoRI site(s) of the supplied, pre-cut lambda arms. An XhoI site was added to the 3' end of the cDNA during cDNA synthesis, and sticky-ended RE linkers were added to both ends. After XhoI digestion, one end has an XhoI overhang, and the other (5' end) has an Eco RI overhang. The insert can be removed from this clone as an approximately 1.7 kb fragment using SalI or SpeI plus XhoI in a double digest. There are two Eco RI, one Bam HI, 3 SacI and one HindIII sites in the coding sequence of the cDNA itself. The plasmid corresponding to this clone was excised in vivo from the original lambda clone, and corresponds to pB210-5A. Thus, the cDNA is inserted in parallel with a Lac promoter in the pBK-CMV parent vector. Strain pB210-5A grows on LB+kanamycin (50 µg/mL).

Acquisition of the cbhI gene was also achieved by PCR of genomic DNA. With this approach the fungal chromosomal DNA from *T. reesei* strain Rut C-30 was prepared by grinding the fungal hypae in liquid nitrogen using a mortar and pestle to a fine powder. The genomic DNA was then extracted from the cell debris using a Qiagen DNAeasy Plant Mini kit. Amplification of the DNA fragment that encodes for the cbhI gene, including introns, was performed using polymerase chain reaction (PCR) with specific primers for the *T. reesei* cbhI gene. The primers 5'-AGAGAGTCTAGACACG- GAGCTTACAGGC-3' (SEQ ID NO: 9) that introduces a Xba I site and the primer 5'-AAAGAAGCGCGGCCG CGCCTGCACTCTCCAATCGG-3' (SEQ ID NO: 97) that introduces a unique Not I site were used to allowing cloning into the pPFE *Aspergillus/E. coli* shuttle vectors that are described below. The amplified PCR product was then gel purified and cloned directly into the vectors.

Example 2

Production of Active Recombinant CBHI (rCBH I) in *Aspergillus awamori*

Construction of the Fungal Expression Vectors pPFE-1/CBHI and pPFE-2/CBH1

The coding sequence for *T. reesei* CBH I was successfully inserted and expressed in *Aspergillus awamori* using the fungal expression vector pPFE2 (and pPFE1). Vectors pPFE1 and pPFE2 are *E. coli/Aspergillus* shuttle vectors, and contain elements required for maintenance in both hosts. Both pPFE-1 and pPFE-2 vectors direct the expression of a fusion protein with a portion of the glucoamylase gene fused to the gene of interest. The pPFE1 vector contains a region of the glucoamylase gene, with expression under the control of the *A. awamori* glucoamylase promoter. The protein of interest is expressed as a fusion protein with the secretion signal peptide and 498 amino acids of the catalytic domain of the glucoamylase protein. The majority of the work presented here was done using the pPFE2 expression vector, chosen because of its smaller size, simplifying the PCR mutation strategy by reducing extension time.

Figure 3:
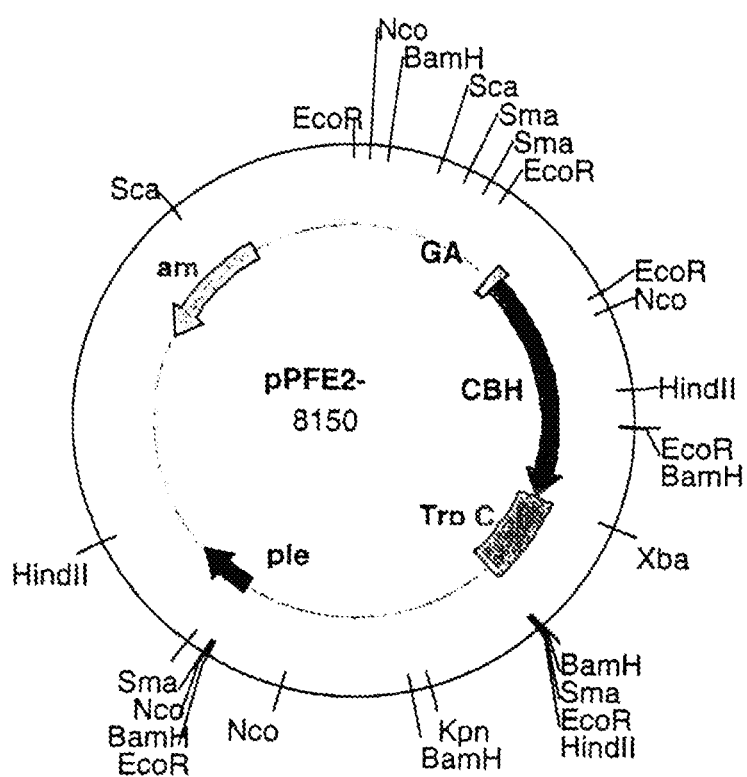
FIG. 3. Plasmid map for the fungal expression vector pPFE2/CBH I.

The major features of the pPFE2-CBH1 construct are shown in FIG. 3. With both the pPFE1/CBH1 and the pPFE2/CBH1 vectors, the sequence immediately upstream of the Not I site encodes a LysArg dipeptide. A host KEX-2 like protease recognizes this dipeptide sequence during the secretion process, and the fusion peptide is cleaved, removing the glucoamylase secretion signal peptide or the longer catalytic domain of glucoamylase in the case of pPFE1. In this way, the recombinant CBH I protein experiences an "efficient ride" through the *A. awamori* secretion system and is expressed with the native N-terminal protein. The net result is that the recombinant CBH I is processed so that it can accumulate in the medium without its glucoamylase secretion signal fusion partner. The vector contains the *Streptoalloteichus hindustamus* phleomycin resistance gene, under the control of the *A. niger* β-tubulin promoter, for positive selection of *Aspergillus* transformants. The pPFE/CBH1 vector also contains a β-lactamase gene for positive selection using ampicillin in *E. coli*, and also contains the *A. niger* trpc terminator: The insertion of the CBH I coding sequence into the pPFE vectors was accomplished using two methods. Vector DNA was first produced in 500 mL cultures of *E. coli* XL1 Blue and the plasmids purified using Promega maxi-preps DNA purification kits.

Approach 1: Blunt-Xba I Fragment Generation.

1. Oligonucleotides were designed to give a blunt end on the 5' end and an engineered Xba I site on the 3' end of the PCR fragment.

2. The full-length coding sequence for CBH I was obtained by PCR using Pfu

DNA polymerase and using the cDNA construct pB510-2a as the template. Pfu DNA polymerase generates blunt-ended PCR products exclusively.

3. The pPFE vectors were digested using NotI and confirmed by agarose gel electrophoresis. The NotI overhang was then digested using Mung Bean nuclease. The DNA was purified and the vector and CBH1 PCR fragment digested using XbaI.

4. The vector and PCR product were then ligated using T4 DNA ligase and the DNA used to transform *E. coli* XL-1 Blue and *E. coli* DH5α using electroporation.

Approach 2: NotI-XbaI Fragment Approach.

1. Oligonucleotides were designed to give a Not I site on the 5' end, and an engineered Xba I site on the 3' end of the PCR fragment.

2. The full-length coding sequence for CBH I was obtained by PCR using Pfu DNA polymerase and using the cDNA construct pB510-2a as the template.

3. The pPFE vectors and the PCR product were digested using Not 1 and Xba 1.

4. The CBH I PCR product was directionally cloned into the pPFE2 vector using T4 DNA ligase and transformed into *E. coli* XL-1 Blue.

5. The insertion of the CBH I coding sequence into the pPFE2 vector was confirmed using PCR, restriction digest analysis, and DNA sequencing through the insertion sites. The entire coding sequence of the insert was also confirmed by DNA sequencing.

The constructs produced using these two methods was then used to transform *A. awamori* and to express rCBH I, as confirmed by western blot analysis of culture supernatant. The rCBH I expressed in *A. awamori* tends to be over-glycosylated as evidenced by the higher molecular weight observed on western blot analysis. Over-glycosylation of CBH I by *A. awamori* was confirmed by digestion of the recombinant protein with endoglycosidases. Following endoglycosidase H and F digestion, the higher molecular weight form of the protein collapses to a molecular weight similar to native CBH I.

Example 3

Method for Producing PCR Site Directed Mutations for Glycosylation Removal and Improved Thermalstability The QuickChange™ Site Directed Mutagenesis kit (StratAgene, San Diego, Calif.) was used to generate mutants with targeted amino acid substitutions. To introduce these specific amino acid substitutions, mutagenic primers (between 25 and 45 bases in length) were designed to contain the desired mutation that result in the targeted amino acid substitution. Pfu DNA polymerase was then used to amplify both strands of the double-stranded vector, which contained the CBH I insertion sequence, with the resultant inclusion of the desired mutation from the synthetic oligonucleotides. Following temperature cycling, the product was treated with the exonuclease Dpn I to digest the parental methylated DNA template and the PCR product was used to transform Epicurian Coli XL1-Blue supercompetent cells.

The vector pPFE2/CBH1 requires a relatively long PCR reaction (8.2 kB) to make site-specific changes using the Stratagene Quik Change protocol. The PCR reaction was optimized as follows using a GeneAmp PCR System 2400, Perkin Elmer Corporation. The reaction mixture contained 50 ng of template DNA, 125 ng each of the sense and antisense mutagenic primers, 5 μL of Stratagene 10× cloned Pfu buffer, 200 μM of each: dNTP, 5 mM $MgCl_2$ (total Final concentration of $MgCl_2$ is 7 mM); and 2.5 U Pfu Turbo DNA polymerase. The PCR reaction was carried out for 30 cycles, each consisting of one minute denaturation at 96° C., 1 minute annealing at 69° C. and a final extension for 10 min at 75° C., followed by a hold at 4° C. Agarose gel electrophoresis, ethidium bromide staining, and visualization under UV transillumination were used to confirm the presence of a PCR product.

PCR products were digested with the restriction enzyme Dpn1, to degrade un-mutagenized parental DNA, and transformed into *E. coli* (Stratagene Epicurian Coli Supercompetent XL-1 Cells). Ampicillin resistant colonies were picked from LB-amp 100 plates and mutations were confirmed by DNA sequencing.

Template DNA from *E. coli* XL1-blue cells transformed with Dpn1 treated mutaginzed DNA was prepared for sequencing using the QIAprep-spin plasmid purification mini-prep procedure (Qiagen, Inc.). The transformed XL1-blue cells where grown overnight in 5 mL of LB broth with 100 μg/mL ampicillin selection. Cells were removed by centrifugation and the plasmid isolated using the protocol outlined in the QIAprep-spin handbook. The concentration of the template DNA was adjusted to 0.25 μg/μL and shipped along with sequencing oligonucleotides to the DNA Sequencing Facility at Iowa State University.

After the mutation was confirmed by DNA sequence alignment comparisons using the software package OMIGA, and the DNA was prepared for transformation of *A. awamori*. The transformed *E. coli* XL1/blue cells were grown overnight on LB plates with 100 μg/mL ampicillin at 37° C. A single colony was then used to inoculate a 1 L baffled Erlenmeyer flask that contained 500 mL of LB broth and 100 μg/mL ampicillin. The culture was allowed to grow for 16 to 20 hours at 37° C. with 250 rpm shaking in a NBS reciprocating shaking incubator. The cells were harvested and the plasmid DNA purified using a Promega maxi-prep purification kit. The purified maxi-prep DNA was subsequently used to transform *A. awamori* spheroplasts using the method described below.

Transformation of *Aspergillus awamori* with *Trichoderma reesei* CBHI Coding Sequence, Generating Fungal Spheroplasts.

*A. awamori* spheroplasts were generated from two-day-old cultures of mycelia pellets. A heavy spore suspension was inoculated into 50 mL of CM broth (5.0 g/L-yeast extract; 5.0 g/L tryptone; 10 g/L glucose; 50 mL/L 20× Clutterbuck's salts, pH 7.5 (adjusted by addition of 2.0N NaOH)) and grown at 225 rpm and 28° C. in a baffled 250 mL Erlenmeyer flask. The mycelia were collected by filtration through Miracloth and washed with about 200 mL KCM (0.7M KCl; 10 mM MOPS pH 5.8). The washed mycelia were transferred to 50 mL of KCM+500 mg Novazym 234 in a 50-mL unbaffled flask and incubated O/N at 80 rpm and 30° C. After digestion, the remaining mycelia was removed by filtration through Miracloth and the spheroplasts were collected in 50 mL disposable tubes and pelleted at 2500× g in a swinging bucket rotor for 15 minutes. The supernatant was discarded and the spheroplasts gently resuspended in 20 mL 0.7M KCl by tituration with a 25-mL disposable pipet. The spheroplasts were pelleted and washed again, then resuspended in 10 mL KC (0.7M KCl+50 mM $CaCl_2$). After being pelleted, the spheroplasts were resuspended into 1.0 mL of KC.

Transformation was carried out using 50 μL of spheroplasts+5 μL DNA (pPFE1 or pPFE2 about 200 μg/mL)+12.5 μL PCM (40% PEG8000+50 mM $CaCl_2$+10 mM MOPS pH 5.8). After incubation for 60 minutes on ice, 0.5 mL PCM was added and the mixture was incubated for 45 minutes at room temperature. One milliliter of KCl was added and 370 μL of the mix was added to 10 mL of molten CMK (CM+2% agar+0.7M KCl) top agar at 55° C. This mixture was immediately poured onto a 15 mL CM 170 plate (CM+2% agar+ 170 μg/μL Zeocin). Negative transformation controls substituted sterile dH$_2$ for DNA. Plating the transformation mix onto CM plates without Zeocin performed positive spheroplast regeneration controls. The poured plates were incubated at 28° C. in the dark for 2-7 days.

Transformation of *Aspergillus awamori* with Native and Modified CBH I Coding Sequence.

*Aspergillus awamori* spore stocks were stored at −70° C. in 20% glycerol, 10% lactose. After thawing, 200 µL of spores were inoculated into 50 mL CM broth in each of eight-baffled 250 mL Erlenmeyer flask. The cultures were grown at 28° C., 225 rpm for 48 hours. The mycelial balls were removed by filtration with sterile Miracloth (Calbiochem, San Diego, Calif.) and washed thoroughly with sterile KCM. Approximately 10 g of washed mycelia were transferred to 50 mL KCM+250 mg Novozym234 in a 250 mL baffled Erlenmeyer flask. The digestion mixture was incubated at 30° C., 80 rpm for 1-2 h and filtered through Miracloth into 50 mL conical centrifuge tubes. The spheroplasts were pelleted at 2000× g for 15 min and resuspended in 0.7M KCl by gentle tituration with a 25 mL pipette. This was repeated once. After a third pelleting, the spheroplasts were resuspended in 10 mL KC, pelleted and resuspended in 0.5 mL KC using a wide-bore pipet tip. The washed spheroplasts were transformed by adding 12.5 µL PCM and 5 µL DNA (about 0.5 µg/µL) to 50 µL of spheroplasts in sterile 1.5 mL Eppendorf tubes. After incubation on ice for 45 minutes, 0.5 mL of room temperature PCM was added to the transformation mixture and was mixed by tituration with a wide bore pipet tip. The mixture was incubated at room temperature for 45 minutes. One milliliter of KC was added and mixed. The mixture was allocated between four tubes of CM top agar at 55° C., which were each poured over a 15 mL CM 170 plate. The plates were incubated at 28° C. for 2-3 days. Subsurface colonies were partially picked with a sterile wide bore pipet tip, exposing the remaining part of the colony to air and promoting rapid sporulation. After sporulation, spores were streaked onto several successive CM 100 or CM300 plates. After a monoculture was established, heavily sporulated plates were flooded with sterile spore suspension medium (20% glycerol, 10% lactose), the spores were suspended and aliquots were frozen at −70° C. Working spore stocks were stored on CM slants in screw cap tubes at 4° C. Protein production was confirmed and followed by western blot using anti-CBH I monoclonal antibodies and the Novex Western Breeze anti-mouse chromogenic detection kit (Novex, San Diego, Calif.). Extracting genomic DNA using the YeaStar Genomic DNA Kit (Zymo Research, Orange, Calif.) and carrying out PCR with pfu-turbo DNA polymerase (Stratagene, La Jolla) and cbhI primers confirmed insertion of the gene.

Production and Purification of Native rCBH I Enzyme from *Aspergillus awamori*.

For enzyme production, spores were inoculated into 50 mL CM basal starch medium, pH 7.0, and grown at 32° C., 225 rpm in 250 mL baffled flasks. The cultures were transferred to 1.0 L of basal starch medium in 2800 mL Fembach flasks and grown under similar conditions. For large-scale enzyme production (>1 mg), these cultures were transferred to 10 L basal starch medium in a New Brunswick BioFlo3000 fermenter (10-L working volume) maintained at 20% DO, pH 7.0, 25° C., and 300 rpm. The fermentation was harvested by filtration through Miracloth after 2-3 days of growth.

After further clarification by glass fiber filtration, the rCBH I protein was purified by passing the fermentation broth over fourCBinD900 cartridge columns (Novagen, Madison, Wis.) connected in parallel using a Pharmacia FPLC System loading at 1.0 mL/min (Amersham Pharmacia Biotech, Inc., Piscataway, N.J.). The cartridges were equilibrated in 20 mM Bis-Tris pH 6.5 prior to loading and washed with the same buffer after loading. The bound rCBH I was then eluted with 100% ethylene glycol (3 mL/column) using a syringe. Alternatively, the supernatant was passed over a para-aminophenyl β-D-cellobioside affinity column, washed with 100 mM acetate buffer, pH 5.0, 1 mM gluconolactone and eluted in the same buffer containing 10 mM cellobiose. In either method, the eluted rCBH I was concentrated in Millipore Ultrafree-15 spin concentrator with a 10 kDa Biomax membrane to <2.0 mL and loaded onto a Pharmacia SuperDex200 16/60 size-exclusion column. The mobile phase was 20 mM sodium acetate, 100 mM sodium chloride, and 0.02% sodium azide, pH 5.0 running at 1.0 mL/min. The eluted protein was concentrated and stored at 4° C. Protein concentrations were determined for each mutant based upon absorbance at 280 nm and calculated from the extinction coefficient and molecular weight for each individual protein as determined by primary amino acid sequence using the ProtParam tool on the ExPASy website.

| Clutterbuck's Salts (20X) | |
|---|---|
| Na$_2$NO$_3$ | 120.0 g/L |
| KCl | 10.4 g/L |
| MgSO$_4$•7H$_2$O | 10.4 g/L |
| KH$_2$PO$_4$ | 30.4 g/L |
| CM- | |
| Yeast Extract- | 5 g/L |
| Tryptone- | 5 g/L |
| Glucose- | 10 g/L |
| Clutterbuck's Salts- | 50 mL |

Add above to 900 mL dH$_2$O, pH to 7.5, bring to 1000 mL
CM Agar=CM+20 g/L Agar
CMK=CM Agar+0.7M KCl
CM100=CM+100 µg/mL Zeocin (Invitrogen, Carlsbad, Calif.)
CM 170=CM+170 µg/mL Zeocin, 15 mL/plate
KCl=0.7M KCl
KC=0.7M KCl+50 mM CaCl$_2$
KCM=0.7M KCl+10 mM MOPS, pH 5.8
PCM=40% PEG 8000, 50 mM CaCl$_2$, 10 mM MOPS pH 5.8 (mix 4 mL 50% PEG+0.5 mL 500 mM CaCl$_2$ stock+ 0.5 mL 100 mM MOPS stock)

| Basal Starch Medium- | |
|---|---|
| Casein Hydrolysate, Enzymatic | 5 g/L |
| NH$_4$CL | 5 g/L |
| Yeast Extract | 10 g/L |
| Tryptone | 10 g/L |
| MgSO$_4$•7H$_2$0 | 2 g/L |
| Soluble Starch | 50 g/L |
| Buffer (Bis-Tris-Propane) | 50 mM |
| pH to 7.0 with NaOH | |

Example 4

Production of Reduced Glycosylation rCBH I: Sites N270A; N45A: and N384A rCHI/pPFE2 has been optimized using site-directed mutagenisis to achieve expression of native molecular weight CBHI in *A. awamori* by the following ways. The Quick-Change SDM kit (Stratagene, San Diego, Calif.) was used to make point mutations, switch amino acids, and delete or insert amino acids in the native cbhI gene sequence. The Quick Change SDM technique was performed using thermotolerant Pfu DNA polymerase, which replicates both plasmid strands with high fidelity and without displacing the mutant oligonucleotide primers. The procedure used the polymerase chain reaction (PCR) to modify the cloned cbhI DNA. The basic procedure used a supercoiled double stranded DNA (dsDNA) vector, with the cbhI gene insert, and two synthetic oligonucleotide primers containing a desired mutation. The oligonucleotide primers, each complimentary to opposite strands of the vector, extend during temperature cycling by means of the polymerase. On incorporation of the primers, a mutated plasmid containing the desired nucleotide substitutions was generated. Following temperature cycling, the PCR product was treated with a Dpn1 restriction enzyme. Dpn1 is specific for methylated and hemi-methylated DNA and thus digests the unmutated parental DNA template, selecting for the mutation-containing, newly synthesized DNA. The nicked vector DNA, containing the desired mutations, was then transformed into E. coli. The small amount of template DNA required to perform this reaction, and the high fidelity of the Pfu DNA polymerase contribute to the high mutation efficiency and minimizes the potential for the introduction of random mutations. Three glycosylation-site amino acids on the pro surface were targeted for substitution of an alanine (A) residue in place of asparagines (N). Single site substitutions were successfully completed in the cbhI coding sequence at sites N45, N270, and N384, of SEQ ID NO: 4 by site-directed mutagenesis, and confirmed by DNA sequencing.

Double and triple combinations of this substitution have also been completed in the cbhI coding sequence at sites N45, N270, and N384 by site directed mutagenesis and confirmed by DNA sequencing. These double and triple site constructs also yield rCBH1 enzymes with reduced glycosylation and, presumably, native activity.

TABLE 1

| Construct | Host | MW (kDa) | $K_m$ µmol pNPL | $V_{max}$ (µmol pNP/min/ mg protein) |
|---|---|---|---|---|
| T. reesei | None | 57.8 | 1.94 | 0.746 |
| rCBHI wt cDNA | A. awamori | 63.3 | 2.14 | 0.668 |
| rCBHI wt genomic | A. awamori | 63.3 | — | — |
| rCBHI N270A | A. awamori | 61.7 | 2.25 | 0.489 |
| rCBHI N384A | A. awamori | 61.3 | — | — |
| rCBHI wt genomic (G) | A. awamori | 63.3 | — | — |
| rCBHI N45A | A. awamori | 58.3 | — | — |
| rCBHI N270/45A | A. awamori | 58.3 | — | — |
| rCBHI N384/270A | A. awamori | 58.8 | — | — |

As shown in Table 1, Western blot analysis of the supernatant, obtained from a single glycosylation site mutant CBHFN270A culture expressed in A. awamori, demonstrated that a decrease, to lower molecular weight (61.7 kDa), in the amount of glycosylation of the protein had occurred, as compared to that in the wild type cDNA (63.3 kDa), and the wild type genomic DNA (63.3 kDa). These results demonstrate a reduction in the level of glycosylation in the reduced glycosylation mutant CBH1N270A, via expression in A. awamori. It is also shown, in the Table, that the CBH1N270A enzyme nearly retained its native enzymatic activity when assayed using the pNPL substrate. The variants CBH1N45A and CBH1384A also demonstrate a reduction in amount of glycosylation and native activity when expressed from the heterologous host A. awamori and when combined in the double mutations CBHIN270/45A and CBHIN270/384A reduce the level of glycosylation further.

Example 5

Amino Acid Mutations Targeted to Improve Thermal Tolerance of CBH I Helix Capping Mutants α-helices display dipole moments, i.e. positive at N-terminal and negative at C-terminal. Compensation for such dipole moments (capping) has been observed in a number of protein structures and has been shown to improve the protein stability. For example, the introduction of a negatively charged amino acid at the N-terminus and a positively charged amino acid at C-terminus of an α-helix increased the thermostability of T4 lysozyme and hen lysozyme, via an electrostatic interaction with the "helix dipole". Five amino acid sites were identified for helix capping (see Table 5).

Peptide Strain Removal Mutants

A small fraction of residues adopt torsion angles, phi-psi angles, which are unfavorable. It has been shown that mutation of such residues to Gly increased the protein stability as much as 4 kcal/mol. One amino acid site was selected for peptide strain removal (see Table 3).

Helix Propensity Mutants

Two amino acid sites were selected for helix propensity improvement.

Disulfide Bridge Mutants

Disulfide bonds introduced between amino acid positions 9 and 164 and between 21 and 142 in phage T4 lysozyme have been shown to significantly increase the stability of the respective enzymes toward thermal denaturation. The engineered disulfide bridge between residues 197 and 370 of CBH I should span the active site cleft and enhance its thermostability. The active site of CBH I is in a tunnel. The roof over the tunnel appears to be fairly mobile (high temperature-factors). At an elevated temperature the mobility of the tunnel is too significant to position all the active site residues. The disulfide linkage should stabilize the roof of the tunnel making the enzyme a consistent exocellulase even at a high temperature. Two amino acid sites were identified for new disulfide bridge generation.

Deletion Mutants

Thermostable proteins have shorter loops that connect their structural elements than typical proteins. Our sequence alignment of CBH I, with its close homologs, suggests that the following residues may be deleted without significantly affecting its function. These loops exhibited high mobility as well. Three loops were identified, but these modifications were considered high risk (buried hydrophobic regions may be exposed to solvent upon deletion of a natural loop) and will be saved for future work.

Proline Replacement Mutants

The unique structure of proline dictates that fewer degrees of freedom are allowed around the alpha carbon that most other amino acids. The result of this structure is that peptides tend to loose flexibility in regions rich with proline. In order to assess possible sites for replacement of existing amino acids with proline, the phi/psi angles of candidate amino acid sites must conform with those consistent with proline. Each new site must also be evaluated for allowable side chain interactions and assurance that interactions with substrate are not altered. Seventeen amino acid sites were identified for proline replacement (See Table 2).

Example 6

Nucleic Acid Sequence of a Variant Exoglucanase

Figure 4:
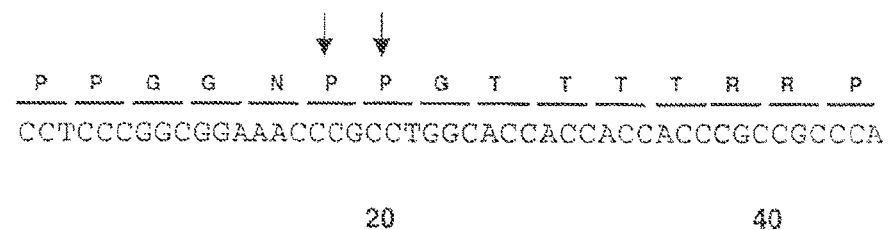
FIG. 4. Nucleotide sequence, SEQ ID NO: 1, coding the linker region, SEQ ID NO: 2, of the CBH I protein, showing additional proline residues that affect conformation of linker region in the protein structure.

The present example demonstrates the utility of providing a nucleic acid molecule having a nucleic acid sequence that has a sequence 5'-_GGCGGAAACCCGC_ _CT_ GGCAC-CACC-3' (SEQ ID NO: 3). The identified nucleic acid sequence presents a novel linker region nucleic acid sequence that differs from previously reported nucleic acid sequence by the addition of one codon, and the alteration of an adjacent codon, both encoding a proline (See FIG. 4). In some aspects, a nucleic acid molecule encoding a cellobiohydrolase that comprises a linker region of about 6 to 20 amino acids in length as identified here is provided.

TABLE 2

Proline mutations to improve thermal tolerance

| Mutation | Native sequence and mutatgenic oligonucleotide |
| --- | --- |
| SEQ ID NO: 10<br>S8P-native sense strand | 5'-GCACTCTCCAATCGGAGACTCACCCG-3' |
| SEQ ID NO: 11<br>Mutagenic sense strand | 5'-GCACTCTCCAACCGGAGACTCACCCG-3' |
| SEQ ID NO: 12<br>Mutagenic anti-sense strand | 5'-CGGGTGAGTCTCCGGTTGGAGAGTGC-3' |
| SEQ ID NO: 13<br>N27P-native sense strand | 5'-GGCACGTGCACTCAACAGACAGGCTCCG-3' |
| SEQ ID NO: 14<br>Mutagenic sense strand | 5'-GGCACGTGCACTCCACAGACAGGCTCCG-3' |
| SEQ ID NO: 15<br>Mutagenic anti-sense strand | 5'-CGGAGCCTGTCTGTGGAGTGCACGTGCC-3' |
| SEQ ID NO: 16<br>A43P-native sense strand | 5'-GGCGCTGGACTCACGCTACGAACAGCAGCACG-3' |
| SEQ ID NO: 17<br>Mutagenic sense strand | 5'-GGCGCTGGACTCACCCTACGAACAGCAGCACG-3' |
| SEQ ID NO: 18<br>Mutagenic anti-sense strand | 5'-CGTGCTGCTGTTCGTAGGGTGAGTCCAGCGCC-3' |
| SEQ ID NO: 19<br>G75P-native sense strand | 5'-GCTGTCTGGACGGTGCCGCCTACGCG-3' |
| SEQ ID NO: 20<br>Mutagenic sense strand | 5'-GCTGTCTGGACCCTGCCGCCTACGCG-3' |
| SEQ ID NO: 21<br>Mutagenic anti-sense strand | 5'-CGCGTAGGCGGCAGGGTCCAGACAGC-3' |
| SEQ ID NO: 22<br>G94P-native sense strand | 5'-GCCTCTCCATTGGCTTTGTCACCC-3' |
| SEQ ID NO: 23<br>Mutagenic sense strand | 5'-GCCTCTCCATTCCCTTTGTCACCC-3' |
| SEQ ID NO: 24<br>Mutagenic anti-sense strand | 5'-GGGTGACAAAGGGAATGGAGAGGC-3' |
| SEQ ID NO: 25<br>E190P-native sense strand | 5'-GGCCAACGTTGAGGGCTGGGAGCC-3' |
| SEQ ID NO: 26<br>Mutagenic sense strand | 5'-GGCCAACGTTCCGGGCTGGGAGCC-3' |
| SEQ ID NO: 27<br>Mutagenic anti-sense strand | 5'-GGCTCCCAGCCCGGAACGTTGGCC-3' |
| SEQ ID NO: 28<br>S195P-native sense strand | 5'-GGCTGGGAGCCGTCATCCAACAACGCG-3' |
| SEQ ID NO: 29<br>Mutagenic sense strand | 5'-GGCTGGGAGCCGCCATCCAACAACGCG-3' |
| SEQ ID NO: 30<br>Mutagenic anti-sense strand | 5'-CGCGTTGTTGGATGGCGGCTCCCAGCC-3' |
| SEQ ID NO: 31<br>K287P-native sense strand | 5'-CGATACCACCAAGAAATTGACCGT-TGTCACCC-3' |

TABLE 2-continued

Proline mutations to improve thermal tolerance

| Mutation | Native sequence and mutatgenic oligonucleotide |
|---|---|
| SEQ ID NO: 32<br>Mutagenic sense strand | 5'-CGATACCACCAAGCCATTGA-CCGTTGTCACCC-3' |
| SEQ ID NO: 33<br>Mutagenic anti-sense strand | 5'-GGGTGACAACGGTCAATGGCTTGGTGGTATCG-3' |
| SEQ ID NO: 34<br>A299P-native sense strand | 5'-CGAGACGTCGGGTGCCATCAACCGATAC-3' |
| SEQ ID NO: 35<br>Mutagenic sense strand | 5'-CGAGACGTCGGGTCCCATCAACCGATAC-3' |
| SEQ ID NO: 36<br>Mutagenic anti-sense strand | 5'-GTATCGGTTGATGGGACCCGACGTCTCG-3' |
| SEQ ID NO: 37<br>Q312P/N315P-native sense strand | 5'-GGCGTCACTTTCCAGCAGCCCAACGCCGAGCTTGG-3' |
| SEQ ID NO: 38<br>Mutagenic sense strand | 5'-GGCGTCACTTTCCCGCAGCCCCCGCCGAGCTTGG-3' |
| SEQ ID NO: 39<br>Mutagenic anti-sense strand | 5'-CCAAGCTCGGCGGGGGGCTGCGGGAAAGTGACGCC-3' |
| SEQ ID NO: 40<br>G359P-native sense strand | 5'-GGCTACCTCTGGCGGCATGGTTCTGG-3' |
| SEQ ID NO: 41<br>Mutagenic sense strand | 5'-GGCTACCTCTCCCGGCATGGTTCTGG-3' |
| SEQ ID NO: 42<br>Mutagenic anti-sense strand | 5'-CCAGAACCATGCCGGGAGAGGTAGCC-3' |
| SEQ ID NO: 43<br>S398P/S401P-native sense strand | 5'-GCGGAAGCTGCTCCACCAGCTCCGGTGTCCCTGC-3' |
| SEQ ID NO: 44<br>Mutagenic sense strand | 5'-GCGGAAGCTGCCCCACCAGCCCCGGTGTCCCTGC-3' |
| SEQ ID NO: 45<br>Mutagenic anti-sense strand | 5'-GCAGGGACACCGGGGCTGGTGGGGCAGCTTCCGC-3' |
| SEQ ID NO: 46<br>A414P-native sense strand | 5'-GTCTCCCAACGCCAAGGTCACC-3' |
| SEQ ID NO: 47<br>Mutagenic sense strand | 5'-GTCTCCCAACCCCAAGGTCACC-3' |
| SEQ ID NO: 48<br>Mutagenic anti-sense strand | 5'-GGTGACCTTGGGGTTGGGAGAC-3' |
| SEQ ID NO: 49<br>N431P/S433 P-native sense strand | 5'-GGCAGCACCGGCAACCCTAGCGGCGGCAACCC-3' |
| SEQ ID NO: 50<br>Mutagenic sense strand | 5'-GGCAGCACCGGCCCCCCTCCCGGCGGCAACCC-3' |
| SEQ ID NO: 51<br>Mutagenic anti-sense strand | 5'-GGGTTGCCGCCGGGAGGGGGCCGGTGCTGCC-3' |

TABLE 3

Mutation to remove peptide strain

| Mutation site | Native sequence and mutagenic oligonucleotide |
|---|---|
| SEQ ID NO: 52<br>S99G-native sense strand | 5'-GGCTTTGTCACCCAGTCTGCGCAGAAGAACGTTGGC-3' |
| SE ID NO: 53<br>Mutagenic sense strand | 5-GGCTTTGTCACCCAGGGTGCGCAGAAGAACGTTGGC-3' |

TABLE 3-continued

Mutation to remove peptide strain

| Mutation site | Native sequence and mutagenic oligonucleotide |
|---|---|
| SEQ ID NO: 54<br>Mutagenic anti-sense strand | 5'-GCCAACGTTCTTCTGCGCACCCTGGGTGACAAAGCC-3' |

TABLE 3b

Y245G analogs to remove product inhibition

| Mutation site | Native sequence and mutatgenic oligonucleotide |
|---|---|
| SEQ ID NO: 55<br>R251A-native sense strand | 5'-CCGATAACAGATATGGCGGC-3' |
| SEQ ID NO: 56<br>Mutagenic sense strand | 5'-CCGATAACGCCTATGGCGGC-3' |
| SEQ ID NO: 57<br>Mutagenic anti-sense strand | 5'-GCCGCCATAGGCGTTATCGG-3' |
| SEQ ID NO: 58<br>R394A-native sense strand | 5'-CCCGGTGCCGTGCCGCGGAAGCTGCTCCACC-3' |
| SEQ ID NO: 59<br>Mutagenic sense strand | 5'-CCCGGTGCCGTGGGCCGGAAGCTGCTCCACC-3' |
| SEQ ID NO: 60<br>Mutagenic anti-sense strand | 5'-GGTGGAGCAGCTTCCGGCCACGGCACCGGG-3' |
| SEQ ID NO: 61<br>F338A-native sense strand | 5'-GCTGAGGAGGCAGAATTCGGCGGATCCTCTTTCTC-3' |
| SEQ ID NO: 62<br>Mutagenic sense strand | 5'-GCTGAGGAGGCAGAAGCCGGCGGATCCTCTTTCTC-3-' |
| SEQ ID NO: 63<br>Mutagenic anti-sense strand | 5'-GAGAAAGAGGATCCGCCGGCTTCTGCCTCCTCAGC-3' |
| SEQ ID NO: 64<br>R267A-native sense strand | 5'-GGAACCCATACCGCCTGGGCAACACCAGC-3' |
| SEQ ID NO: 65<br>Mutagenic sense strand | 5'-GGAACCCATACGCCCTGGGCAACACCAGC-3' |
| SEQ ID NO: 66<br>Mutagenic anti-sense strand | 5'-GCTGGTGTTGCCCAGGGCGTATGGGTTCC-3' |
| SEQ ID NO: 67<br>E385A-native sense strand | 5'-CCTACCCGACAAACGAGACCTCCTCCACACCCGG-3' |
| SEQ ID NO: 68<br>Mutagenic sense strand | 5'-CCTACCCGACAAACGCCACCTCCTCCACACCCGG-3' |
| SEQ ID NO: 69<br>Mutagenic anti-sense strand | 5'-CCGGGTGTGGAGGAGGTGGCGTTTGTCGGGTAGG-3' |

TABLE 4

N to A mutations to remove glycosylation

| Mutant | Native sequence and mutagenic oligonucleotide |
|---|---|
| SEQ ID NO: 70<br>N45A-native sense strand | 5'-GGACTCACGCTACGAACAGCAGCACGAACTGC-3' |
| SEQ ID NO: 71<br>Mutagenic sense strand | 5'-GGACTCACGCTACGGCCAGCAGCACGAACTGC-3' |
| SEQ ID NO: 72<br>Mutagenic anit-sense strand | 5'-GCAGTTCGTGCTGCTGGCCGTAGCGTGAGTCC-3' |

TABLE 4-continued

N to A mutations to remove glycosylation

| Mutant | Native sequence and mutagenic oligonucleotide |
| --- | --- |
| SEQ ID NO: 73<br>N270A-native sense strand | 5'-CCCATACCGCCTGGGCAACACCAGCTTCTACGGCCC-3' |
| SEQ ID NO: 74<br>Mutagenic sense strand | 5'-CCCATACCGCCTGGGCGCCACCAGCTTCTACGGCCC-3' |
| SEQ ID NO: 75<br>Mutagenic anti-sense strand | 5'-GGGCCGTAGAAGCTGGTGCGCCCAGGCGGTATGGG-3' |
| SEQ ID NO: 76<br>N384A-native sense strand | 5'-GGACTCCACCTACCCGACAAACGAGACCTCCTCCACACCCG-3' |
| SEQ ID NO: 77<br>Mutagenic sense strand | 5'-GGACTCCACCTACCCGACAGCCGAGACCTCCTCCACACCCG-3' |
| SEQ ID NO: 78<br>Mutagenic anti-sense strand | 5'-CGGGTGTGGAGGAGGTCTCGGCTGTCGGGTAGGTGGAGTCC-3' |

TABLE 5

Helix capping mutations to improve thermal tolerance

| Mutant | Native sequence and mutagenic oligonucleotide |
| --- | --- |
| SEQ ID NO: 79<br>EE37R-native sense strand | 5'-GCTGAGGAGGCAGAATTCGGCGG-3' |
| SEQ ID NO: 80<br>Mutagenic sense strand | 5'-GCTGAGGAGGCACGCTTCGGCGG-3' |
| SEQ ID NO: 81<br>Mutagenic anti-sense strand | 5'-CCGCCGAAGCGTGCCTCCTCAGC-3' |
| SEQ ID NO: 82<br>N327D-native sense strand | 5'-GGCAACGAGCTCAACGATGATTACTGC-3' |
| SEQ ID NO: 83<br>Mutagenic sense strand | 5'-GGCAACGAGCTCGACGATGATTACTGC-3' |
| SEQ ID NO: 84<br>Mutagenic anti-sense strand | 5'-GCAGTAATCATCGTCGAGCTCGTTGCC-3' |
| SEQ ID NO: 85<br>A405D-native sense strand | 5'-CCGGTGTCCCTGCTCAGGTCGAATCTCAGTCT-CCC-3' |
| SEQ ID NO: 86<br>Mutagenic sense strand | 5'-CCGGTGTCCCTGATCAGGTCGAATCTCAGTCTCCC-3' |
| SEQ ID NO: 87<br>Mutagenic anti-sense strand | 5'-GGGAGACTGAGATTCGACCTGATCAGGGACACCGG-3' |
| SEQ ID NO: 88<br>Q410R-native sense strand | 5'-GCTCAGGTCGAATCTCAGTCTCCCAACGCC-3' |
| SEQ ID NO: 89<br>Mutagenic sense strand | 5'-GCTCAGGTCGAATCTCGCTCTCCCAACGCC-3' |
| SEQ ID NO: 90<br>Mutagenic anti-sense strand | 5'-GGCGTTGGGAGAGCGAGATTCGACCTGAGC-3' |
| SEQ ID NO: 91<br>N64D-native sense strand | 5'-CCCTATGTCCTGACAACGAGACCTGCGCG-3' |
| SEQ ID NO: 92<br>Mutagenic sense strand | 5'-CCCTATGTCCTGACGACGAGACCTGCGCG-3' |
| SEQ ID NO: 93<br>Mutagenic anti-sense strand | 5'-CGCGCAGGTCTCGTCGTCAGGACATAGGG-3' |
| SEQ ID NO: 94<br>N64D-native sense strand | 5'-GCTCGACCCTATGTCCTGACAACGAGACCTGCGCGAAGAACTGC-3' |

TABLE 5-continued

Helix capping mutations to improve thermal tolerance

| Mutant | Native sequence and mutagenic oligonucleotide |
|---|---|
| SEQ ID NO: 95<br>Mutagenic sense strand | 5'-GCTCGACCCTATGTCCTGACGACGAGACTGCGCGAAGAACTGC-3' |
| SEQ ID NO: 96<br>Mutagenic anti-sense strand | 5'-GCAGTTCTTCGCGCAGGTCTCGTCGTCAGGACATAGGGTVGAGC-3' |

In Tables 2, 3, 3b, 4 and 5, the amino acid mutations sites are listed in the left column. The first letter in the designation is the amino acid of the native protein based upon IUPAC convention for one-letter codes for amino acids. The number represents the amino acid location as designated from the start of the mature protein (excluding the signal peptide, i.e. QSA . . . ). The letter designation after the number represents the amino acid that will occur as a result of the mutation. For example N64D represents the asparagine at site 64 changed to an aspartic acid. The native sense strand sequence for each site is listed in the right column with the oligonucleotide primers (sense and anti-sense) used to obtain the desired mutation below the native sequence in each case. In addition the codon for the targeted amino acid is bolded and the nucleotide substitutions in the mutagenic primers underlined. In some cases only one nucleotide substitution was required the make the desired change, and in others 2 or 3 substitutions were required. In a few cases, double mutations were made with a single mutagenic oligonucleotide.

Example 7

Figure 5:
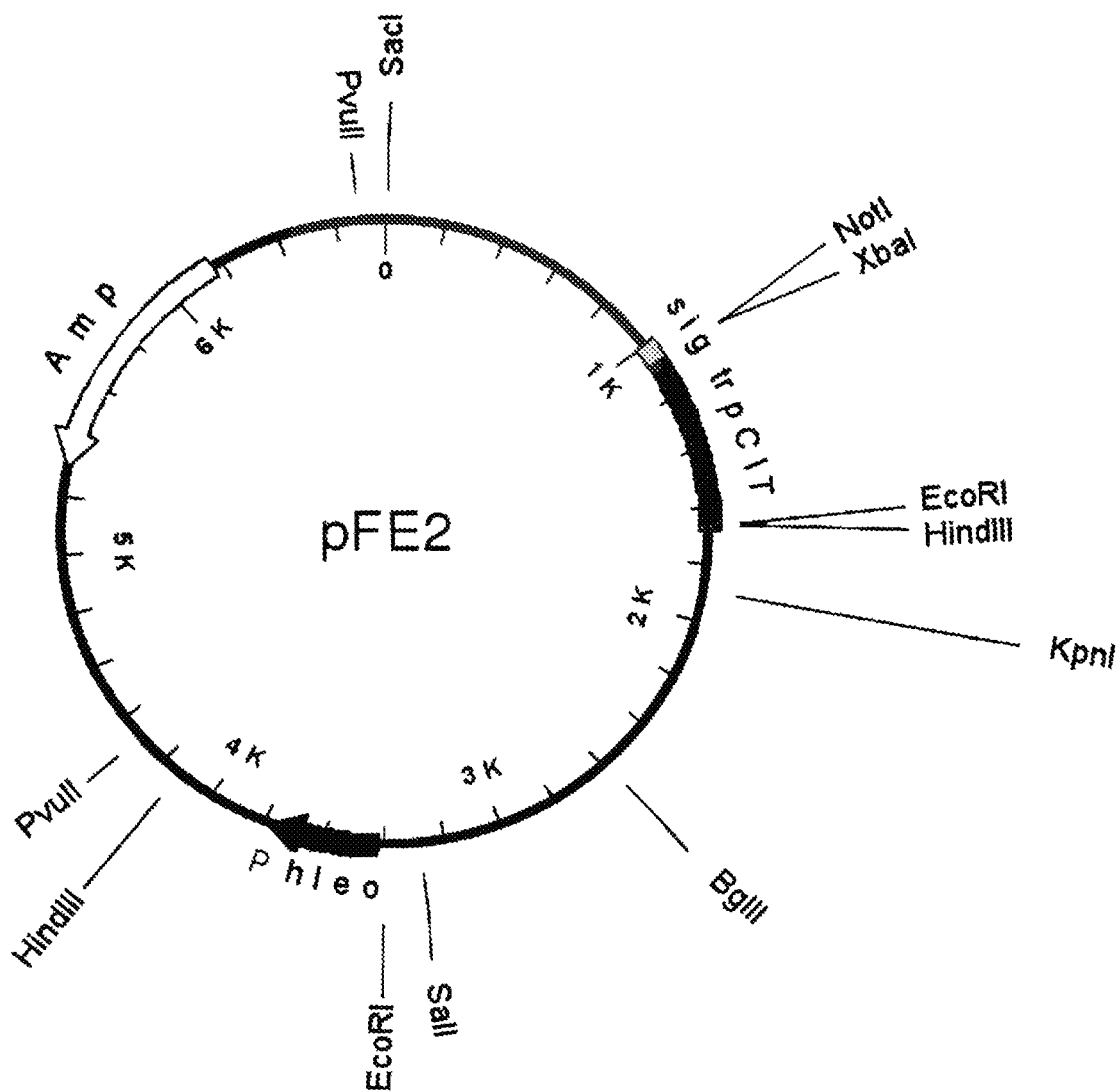
FIG. 5. Plasmid map and features of expression *E. coli/Aspergillus* shuttle vector pFE2.

The following example provides analysis of exemplary enzymes modified as described above.
Materials and Methods
Acquisition of the Cellobiohydrolase Genes The cel7a gene from *Penicillium funiculosum* (ATCC62998) was acquired from genomic DNA using PCR with primers based on the published GenBank sequence for *P. funiculosum* xylanase/cellobiohydrolase (AJ312295). The resulting PCR product was cloned into the vector pGEM so that it contained the entire cel7a coding sequence including the wild type signal sequence. This plasmid was then used to construct the pFE2 expression vector for *A. awamori* and to perform site-directed mutations of N-linked glycosylation sites (FIG. 5). Using this approach, primers were designed that isolated the translated portion of the cel7a gene sequence and added convenient restriction enzyme sites for cloning. Pfu polymerase, a polymerase with proofreading ability and high fidelity, was obtained from (Stratagene, San Diego, Calif.) and used for all PCR reactions. Inserts containing the cel7a gene were prepared by gel purification of the PCR products followed by restriction digestion and directional cloning into the appropriate expression vector. Confirmation of the cel7a gene and the resultant gene product was based on DNA sequencing. The cel7a gene from *Trichoderma reesei* was acquired from cDNA as described above.

Figure 6:
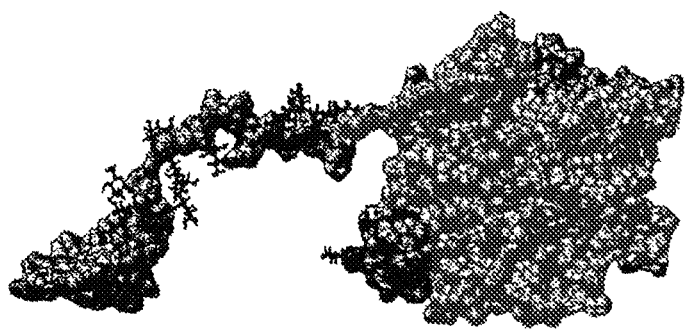
FIG. 6. CHARMM optimized structure of Cel7A. The binding domain (CBD) is shown on the left connected to the catalytic domain on the right through a glycosylated linker. O-linked glycans are illustrated on the linker and N-linked glycans are black and on the catalytic domain.

Modified proteins were produced from genes cloned from either cDNA or genomic DNA and expressed in *Aspergillus awamori* under the control of the *A. niger* glucoamylase promoter using the *E. coli/Aspergillus* shuttle vector pFE2 (FIG. 6). The mature *P. funiculosum* enzyme consists of a 504-residue glycoprotein with a calculated molecular weight of 52,436 Daltons, whereas the mature *T. reesei* enzyme consists of a 497-residue glycoprotein with a calculated molecular weight of 52,247 Daltons (Table 6). The *T. reesei* enzyme has three N-linked glycosylation sites (N45, N270 and N384) with an unlinked motif at N64. Similarly, the *P. funiculosum* enzyme has three N-linked sites at positions N45, N387 and N430, with a potential motif at N194. In order to evaluate the role of N-linked glycosylation on the activity and stability of these enzymes, we established a library of mutants that were systematically modified by the elimination of N-linked glycosylation motifs. Following the expression and purification of each mutant, we conducted an examination of the thermal stability, binding, and kinetic performance on crystalline and amorphous cellulose to establish the relative importance of each site.

TABLE 6

Amino acid sequence of Cel7A enzymes from *P. funlculosum* and *T. reesei*.

| Organism | Sequence* and SEQ ID NO |
|---|---|
| *P. funiculosum* Cel7A | malnsfnmyk salllgalla tagaQQIGTY TAETHPSLSW<br>STCKSGGSCT TNSGAITLDA NWRWVHGV<u>NT</u> STNCYTGNTW<br>NSAICDTDAS CAQDCALDGA DYSGTYGI<u>TT</u> SGNSLRLNFV<br>TGSNVGSRTY LMADNTHYQI FDLLNQEFTF TVDVSHLPCG<br>LNGALYFVTM DADGGVSKYP NNKAGAQYGV GYCDSQCPRD<br>LKFIAGQANV EGWTPSANNA NTGIGNHGAC CAELDIWEAN<br>SISEALTPNP CDTPGLSVCT TDACGGTYSS DRYAGTCDPD<br>GCDFNPYRLG VTDFYGSGKT VDTTKPFTVV TQFVTNDGTS<br>TGSLSEIRRY YVQNGVVIPQ PSSKISGISG NVINSDYCAA<br>EISTFGGTAS FSKHGGLTNM AAGMEAGMVL VMSLWDDYAV<br>WMLWLDSTYP T<u>N</u>ATGTPGAA RGTCATTSGD PKTVESQSGS<br>SYVTFSDIRV GPF<u>N</u>STFSGG *SSTGGSTTTT ASRTTTTSAS<br>STSTSSTSTG* TGVAGHWGQ<u>C GGQGWTGPTT CVSGTTCTVV</u><br><u>NPYYSQCL</u><br>SEQ ID NO: 110 |

TABLE 6-continued

Amino acid sequence of Cel7A enzymes
from *P. funlculosum* and *T. reesei*.

| Organism | Sequence* and SEQ ID NO |
|---|---|
| *T. reesei* Cel7A | myrklavisa flataraQSA CTLQSETHPP LTWQKCSSGG |
| | TCTQQTGSVV IDANWRWTHA TNSSTNCYDG NTWSSTLCPD |
| | NETCAKNCCL DGAAYASTYG VTTSGNSLSI GFVTQSAQKN |
| | VGARLYLMAS DTTYQEFTLL GNEFSFDVDV SQLPCGLNGA |
| | LYFVSMDADG GVSKYPTNTA GAKYGTGYCD SQCPRDLKFI |
| | NGQANVEGWE PSSNNANTGI GGHGSCCSEM DIWEANSISE |
| | ALTPHPCTTV GQEICEGDGC GGTYSDNRYG GTCDPDGCDW |
| | NPYRLGNTSF YGPGSSFTLD TTKKLTVVTQ FETSGAINRY |
| | YVQNGVTFQQ PNAELGSYSG NELNDDYCTA EEAEFGGSSF |
| | SDKGGLTQFK KATSGGMVLV MSLWDDYYAN MLWLDSTYPT |
| | NETSSTPGAV RGSCSTSSGV PAQVESQSPN AKVTFSNIKF |
| | GPIGSTGNPS GGNPPG*GNPP GTTTTRRPAT TTGSSPGPTQ* |
| | SHYGQCGGIG YSGFTVCASG TTCQVLNPYY SQCL |
| | SEQ ID NO: 111 |

* Cellulose binding modules are underlined, the linker domains in italics, and the signal sequences in lower case letters. N-linked glycosylation sites modified in this study are in bold and double underlined on the respective enzymes. Linker domains can be modified to increase O-linked glycosylation.

Culture and Growth Conditions

*E. coli* DH5α was cultured in LB (Luria Broth) at 37° C., 250 rpm whereas *A. awamori* ATCC22342 and *P. funiculosum* ATCC62998 were grown in CM media (per liter: glucose 10 g, yeast extract 5 g, tryptone 5 g, and 50 mL Clutterbuck's salts solution, pH 7.5) at 29° C., 250 rpm. Clutterbuck's salts contain 120 g/L Na2NO3, 10.4 g/L KCl, 10.4 g/L MgSO$_4$.7H$_2$O and 30.4 g/L KH$_2$PO$_4$. For the selection and maintenance of pFE2 and its derivatives, antibiotics were supplemented to the media at the following concentrations: Zeocin (Z or Zeo), 170 µg/mL for the initial selection of *A. awamori* transformants, 300 µg/mL for the growth of transformants for cellulase production; Ampicillin (Amp), 100 µg/mL for *E. coli*. For agar media, Bacto Agar (Difco) was added to CM at 2% and LB at 1.5%.

Modification of N-Linked Glycosylation Sites

Mutants with targeted amino acid substitutions were generated using the QuickChange™ Site-Directed Mutagenesis Kit (Stratagene, San Diego, Calif.). Mutagenic primers, containing the desired mutation were designed and synthesized at Macromolecular Resources (Colorado State University, Fort Collins, Colo.). The double-stranded DNA vector pGEM with cella insert, combined with the two complementary synthetic oligonucleotide primers containing the desired mutation, and underwent temperature cycling with PftiTurbo DNA polymerase for primer extension and amplification. Incorporation of the oligonucleotide primers generated the mutated gene. Following temperature cycling, the product was treated with DpnI to digest the parental methylated DNA template, and the PCR product was used to transform Epicurian Coli XL1-Blue supercompetent cells (Stratagene, San Diego, Calif.) or *E. coli* DH5α. Mutations were confirmed by DNA sequencing.

Cellobiohydrolase Purification

The purification of all of the rCel7A enzymes was performed as described above. Fungal hyphae were removed from 1-L shake flask growths by passing the broth first through miracloth and then through glass fiber filters. The broth was concentrated and extensively diafiltered with 20 mM Bis-Tris pH 5.8 buffer and applied to a HiPrep 16/10 DEAE FF column (Amersham Biosciences) equilibrated with 50 mM Bis-Tris, pH 5.8 buffer with a flow rate of 10 mL/min. The column was washed extensively with equilibration buffer and the bound fraction eluted with a linear gradient of 0 to 0.5 M NaCl in the same equilibration buffer. Fractions containing the rCel7A enzyme were pooled, concentrated and subjected to size exclusion chromatography using a Superose 12 Prep grade 35/600 column in 20 mM acetate, 100 mM NaCl pH 5 buffer. The purity was confirmed as a single band using a NuPage 4-12% Bis-Tris gradient gel and MOPS-SDS buffer (Invitrogen) following the manufactures recommended conditions.

Differential Scanning Microcalorimetry.

Protein stability was determined by differential scanning microcalorimetry using a Microcal model VP-DSC calorimeter (Microcal, Inc., Northampton, Mass.), with data analysis by means of Origin for DSC software (Microcal). Thermograms were collected for samples containing 50 µg/mL protein at pH 5.0 in 20 mM sodium acetate with 100 mM NaCl. The calorimeter scan rate was 60° C./h.

Production of Bacterial Cellulose

Bacterial cellulose (BC) was produced in static cultures of *Gluconacetobacter xylinus* sbsp *sucrofermentans* (ATCC 700178) in Hestrin Schramm medium with 1% (v/v) ethanol. The initial inoculum was prepared by growing frozen *G. xylinus* culture in 50 mL of the same medium (HS+1% EtOH) at 26° C. for 3 days under static conditions. At the end of the three days, the culture flask was shaken vigorously to remove the cells from the pellicle. The cells in the supernatant were pelletized and used to inoculate 75 mL media in 750 mL rectangular tissue culture flasks. Production cultures were incubated at 26° C. for 5-7 days without agitation. At the end of the production period, the cells were re-pelletized and used in fresh media for growing subsequent batches of BC. The BC pellicles were washed according to a protocol outlined by Helbert et. al with the following modifications. Following neutralization from the alkali wash, the cellulose pellicles were incubated in a 0.3% bleach solution (in 4 mM sodium acetate buffer) for 2 hours at 70° C. The pellicles were rinsed three times with distilled water to remove the bleach solution. Following the final water rinse, the pellicles were resuspended in 5 mM sodium acetate, pH 5.0 buffer with 0.04% NaNs and homogenized in a food processor. A final concentration of 1.9 mg/mL (standard deviation of 0.12 mg/mL) was determined from triplicate oven dry weights of 3 mL suspensions. The stock BC suspension is stored at 4° C.

Cellulose Hydrolysis Time Course Experiments.

Reactions containing 1.0 µM cellulase and 1.0 mg/mL BC in 0.25 mL reaction volumes were conducted at 38° C. Triplicate reactions were incubated for each of 0.25, 0.5, 1, 2 and 4 hour durations. Each reaction was setup by preparing the appropriate dilution of cellulase in 1.5 mL microcentrifuge tubes. The BC was pre-incubated at 38° C. for a minimum of 30 minutes. The reactions were initiated by addition of the preincubated substrate and terminated by separating the liquid and solid phase by filtration using a manifold filtration system equipped with a 96-well 1.0 μM glass fiber filter frit (Innovative Microplate, Chicopee, Mass.). The liquid phase was assayed for reducing sugar concentration by the disodium-2,2'-bicinchoninate method using cellobiose for the standard curve.

P. funiculosum Cel7A N-Glycan Analysis by Mass Spectrometry

Oligosaccharide heterogeneity in Aspergillus awamori expressed Cel7A glycoproteins was determined using a combination of nonspecific proteolysis, deglycosylation, and Direct Infusion Electrospray ionization mass spectrometry (ESI-MS).

Results

Expression of Cel7a Genes

Figure 7:
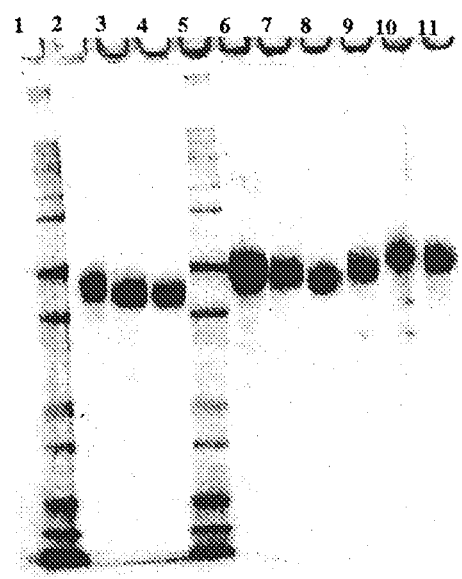
FIG. 7. Invitrogen 4-12% gradient NuPage gel with MOPS buffer. Lane 1) Mark 12 Std, 2) *T. reesei* Cel7A, 3) *T. reesei* N270A, 4) *T. reesei* N384A, 5) Mark 12 Std, 6) *P. funiculosum* Cel7A, 7) *P. funiculosum* N45A, 8) *P. funiculosum* N388A, 9) *P. funiculosum* N430A, 10) *P. funiculosum* A196S, 11) *P. funiculosum* A196T.

The T. reesei and P. funiculosum cel7a genes, as well as the engineered mutant sequences for each, were expressed in A. awamori using their respective signal sequences. The glucoamylase promoter and the TrpC terminator from A. awamori were used to promote and terminate transcription. Using this construct, the recombinant proteins were secreted into the culture medium and purified using column chromatography. The purity of the enzyme preparation and the molecular weights were determined using SDS-PAGE (FIG. 7) and by MALDI-MS (Table 7). The replacement of asparagine with alanine resulted in a lower apparent molecular weight attributable to the removal of glycosylation at that site. In the case of the P. funiculosum enzyme, the replacement of the alanine at site 196 with either threonine or serine resulted in a new N-linked motif at N194. For the T. reesei enzyme, replacement of the asparagine with an alanine at site 45 resulted in an unstable protein product whereas the analogous site for the P. funiculosum produced a stable mutant protein. As described herein, homology models and computer simulations are useful in predicting those sites which are most likely to be successful.

TABLE 7

Characteristics of purified mutant proteins produced in this study.

| A. awamori expressed Cel7A enzyme | Estimated MW SDS-PAGE | Calculated MW | MALDI MW | Theoretical pI | $T_{max}$ (° C.)[1] | Comment |
|---|---|---|---|---|---|---|
| *T. reesei* Cel7A | | | | | | |
| Wild type | 66232 | 52209 | 61835 | 4.51 | 65.4 | Wild type sequence |
| N45A | — | | | | — | Unstable protein/low yield |
| N270A | 64127 | 52068 | 59766 | 4.51 | 65.4 | N-linked site removed |
| N384A | 64127 | 52068 | 60154 | 4.51 | 63.4 | N-linked site removed |
| *P. funiculosum* Cel7A | | | | | | |
| Wild type | 69068 | 52436 | 64228 | 4.56 | 67.5 | Wild type sequence |
| N45A | 69068 | 52393 | 65419 | 4.56 | 67.2 | N-linked site removed |
| N388A | 67054 | 52393 | 63719 | 4.56 | 65.6 | N-linked site removed |
| N430A | 71990 | 52393 | 66641 | 4.56 | 66.6 | N-linked site removed |
| A196S | 75482 | 52452 | 68822 | 4.56 | 66.5 | Added N-link motif for N194 |
| A196T | 73716 | 52466 | | 4.56 | 66.4 | Added N-link motif for N194 |

Differential Scanning Calorimetry Analysis

Figure 8:
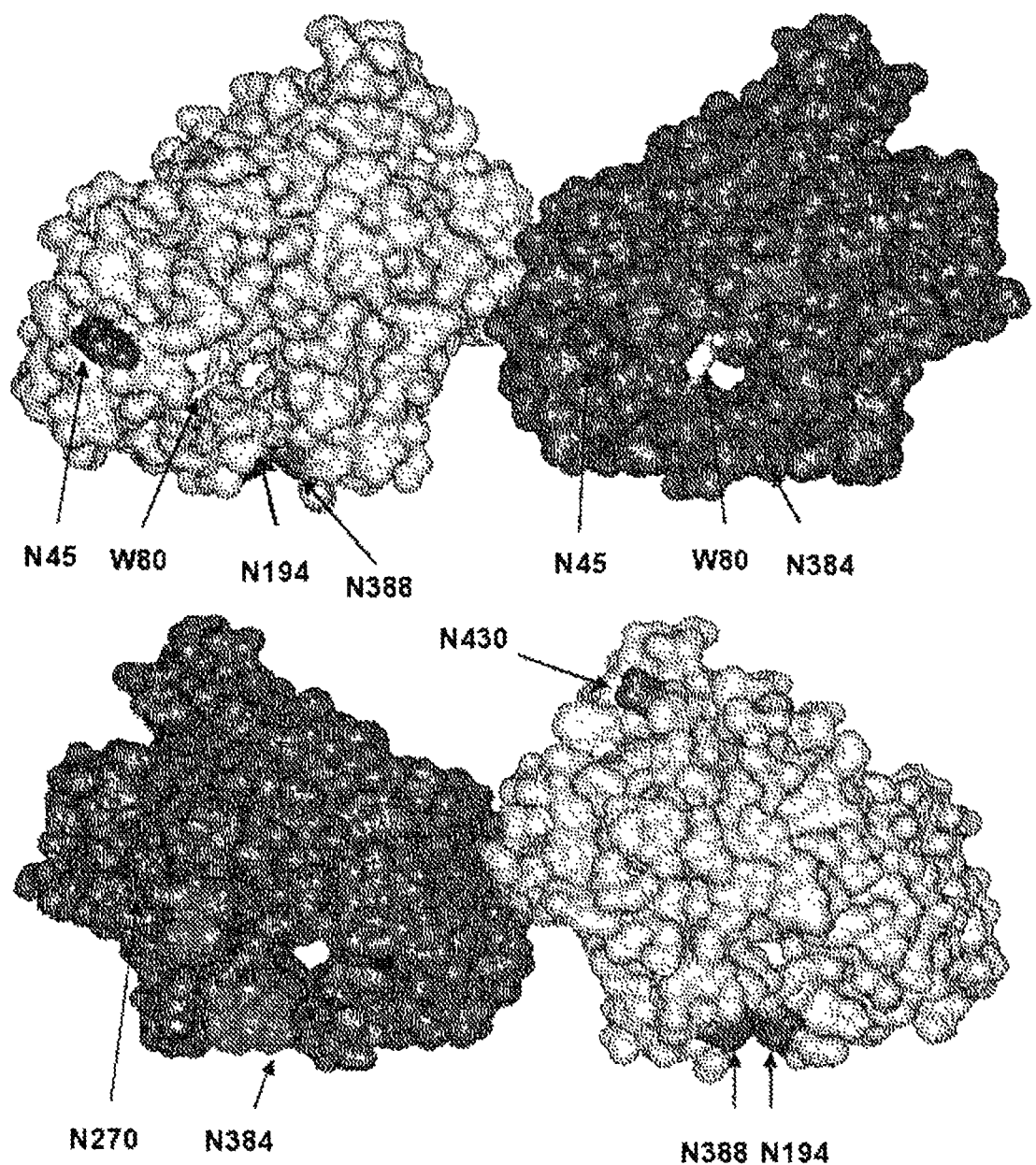
FIG. 8. Comparison of N-linked glycosylation sites based on a structure of the *P. funiculosum* Cel7A enzyme generated using the web based program SWISS-MODEL and the published structure on *T. reesei* Cel7A.
Figure 9:
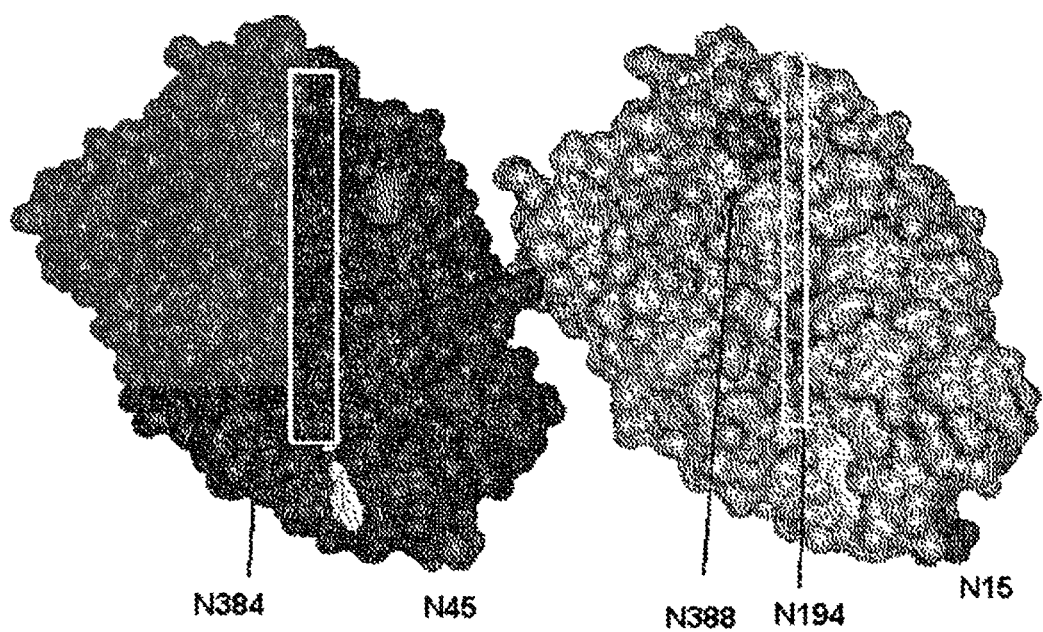
FIG. 9. Another view showing the comparison of N-linked glycosylation sites based on a structure of the *P. funiculosum* Cel7A enzyme generated using the web based program SWISS-MODEL and the published structure on *T. reesei* Cel7A.

Differential Scanning Calorimetry (DSC) was used to evaluate the thermal stability of wild type Cel7 enzymes (purified from T. reesei and P. funiculosum culture broths) and those produced by heterologous expression of the wild type genes in A. awamori. Comparisons of P. funiculosum Cel7A to T. reesei Cel7A enzymes using DSC showed a 1.8° C. difference in thermal transition temperature. The higher thermal transition temperature for the P. funiculosum protein likely indicates either differences in the peptide secondary structure or differences in the extent and nature of glycosylation of the two enzymes (or possibly a combination of both). Analysis of the glycosylation motifs found in the sequences of these two proteins shows similar placement of the N-linked glycosylation sites on the surfaces of the two proteins as illustrated by a homology model of the P. funiculosum enzyme and the published structure for T. reesei Cel7a (lcel). Similarities between the potential glycosylation sites for these two enzymes are illustrated in FIGS. 8 and 9.

Figure 10:
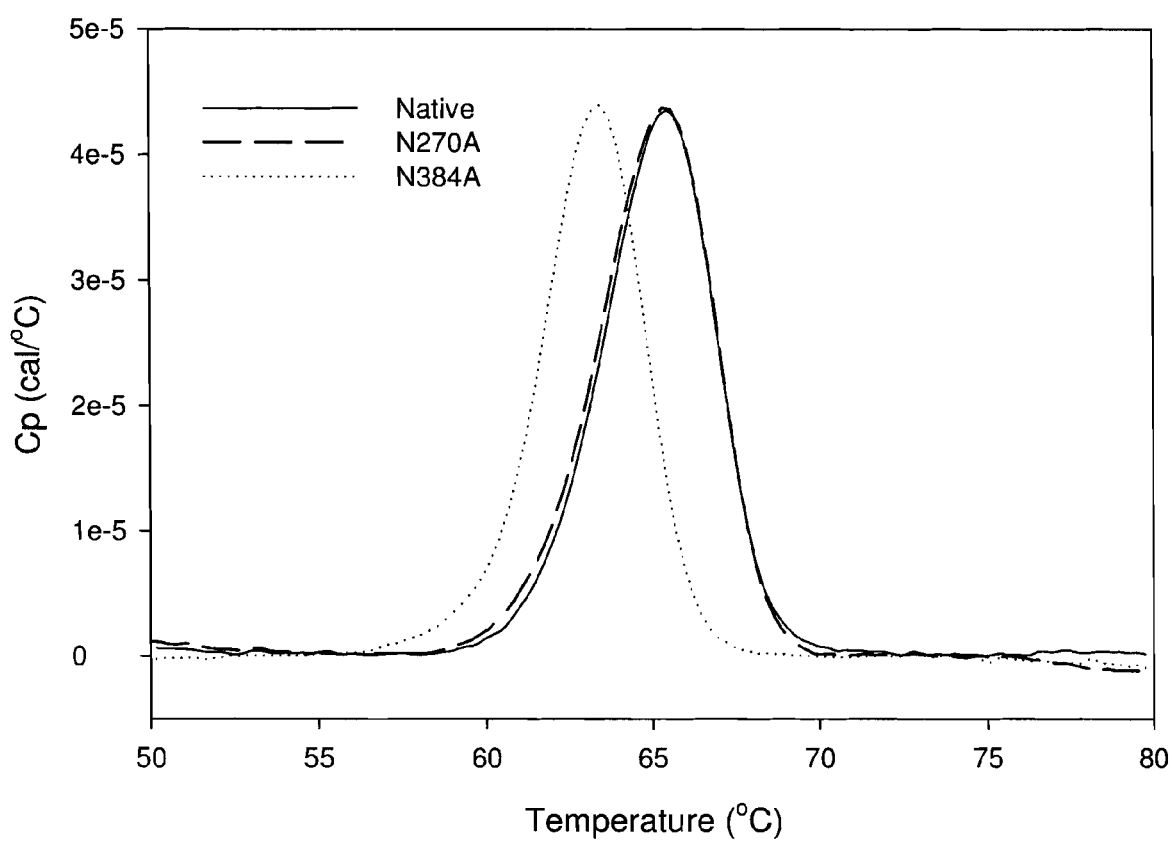
FIG. 10. DSC thermal denaturation curves of recombinant *T. reesei* Cel7A enzymes expressed in *A. awamori* comparing the wild type Cel7A sequence (solid line) to the single site deglycosylation mutants N270A (dashed line) and N384A (dotted line).
Figure 11:
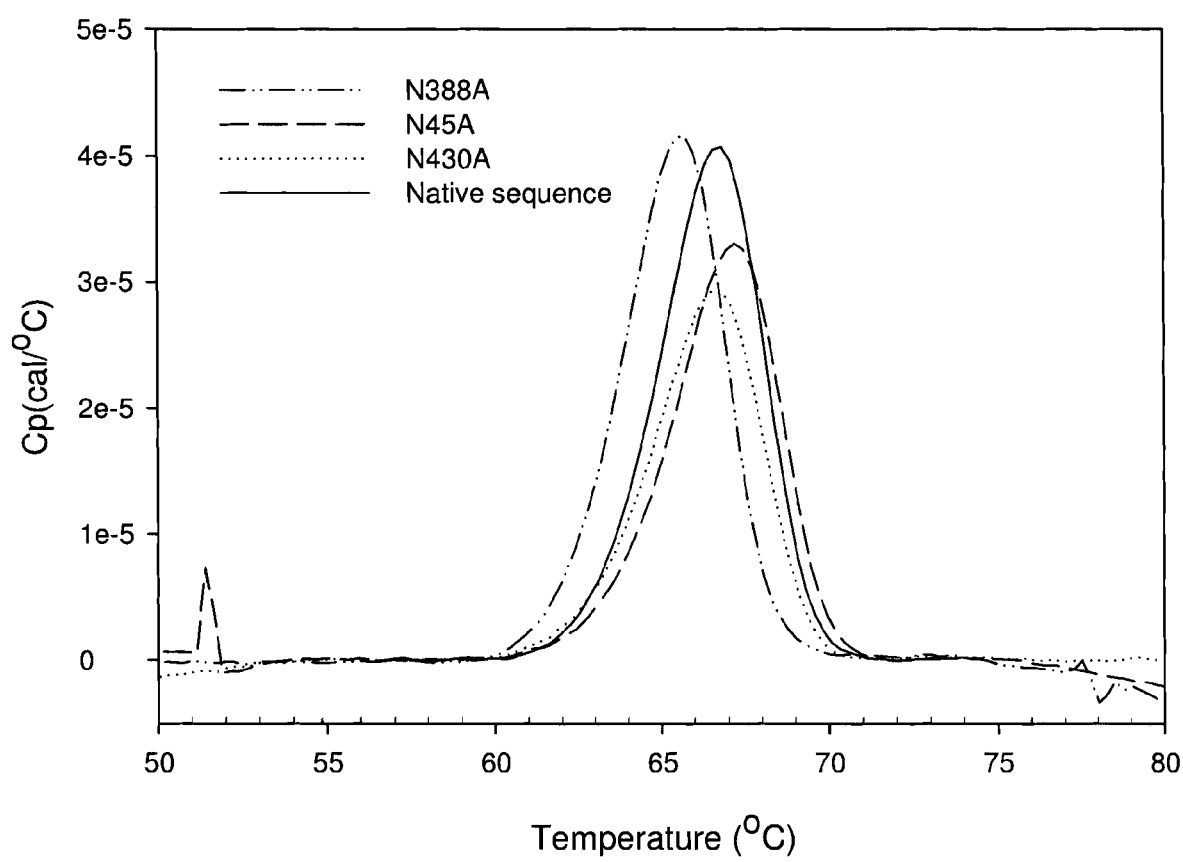
FIG. 11. DSC thermal denaturation curves of recombinant *P. funiculosum* Cel7A enzymes expressed in *A. awamori* comparing the wild type Cel7A sequence (solid line) to the single site deglycosylation mutants N45A (dashed line), N388A (dashed dot line) and N430A (dotted line).
Figure 12:
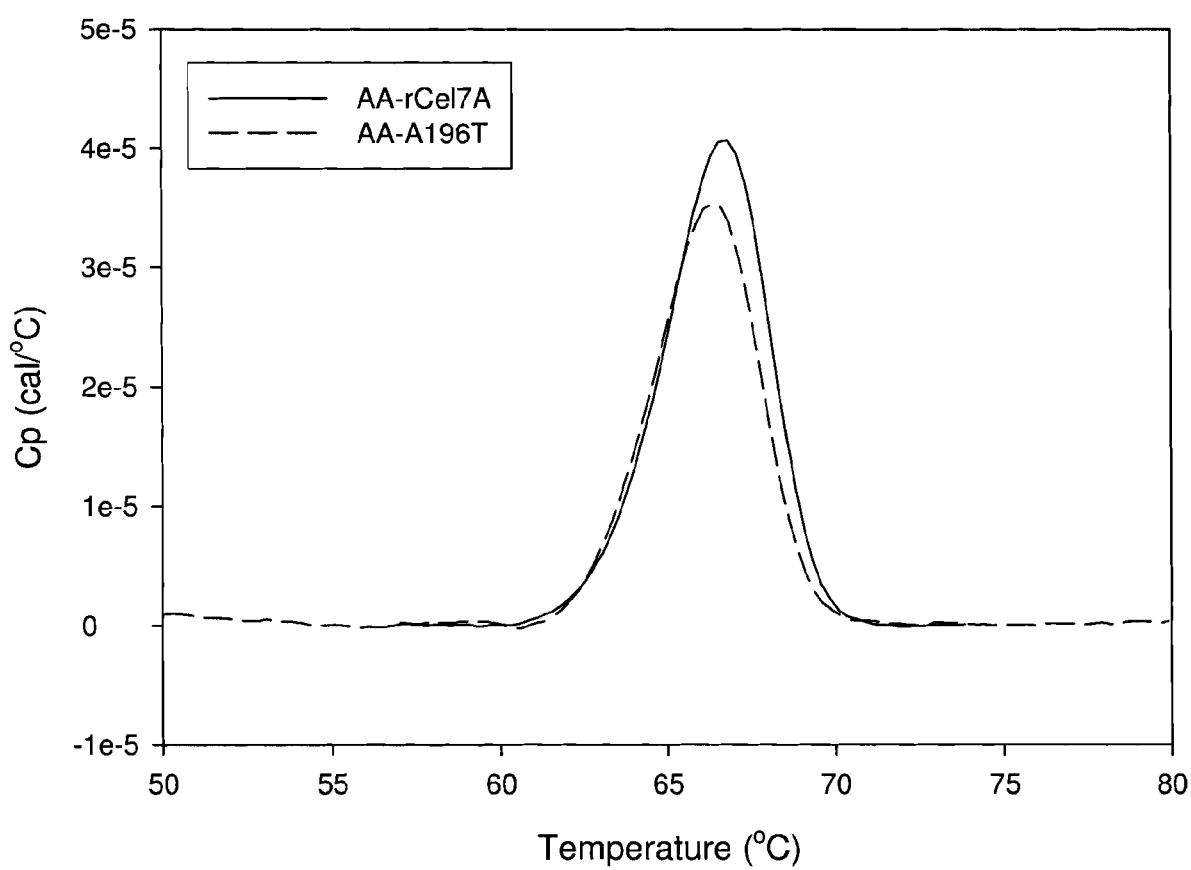
FIG. 12. DSC thermal denaturation curves of recombinant *P. funiculosum* Cel7A enzymes expressed in *A. awamori* comparing the wild type *Aspergillus* expressed Cel7A sequence (solid line) to mutants A196T (dashed line) designed to add N-linked glycosylation at position N194.

Results from DSC studies of the recombinant N-linked glycosylation mutants of T. reesei Cel7A and P. funiculosum Cel7A are illustrated in FIGS. 10 and 11, respectively, and in Table 1. The results shown in these figures show the conserved sensitivity of the N-linked sites directly associated with sites N394 and N388, in T. reesei and P. funiculosum, respectively. Both enzymes are sensitive to the removal of the glycans at this site as illustrated by the shift in thermal denaturation curves corresponding to these mutants compared to the proteins expressed using the wild type genes and the other N-linked mutants. The addition of the N-linked motif at N194 to the *P. funiculosum* enzyme did not result in a difference in thermal denaturation (see FIG. 12).

Thermal Stability Measured by Circular Dichroism

Figure 13:
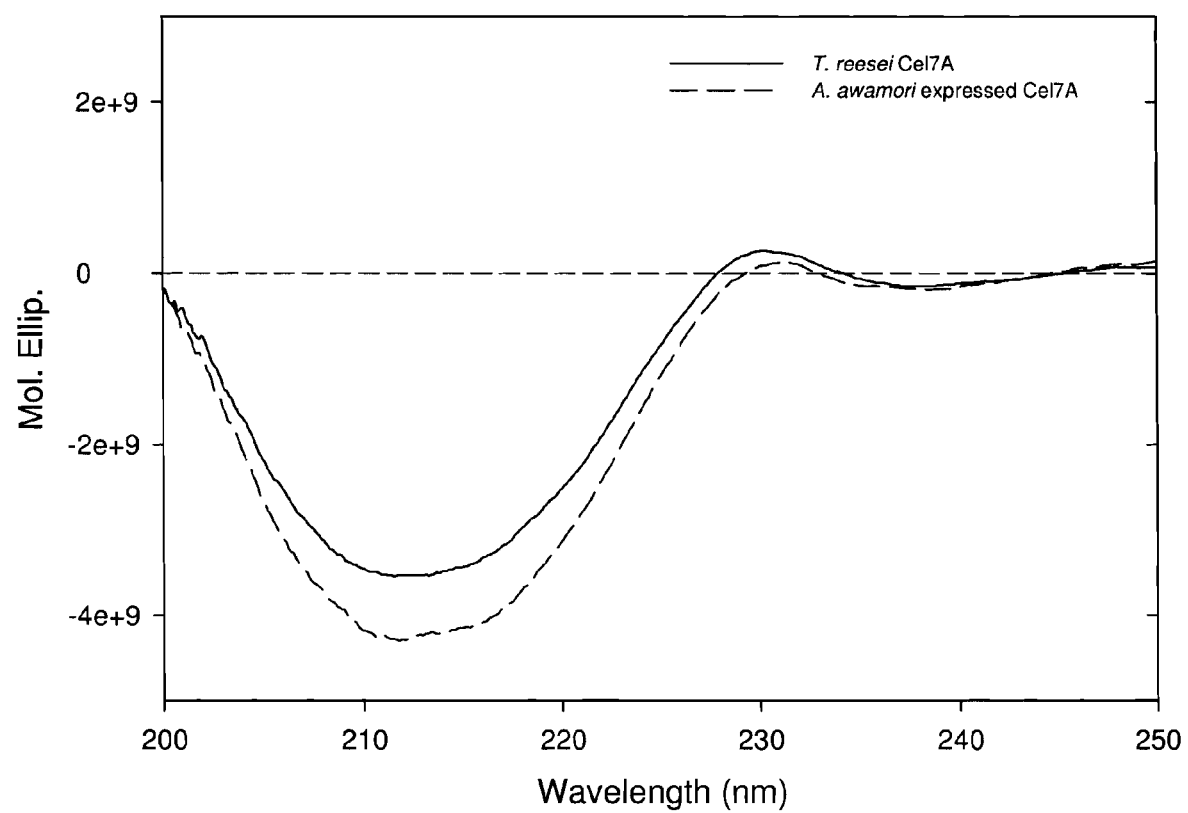
FIG. 13. CD spectrum comparison of wild type and recombinant *T. reesei* Cel7A enzymes expressed in *A. awamori* using a Jasco Model J-715 spectropolarimeter.

The thermal stability of the *A. awamori* expressed proteins was also assessed using circular dichroism (CD) by following changes in the far UV CD region with increasing temperature. The CD signal near 220 nm is generally dominated by peptide groups in helical structures, while the CD measurements near 270 nm monitor aromatic groups fixed in specific orientations due to tertiary structure. Consequently, the combination of these techniques offers a unique set of data characterizing intermediates of the protein folding process. The far UV CD spectra for the *A. awamori*-expressed wild type gene products were nearly identical to spectra obtained for the wild type proteins and similar for all of the mutants tested. The CD spectra for these enzymes show a broad negative peak from 210 to 218 nm, consistent with the structural features of a protein dominated by random coil (FIG. 13). These spectra suggest that there is no significant deviation in the secondary structures of *T. reesei* and *P. funiculosum* Cel7A enzymes expressed in *A. awamori* and processed with their wild type signal sequences, relative to their respective wild type proteins secreted from their original source microorganisms. By following changes over the entire far UV CD region, it was possible to determine whether at high temperatures the protein is losing all of its secondary structure, loses only a portion of its secondary structure, or simply undergoes conformational change involving a change in secondary structure.

Figure 14:
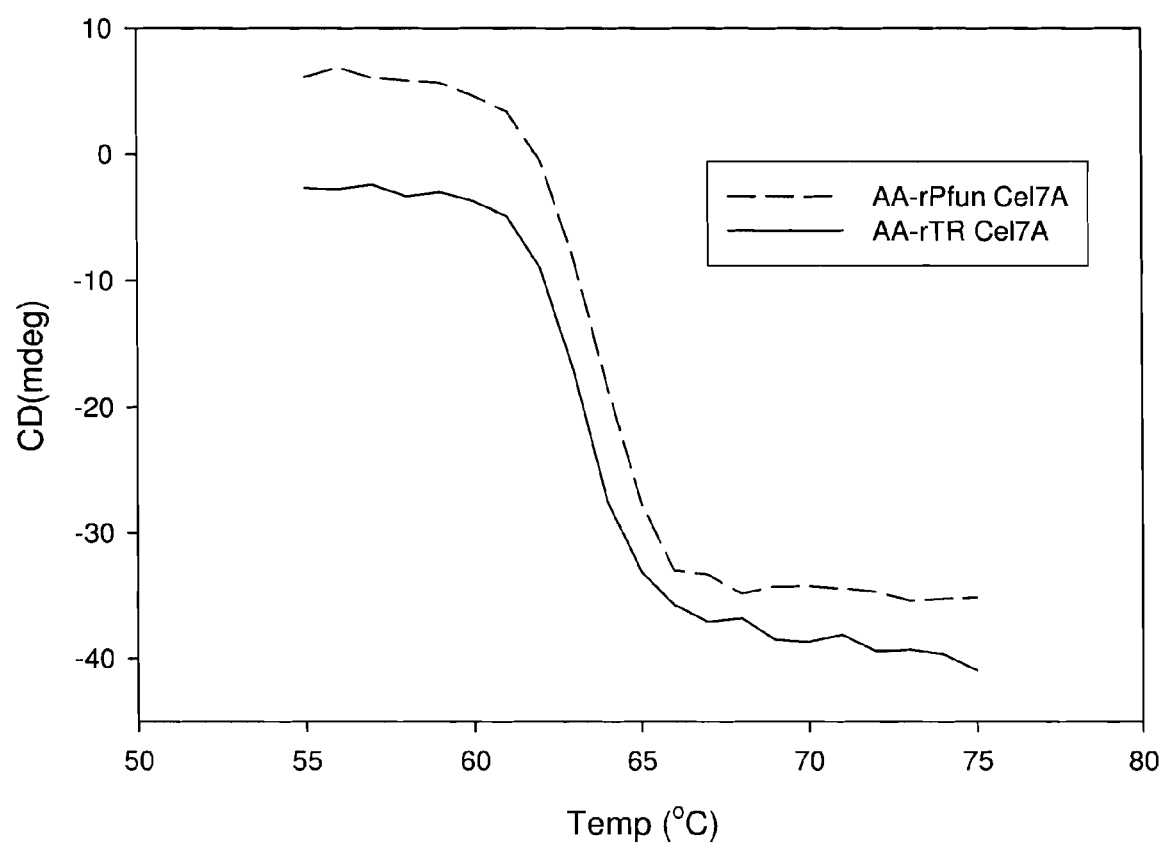
FIG. 14. CD spectrum comparison of the thermal denaturation curves of recombinant *T. reesei* and *P. funiculosum* Cel7A enzymes expressed in *A. awamori* by measuring ellipticity at 230 nm using a Jasco Model J-715 spectropolarimeter.
Figure 15:
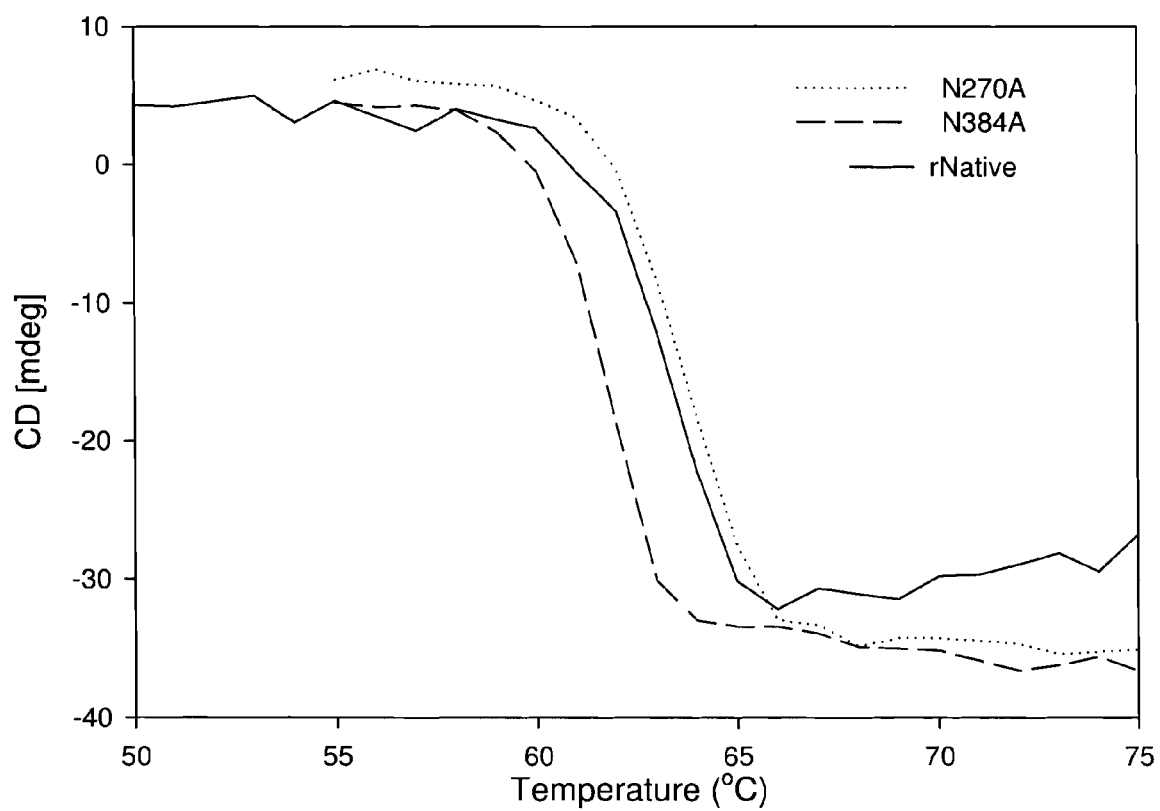
FIG. 15. Comparison of the thermal denaturation curves of recombinant *T. reesei* Cel7A enzymes expressed in *A. awamori* by measuring ellipticity at 230 nm using a Jasco Model J-715 spectropolarimeter.

Thermal denaturation of wild type and mutant Cel7A enzymes was evaluated using a single wavelength (230 nm). FIGS. 14 and 15 illustrate thermal scans conducted to compare the stability of the *T. reesei* and *P. funiculosum* enzymes and to also to compare the thermal unfolding of the *T. reesei* mutants N270A and N384A. The CD spectrum of the thermal denaturation curves of *A. awamori*-expressed wild type *T. reesei* and *P. funiculosum* Cel7A enzymes shown in FIG. 10 demonstrates that the *P. funiculosum* enzyme is 2 to 3 degrees more thermal stable than the *T. reesei* enzyme. Furthermore, the results shown in FIG. 11 illustrate a loss in thermal stability as a result of the N384A mutation in the *T. reesei* enzyme. Our evaluation of the changes in tertiary structure accomplished by monitoring changes in the near UV CD region suggests that the thermal unfolding of these proteins occurs in a single step with the concurrent loss of both secondary and tertiary structure.

The Role of N-Glycosylation on Cel7A Activity

Figure 16:
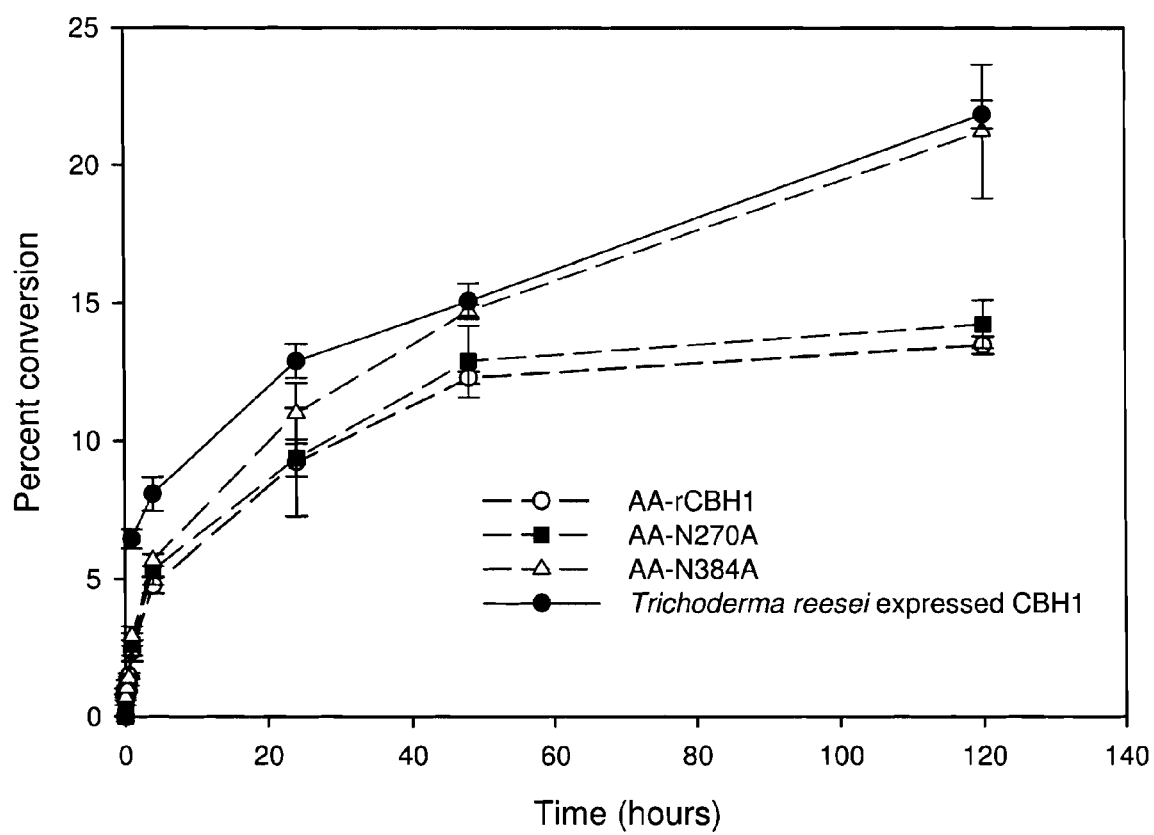
FIG. 16. Hydrolysis extent time course data for 1.0 µM *T. reesei* Cel7A wild type sequence, N270A, and N384A incubated with 1.0 mg/mL BC at 38° C.

The carbohydrate contents of wild type *T. reesei* and *A. awamori* expressed *T. reesei* Cel7A were estimated to be 0.84% (±0.17%) and 5.47% (±0.16%), respectively. Interestingly, the extent of glycosylation of the *A. awamori* expressed wild type Cel7A was found to be approximately 5.5 times greater than that of the wild type Cel7A. Two glycosylation mutants of *T. reesei* Cel7A, N270A and N384A, were also successfully expressed and produced in *A. awamori*. The digestion curves for these mutants acting on bacterial cellulose (BC) are illustrated by FIG. 16. The loss of the glycosylation site at position 270 led to the purification of an enzyme that showed slight improvements in activity over that of the wild type enzyme purified from *A. awamori* culture broth. A more profound effect on the hydrolysis of BC was observed when the glycosylation site at position 384 was eliminated. This mutant retained high activity on BC for a minimum of 73 hours after the activities of both the *A. awamori* expressed wild type and N270A mutant *T. reesei* Cel7A species reached a plateau.

Figure 17:
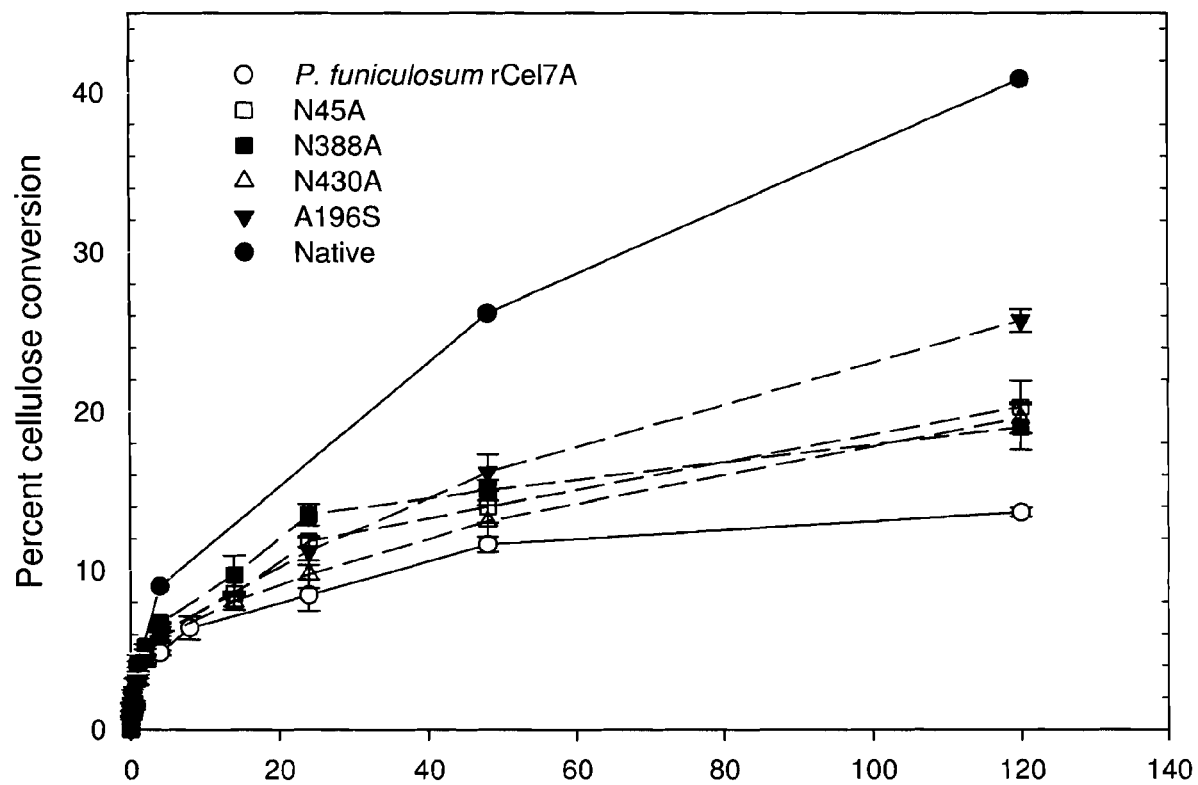
FIG. 17. Hydrolysis extent time course data for 1.0 µM *A. awamori* expressed *P. funiculosum* Cel7A (Wild type Sequence) and the four single mutants, N45A, N388A, N430A, and A196S incubated with 1.0 mg/mL BC at 38° C.
Figure 18:
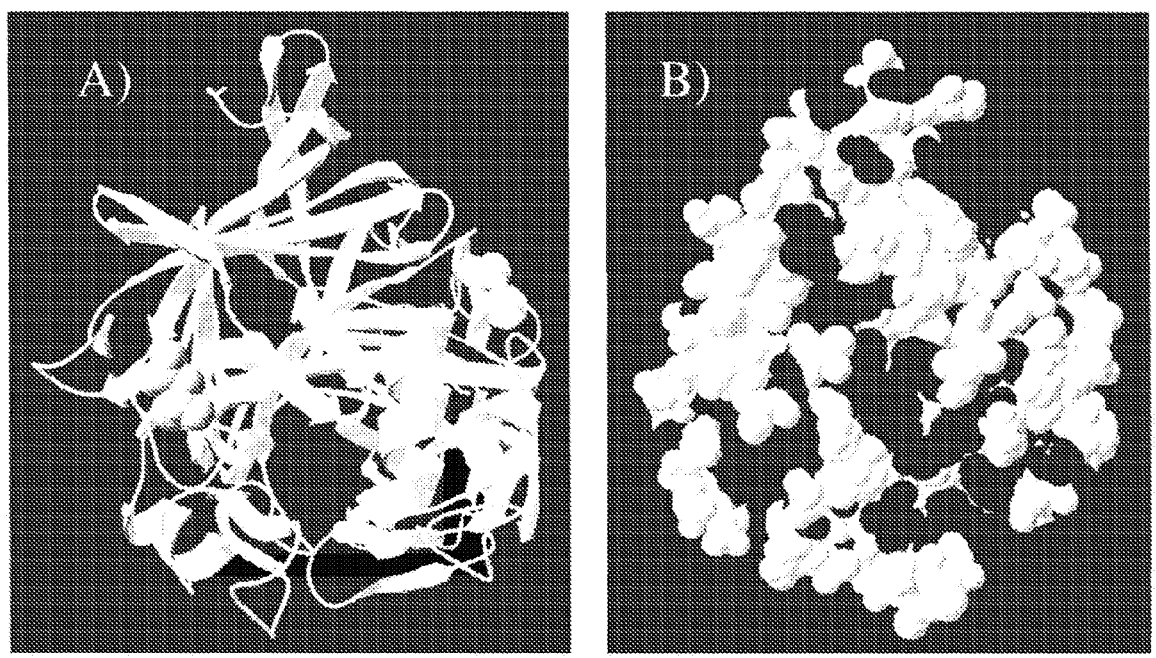
FIG. 18. N270 glycosylation site on *T. reesei* Cel7A. A) Rear view of the CD with N270 shown in gray on left of protein. B) Space-fill model showing polar amino acid residues in white, non-polar residues in gray, and N270 in black. This view is centered on the N270 residue, with the opening of the catalytic site tunnel to the right.
Figure 19:
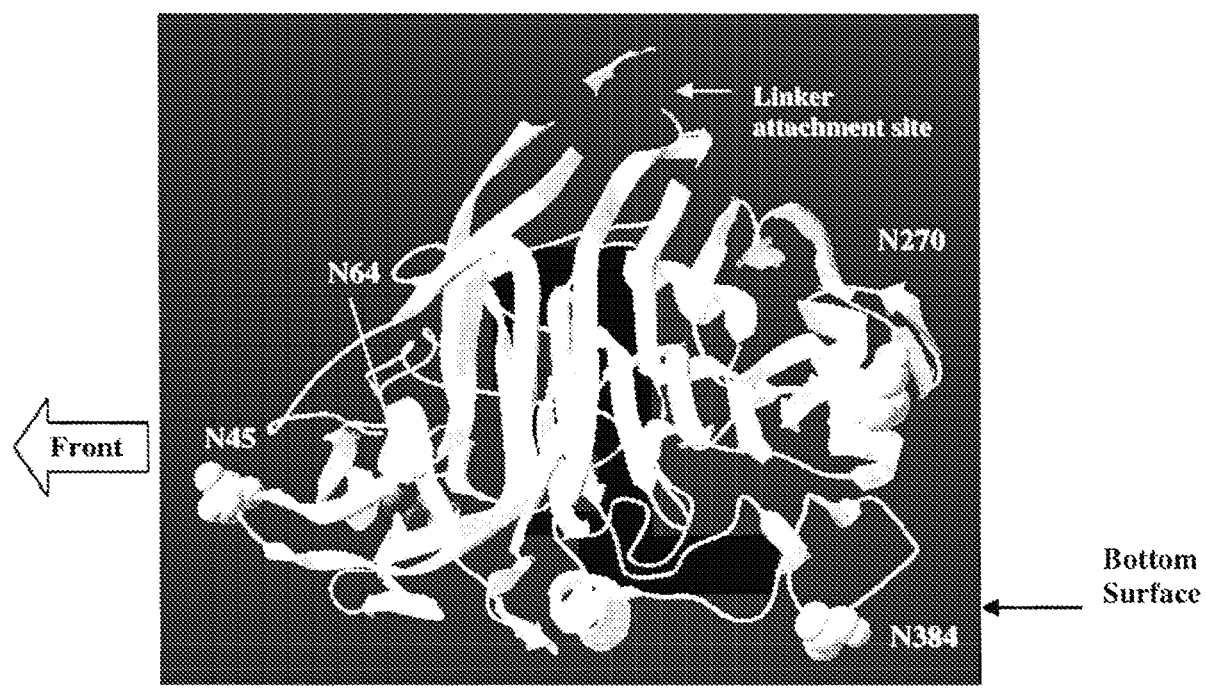
FIG. 19. Side view of a ribbon rendering of *T. reesei* Cel7A CD with an overall view of the location of glycosylation sites.

The BC activity of wild type and *A. awamori* expressed wild type *P. funiculosum* Cel7A was consistently higher than that of wild type *T. reesei* Cel7A. The low hydrolysis extents due to rapid drops in hydrolysis rates on BC indicate that both cellobiohydrolases were limited by the crystallinity of the substrate. Four single glycosylation mutants of the *P. funiculosum* enzyme (N45A, N388A, N430A, and A196S) were successfully expressed and purified from *A. awamori*. The digestion curves for these mutants acting on bacterial cellulose (BC) are illustrated by FIG. 17. Consistent with the previous observation for the case of the *T. reesei* Cel7A N384 glycan (analogous to N388 in *P. funiculosum* Cel7A), eliminating the glycan at N388 on *P. funiculosum* Cel7A resulted in significantly improved activity.

In addition to cataloguing the effect of each glycosylation site by systematic elimination of the sites, a new glycosylation site was added to *P. funiculosum* Cel7A at position N194. All mutations resulted in higher extents of BC hydrolysis. In each case, the mutants were able to maintain higher hydrolysis rates throughout the 120-hour period. The A196S mutant, with the additional glycosylation site at N194, sustained higher hydrolysis rates longer than any of the other mutants, as well as the wild type *P. funiculosum* Cel7A.

Example 8

Additional Cel7A Enzyme Glycosylation Mutants

The following example provides analysis of additional Cel7A enzymes with identification of N-linked glycosylation sites useful in producing glycosylation mutants.

The following Cel7A enzymes (TABLE 8) were compared to *T. reesei* Cel7A. Direct pair-wise amino acid comparison of these enzymes with the *T. reesei* enzyme demonstrates high amino acid homology and analogous N-linked glycosylation sites on the catalytic domain. N-linked glycosylation sites were targeted in the active site channel which are potentially sensitive to hyperglycosylation. These asparagine residues are replaced with amino acids such as glycine or alanine to generate an enzyme with decreased glycosylation. O-linked glycosylation sites are added to the respective linker domains of each enzyme.

TABLE 8

| Organism | Cel7A Protein Sequence* and SEQ ID NO |
| --- | --- |
| Trichodermaviride Accession # P19355 | MYQKLALISAFLATARAQSACTLQAETHPPLTWQKCSSGGTCTQQTGSVVIDANW RWTHATNSSTNCYDGNTWSSTLCPDNETCAKNCCLDGAAYASTYGVTTSADSLSI GFVTQSAQKINGARLYLMASDTTYQEFTLLGNEFSFDVDVSQLPCGLNGALYFVS MDADGGVSKYPTNTAGAKYGTGYCDSQCPRDLKFINGQANVEGWEPSSNNANTGI GGHGSCCSEMDIWEANSISEALTPHPCTTVGQEICDGDSCGGTYSGDRYGGTCDP DGCDWNPYRLGNTSFYGPGSSFTLDTTKKLTVVTQFETSGAINRYYVQNGVTFQQ PNAELGDYSGNSLDDDYCAAEEAEFGGSSFSDKGGLTQFKKATSGGMVLVMSLWD DYYANMLWLDSTYPTNETSSTPGAVRGSCSTSSGVPAQLESNSPNAKVVYSNIKF |

TABLE 8-continued

| Organism | Cel7A Protein Sequence* and SEQ ID NO |
|---|---|
| | GPIGSTGNSSGGNPPGGNPPGTTTTRRPATSTGSSPGPTQTHYGQCGGIGYSGFT<br>VCASGSTCQVLNPYYSQCL<br>SEQ ID NO: 100 |
| *Hypocrea lixii*<br>Accession #<br>Q9P8P3 | MYRKLAVISAFLAAARAQQVCTQQAETHPPLTWQKCTASGCTPQQGSVVLDANWR<br>WTHDTKSTTNCYDGNTWSSTLCPDDATCAKNCCLDGANYSGTYGVTTSGDALTLQ<br>FVTASNVGSRLYLMANDSTYQEFTLSGNEFSFDVDVSQLPCGLNGALYFVSMDAD<br>GGQSKYPGNAAGAKYGTGYCDSQCPRDLKFINGQANVEGWEPSSNNANTGVGGHG<br>SCCSEMDIWEANSISEALTPHPCETVGQTMCSGDSCGGTYSNDRYGGTCDPDGCD<br>WNPYRLGNTSFYGPGSSFALDTTKKLTVVTQFATDGSISRYYVQNGVKFQQPNAQ<br>VGSYSGNTINTDYCAAEQTAFGGTSFTDKGGLAQINKAFQGGMVLVMSLWDDYAV<br>NMLWLDSTYPTNATASTPGAKRGSCSTSSGVPAQVEAQSPNSKVIYSNIRFGPIG<br>STGGNTGSNPPGTSTTRAPPSSTGSSPTATQTHYGQCGGTGWTGPTRCASGYTCQ<br>VLNPFYSQC<br>SEQ ID NO: 101 |
| *Phanerochaete chrysosporium*<br>bg \|AAB46373.1\| | MFRTATLLAFTMAAMVFGQQVGTNTAENHRTLTSQKCTKSGGCSNLNTKIVLDAN<br>WRWLHSTSGYTNCYTGNQWDATLCPDGKTCAANCALDGADYTGTYGITASGSSLK<br>LQFVTGSNVGSRVYLMADDTHYQMFQLLNQEFTFDVDMSNLPCGLNGALYLSAMD<br>ADGGMAKYPTNKAGAKYGTGYCDSQCPRDIKFINGEANVEGWNATSANAGTGNYG<br>TCCTEMDIWEANNDAAAYTPHPCTTNAQTRCSGSDCTRDTGLCDADGCDFNSFRM<br>GDQTFLGKGLTVDTSKPFTVVTQFITNDGTSAGTLTEIRRLYVQNGKVIQNSSVK<br>IPGIDPVNSITDNFCSQQKTAFGDTNYFAQHGGLKQVGEALRTGMVLALSIWDDY<br>AANMLWLDSNYPTNKDPSTPGVARGTCATTSGVPAQIEAQSPNAYVVVFSNIKFGD<br>LNTTYTGTVSSSSVSSSHSSTSTSSSHSSSSTPPTQPTGVTVPQWGQCGGIGYTG<br>STTCASPYTCHVLNPYYSQCY<br>SEQ ID NO: 102 |
| *Volvarielle volvacea* | MRASLLAFSLNSAAGQQAGTLQTKNHPSLTSQKCRQGGCPQVNTTIVLDANWRWT<br>HSTSGSTNCYTGNTWQATLCPDGKTCAANCALDGADYTGTYGVTTSGNSLTLQFV<br>TQSNVGARLGYLMADDTTYQMFNLLNOEFWFDVDMSNLPCGLNGALYFSAMARTA<br>AWMPMVVCASTPLISTRRSTARLLRLPVPPRSRYGRGICDSQCPRDIKFINGEAN<br>VQGWQPSPNDTNAGTGNYGACCNKMDVWEANSISTAYTPHPCTQRGLVRCSGTAC<br>GGGSNRYGSICDHDGLGFQNLFGMGRTRVRARVGRVKQFNRSSRVVEPISWTKQT<br>TLHLGNLPWKSADCNVQNGRVIQNSKVNIPGMPSTMDSVTTEFCNAQKTAFNDTF<br>SFQQKGGMANMSEALRRGMVLVLSIWDDHAANMLWLDSITSAAACRSTPSEVHAT<br>PLRESQIRSSHSRQTRYVTFTNIKFGPFNSTGTTYTTGSVPTTSTSTGTTGSSTP<br>PQPTGVTVPQGQCGGIGYTGPTTCASPTTCHVLNPYYSQCY<br>SEQ ID NO: 103 |
| *Talaromyces emersonii* | MLRRALLLSSSAILAVKAQQAGTATAENHPPLTWQECTAPGSCTTQNGAVVLDAN<br>WRWVHDVNGYTNCYTGNTWDPTYCPDDETCAQNCALDGADYEGTYGVTSSGSSLK<br>LNFVTGSNVGSRLYLLQDDSTYQIFKLLNREFSFDVDVSNLPCGLNGALYFVAMD<br>ADGGVSKYPNNKAGAKYGTGYCDSQCPRDLKFIDGEANVEGWQPSSNNANTGIGD<br>HGSCCAEMDVWEANSISNAVTPHPCDTPGQTMCSGDDCGGTYSNDRYAGTCDPDG<br>CDFNPYRMGNTSFYGPGKIIDTTKPFTVVTQFLTDDGTDTGTLSEIKRFYIQNSN<br>VIPQPNSDISGVTGNSITTEFCTAQKQAFGDTDDFSQHGGLAKMGAAMQQGMVLV<br>MSLWDDYAAQMLWLDSDYPTDADPTTPGIARGTCPTDSGVPSDVESQSPNSYVTY<br>SNIKFGPINSTFT<br>SEQ ID NO: 104 |
| *Penicillium janthinellum* | MKGSISYQIYKGALLLSALLNSVSAQQVGTLTAETHPALTWSKCTAGXCSQVSGS<br>VVIDANWPXVHSTSGSTNCYTGNTWDATLCPDDVTCAANCAVDGARRQHLRVTTS<br>GNSLRINFVTTASQKNIGSRLYLLENDTTYQKFNLLNQEFTFDVDVSNLPCGLNG<br>ALYFVDMDADGGMAKYPTNKAGAKYGTGYCDSQCPRDLKFINGQANVDGWTPSKN<br>DVNSGIGNHGSCCAEMDIWEANSISNAVTPHPCDTPSQTMCTGQRCGGTYSTDRY<br>GGTCDPDGCDFNPYRMGVTNFYGPGETIDTKSPFTVVTQFLTNDGTSTGTLSEIK<br>RFYVQGGKVIGNPQSTIVGVSGNSITDSWCNAQKSAFGDTNEFSKMGGMAGMGAG<br>LADGMVLVMSLWDDHASDMLWLDSTYPTNATSTTPGAKRGTCDISRRPNTVESTY<br>PNAYVIYSNIKTGPLNSTFTGGTTSSSSTTTTTSKSTSTSSSSKTTTTVTTTTTS<br>SGSSGTGARDWAQCGGNGWTGPTTCVSPYTCTKQNDWYSQCL<br>SEQ ID NO: 105 |
| *Aspergillius nidulans*<br>FGSC A4 | MALLLSLSLLATTISAQQIGTPEIRPRLTTYHCTSANGCTEQNTSVVLDAATHPI<br>HDASNPSVSCTTSNGLNPALCDCADNCVIDGITDYAAHGVETHGSRLTLTQ<br>YRNVNGALSSVSPRVYLVDESDPDEQEYRALSLLAQEFTFTVNVSALPCGMNGAL<br>YLSEMSPSGGRSALNPAGASYGTGYCDAQCYVNPWINGEGNINGYGACCNEMDIW<br>EANSRSTGFTPHACLYEPEETEGRGVYECASEDECDSAGENDGICDKWGCGFNPY<br>ALGNTEYYGRGQGFEVDTKEPFTVVTQFLTDDGTSTGALTEIRRLYIQNGQVIEN<br>AVVSSGADSLTDSLCASTASWFDSYGGMEGMGRALGRGNVLAMSIWNDAGGYMQW<br>LDGGDAGPCNATEGAPEPIEEHTPWTRVVFEDLKWGDIGSTFQAS<br>SEQ ID NO: 106 |
| *Penicillium funiculosum* | MSALNSFNMYKSALILGSLLATAGAQQIGTYTAETHPSLSWSTCKSGGSCTTNSG<br>AITLDANWRWVHGVNTSTNCYTGNTWNTAICDTDASCAQDCALDGADYSGTYGIT<br>TSGNSLRLNFVTGSNVGSRTYLMADNTHYQIFDLLNQEFTFTVDVSNLPCGLNGA<br>LYFVTMDADGGVSKYPNNKAGAQYGVGYCDSQCPRDLKFIAGQANVEGWTPSTNN<br>SNTGIGNHGSCCAELDIWEANSISEALTPHPCDTPGLTVCTADDCGGTYSSNRYA |

TABLE 8-continued

| Organism | Cel7A Protein Sequence* and SEQ ID NO |
|---|---|
| | GTCDPDGCDFNPYRLGVTDFYGSGKTVDTTKPFTVVTQFVTDDGTSSGSLSEIRR<br>YYVQNGVVIPQPSSKISGISGNVINSDFCAAELSAFGETASFTNHGGLKNMGSAL<br>EAGMVLVMSLWDDYSVNMLWLDSTYPANETGTPGAARGSCPTTSGNPKTVESQSG<br>SSYVVFSDIKVGPFNSTFSGGTSTGGSTTTTASGTTSTKASTTSTSSTSTGTGVA<br>AHWGQCGGQGWTGPTTCASGTTCTVVNPYYSQCL<br>SEQ ID NO: 107 |
| Thielavia australiensis | MYAKFATLAALVAGASAQAVCSLTAETHPSLTWQKCTAPGSCTNVAGSITIDANW<br>RWTHQTSSATNCYSGSKWDSSICVTGTDCASKCCIDGAEYSSTYGITTSGNALNL<br>KFVTKGQYSTNIGSRTYLMESDTKYQMFKLLGNEFTFDVDVSNLGCGLNGALYFV<br>SMDADGGMSKYSGNKAGAKYGTGYCDAQCPRDLKFINGEANVEGWESSTNDANAG<br>SGKYGSCCTEMDVWEANNMATAFTPHPCTTIGQTRCEGDTCGGTYSSDRYAGVCD<br>PDGCDFNSYRQGNKTFYGKGMTVDTTKKITVVTQFLKNSAGELSEIKRFYAQDGK<br>VIPNSESTIAGIPGNSITKAYCDAQKTVFQNTDDFTAKGGLVQMGKALAGDMVLV<br>MSVWDDHAVNMLWLDSTYPTDQVGVAGAERGACPTTSGVPSDVEANAPNSNVIFS<br>NIRFGPIGSTVQGLPSSGGTSSSSSAAPQSTSTKASTTTSAVRTTSTATTKTTSS<br>APAQGTNTAKHWQQCGGNGWTGPTVCESPYKCTKQNDWYSQCL<br>SEQ ID NO: 108 |
| Chrysosporium lucknowense | MYAKFATLAALVAGAAAQNACTLTAENHPSLTWSKCTSGGSCTSVQGSITIDANW<br>RWTHRTDSATNCYEGNKWDTSYCSDGPSCASKCCIDGADYSSTYGITTSGNSLNL<br>KFVTKGQYSTNIGSRTYLMESDTKYOMFQLLGNEFTFDVDVSNLGCGLNGALYFV<br>SMDADGGMSKYSGNKAGAKYGTGYCDSQCPRDLKFINGEANVENWQSSTNDANAG<br>TGKYGSCCSEMDVWEANNMAAAFTPHPCXVIGOSRCEGDSCGGTYSTDRYAGICD<br>PDGCDFNSYRQGNKTFYGKGMTVDTTKKITVVTQFLKNSAGELSEIKRFYVQNGK<br>VIPNSESTIPGVEGNSITQDWCDRQKAAFGDVTDXQDKGGMVQMGKALAGPMVLV<br>MSIWDDHAVNMLWLDSTWPIDGAGKPGARRGACPTTSGVPAEVEAEAPNSNVIFS<br>NIRFGPIGSTVSGLPDGGSGNPNPPVSSSTPVPSSSTTSSGSSGPTGGTGVAKHY<br>EQCGGIGFTGPTQCESPYTCTKLNDWYSQCL<br>SEQ ID NO: 109 |

*N-linked glycosylation sites are in shown in bold

Mutants with targeted amino acid substitutions are generated as described above and confirmed by DNA sequencing.

BIBLIOGRAPHY

The following references are specifically incorporated herein by reference.

Anumula, K. R., High sensitivity and high resolution methods for glycoprotein analysis. Glycobiology 2000, 10, (10), 1138-1138.

Armand, S.; Drouillard, S.; Schulein, M.; Henrissat, B.; Driguez, H., A bifunctionalized fluorogenic tetrasaccharide as a substrate to study cellulases (vol 272, pg 2709, 1997). Journal of Biological Chemistry 1997, 272, (11), 7565-7565.

Boer, H.; Koivula, A., The relationship between thermal stability and pH optimum studied with wild-type and mutant Trichoderma reesei cellobiohydrolase Cel7A. European Journal of Biochemistry 2003, 270, (5), 841-848.

Bo Xu, Y., and Qing, S. Y. J. Protein Chem. 1997 16, 107-111.

Breyer, W. A.; Matthews, B. W., A structural basis for processivity. Protein Science 2001, 10, (9), 1699-1711.

Cartee, R. T.; Forsee, W. T.; Yotlier, J. L.; Schutzbach, J. S., The type 3 synthase from Streptococcus pneumoniae is a processive enzyme that synthesizes type 3 polysaccharide from the non-reducing end. Glycobiology 1998, 8, (II), 1123-1123.

Chen, C. M.; Ward, M.; Wilson, L.; Sumner, L.; Shoemaker, S., Toward Improved Cellulases—Targeted Modifications of Trichoderma-Reesei Exocellobiohydrolase-Ii Using Site Specific Mutagenesis. Abstracts of Papers of the American Chemical Society 1987, 194, 188-MBTD.

Chen, H M; Li, Y X; Panda, T; Buehler, F; Ford, C; Reilly, P J. Effect of replacing helical glycine residues with alanines on reversible and irreversible stability and production of Aspergillus awamori glucoamylase. Protein Eng. 1996, v9 i6 p 499-505.

Chen, H. Z.; Hayn, M.; Esterbauer, H., 3 Forms of Cellobiohydrolase-I from Trichoderma-Reesei. Biochemistry and Molecular Biology International 1993, 30, (5), 901-910.

Chou, K. C; Kezdy, F. J.; Reusser, F., Kinetics of Processive Nucleic-Acid Polymerases and Nucleases. Analytical Biochemistry 1994, 221, (2), 217-230.

Cui, Y Q; Okkerse, W J; vanderLans, R G J M; Luyben, K C A M. Modeling and measurements of fungal growth and morphology in submerged fermentations. Biotechnol. Bioeng. Oct. 20, 1998, v60 i2 p 216-229 (14).

Cui, Y Q; Ouwehand, J N W; vanderLans, R G J M; Giuseppin, M L F; Luyben, K C A M. Aspects of the use of complex media for submerged fermentation of Aspergillus awamori. Enzyme Microbial Technol. July-August 1998, v23 μ 1-2 p 168-177 (10).

Cui, Y Q; van der Lans, R G J M; Luyben, K C A M. Effect of agitation intensities on fungal morphology of submerged fermentation. Biotech. Bioeng. Sep. 5, 1997, v55 i5 p 715-726 (12).

Cui, Y Q; van der Lans, R G J M; Luyben, K C A M. Effects of dissolved oxygen tension and mechanical forces on fungal morphology in submerged fermentation. Biotech. Bioeng. Feb. 20, 1998, v57 i4 p 409-419 (11).

Cui, Y Q; vander Lans, R G J M; Giuseppin, M L F; Luyben, K C A M. Influence of fermentation conditions and scale on the submerged fermentation of Aspergillus awamori. Enzyme Microb. Technol. July-August 1998, v23 i1-2 p 157-167 (11).

Decker, S. R.; Adney, W. S.; Jennings, E.; Vinzant, T. B.; Himmel, M. E., Automated filter paper assay for determination of cellulase activity. Applied Biochemistry and Biotechnology 2003, 105, 689-703.

deGroot, M J A; Bundock, P; Hooykaas, P J J; Beijersbergen, A G M. Agrobacterium tumefaciens-mediated transformation of filamentous fungi. Nature Biotechnol. September 1998, v16 i9 p 839-842 (4).

Dell, A.; Morris, H. R., Glycoprotein Structure Determination by Mass Spectrometry. Science 2001, 291, (5512), 2351-2356.

Elshafei, A. M.; Vega, J. L.; Klasson, K. T.; Clausen, E. C; Gaddy, J. L., The saccharification of corn stover by cellulase from *Penicillium funiculosum*. Bioresource technology 1991, 35, (1), 73-80.

Eriksen, S. H.; Jensen, B.; Olsen, J., Effect of N-linked glycosylation on secretion, activity, and stability of alpha-amylase from *Aspergillus oryzae*. Current Microbiology 1998, 37, (2), 117-122.

Eriksson, T.; Stals, I.; Colien, A.; Tjerneld, F.; Claeyssens, M.; Stalbrand, H.; Brumer, H., Heterogeneity of homologously expressed *Hypocrea jecorina* (*Trichoderma reesei*) Cel7B catalytic module. European Journal of Biochemistry 2004, 271, (7), 1266-1276.

Fagertein et. al. FEBS. 1984, 1265, 167 (2): 389-315.

Fang, T Y; Ford, C. Protein engineering of *Aspergillus awamori* glucoamylase to increase its pH optimum. Protein Eng. May 1998, v11 i5 p 383-388 (6).

Foreman, P. K.; Brown, D.; Dankmeyer, L.; Dean, R.; Diener, S.; Dunn-Coleman, N. S.; Goedegebuur, F.; Houfek, T. D.; England, G. J.; Kelley, A. S.; Meerman, H. J.; Mitchell, T.; Mitchinson, C; Olivares, H. A.; Teunissen, P. J. M.; Yao, J.; Ward, M., Transcriptional regulation of biomass-degrading enzymes in the filamentous fungus *Trichoderma reesei*. Journal of Biological Chemistry 2003, 278, (34), 31988-31997.

Gaur, R.; Mishra, S.; Dubey, R. C, Cellulase activity at different sites in two fungal species, *Trichoderma harzianum* and *Penicillium funiculosum*. Acta botanica Indica 1990, 18, (1), 141-143.

Goto, M; Ekino, K; Furukawa, K. Expression and functional analysis of a hyperglycosylated glucoamylase in a parental host, *Aspergillus awamori* var. kawachi. Appl. Environ. Microbiol. July 1997, v63 i7 p 2940-2943 (4).

Gouka, R J; Hessing, J G M; Punt, P J; Stam, H; Musters, W; van den Hondel, C A M J J. An expression system based on the promoter region of the *Aspergillus awamori* 1,4-beta-endoxylanase A gene. Appl. Microbiol. Biotechnol. 1996 v46 i1 p 28-35 (8).

Gouka, R J; Punt, P J; Hessing, J G M; van den Hondel, C A M J J. Analysis of heterologous protein production in defined recombinant *Aspergillus awamori* strains. Appl. Environ. Microbiol. 1996, v62 i6 p 1951-1957 (7).

Gouka, R J; Punt, P J; van den Hondel, C A M J J. Glucoamylase gene fusions alleviate limitations for protein production in *Aspergillus awamori* at the transcriptional and (post)translational levels. Appl. Environ. Microbiol. February 1997, v63 i2 p 488497 (10).

Gouka, R J; Stam, H; Fellinger, A J; Muijsenberg, R J G T; van de Wijngaard, A J; Punt, P J; Musters, W; van den Hondel, C A M J J. Kinetics of mRNA and protein synthesis of genes controlled by the 1,4-beta-endoxylanase A promoter in controlled fermentations of *Aspergillus awamori*. Appl. Environ. Microbiol. October 1996, v62 i10 p 3646-3649 (4).

Haltiwanger, R. S.; Lowe, J. B., Role of glycosylation indevelopment. Annual Review of Biochemistry 2004, 73, 491-537.

Helbert, W.; Chanzy, H.; Husum, T. L.; Schulein, M.; Ernst, S., Fluorescent cellulose microfibrils as substrate for the detection of cellulase activity. Biomacromolecules 2003, 4, (3), 481-487.

Hellendoorn, L; Mulder, H; van den Heuvel, J C; Ottengraf, S P P. Intrinsic kinetic parameters of the pellet forming fungus *Aspergillus awamori*. Biotechnol. Bioeng. Jun. 5, 1998, v58 i5 p 478-485 (8).

Henrissat, B.; Davies, G., Structural and sequence-based classification of glycoside hydrolases. Current Opinion in Structural Biology 1997, 7, (5), 637-644.

Hestrin S, S. M., Synthesis of Cellulose by *Acelobacter xylinum*. Biochemical Journal 1954, 58, 345-352.

Hijarrubia, M J; Casqueiro, J; Gutierrez, S; Fernandez, F J; Martin, J F. Characterization of the bip gene of *Aspergillus awamori* encoding a protein with an HDEL retention signal homologous to the mammalian BiP involved in polypeptide secretion. Current Genetics. August 1997, v32 i2 p 139-146(8).

Himmel, M. E.; Ruth, M. F.; Wyman, C. E., Cellulase for commodity products from cellulosic biomass. Current Opinion in Biotechnology 1999, 10, (4), 358-364.

Hui, J. P. M.; Lanthier, P.; White, T. C; McHugh, S. G.; Yaguchi, M.; Roy, R.; Thibault, P., Characterization of cellobiohydrolase I (Cel7A) glycoforms from extracts of *Trichoderma reesei* using capillary isoelectric focusing and electrospray mass spectrometry. Journal of Chromatography B-Analytical Technologies in the Biomedical and Life Sciences 2001, 752, (2), 349-368.

IonSource.com N- and O-linked Protein Glycosylation. Retrieved from the internet on Apr. 21, 2008: <URL: http://www.ionsource.com/Card/carbo/nolink.htm>

Jacobson, R. H., Matsumura, M., Faber, H. R. & Matthews, B. W. Structure of a stabilizing disulfide bridge mutant that closes the active-site cleft of T4 lysozyme. Protein Science 1992, 1, 46-57.

Johansen, C L; Coolen, L; Hunik, J H. Influence of morphology on product formation in *Aspergillus awamori* during submerged fermentations. Biotechnol. Progress. March-April 1998, v14 i2 p 233-240 (8).

Krystynowicz A, C. W., Wiktorowska-Jezierska A, Goncalves-Miskiewicz M, Turkiewicz M, Bielecki S., Factors affecting the yield and properties of bacterial cellulose. Journal of Industrial Microbiology & Biotechnology 2002, 29, (4), 189-195.

Lachke, A. H.; Srinivasan, M. C; Deshmukh, S. S.; Deshpancle, M. V., Strain selection criteria for *Penicillium funiculosum* in enzymic hydrolysis of lignocellulosics. Biotechnology letters 1987, 9, (2), 147-150.

Lassig, F., Schultz, M. D., Gooch, M., Evans, B. R., and Woodward, J. Arch. Biochem. Biophys. 1995, 322, 119-126.

Laymon, R. A.; Adney, W. S.; Mohagheghi, A.; Himmel, M. E.; Thomas, S. R., Cloning and expression of full-length *Trichoderma reesei* cellobiohydrolase I cDNAs in *Escherichia coli*. Applied Biochemistry and Biotechnology 1996, 57-8, 389-397.

Li, Y X; Coutinho, P M; Ford, C. Effect on thermostability and catalytic activity of introducing disulfide bonds into *Aspergillus awamori* glucoamylase. Protein Eng. August 1998, v11 i8 p 661-667 (7).

Li, Y X; Reilly, P J; Ford, C. Effect of introducing proline residues on the stability of *Aspergillus awamori*. Protein Eng. October 1997, v10 i10 p 1199-1204 (6).

Manchanda, A. C; Jogdand, V. V.; Karanth, N. G., Studies on fermentation-broth rheology of a *Penicillium* strain with cellulose as substrate Enzymic conversion of cellulosic wastes into alcohol, *Penicillium funiculosum*. Journal of chemical technology and biotechnology 1982, 32, (6), 660-665.

Maras, M., De Bruyn, A., Schraml, J., Herdewijn, P., Claeyssens, M., Fiers, W., and Contreras, R., Circular Dichroism of Proteins, Eur. J., Biochem., 1997, 245, 617-625

McAuley, K. E.; Svendsen, A.; Petkar, S. A.; Wilson, K. S., Structure of a feruloyl esterase from *Aspergillus niger*. Acta Crystallographica Section D-Biological Crystallography 2004, 60, 878-887.

Medve, J.; Lee, D.; Tjerneld, F., Ion-exchange chromatographic purification and quantitative analysis of *Trichoderma reesei* cellulases cellobiohydrolase, I, II and endoglucanase II by fast protein liquid chromatography. Journal of chromatography. A. 1998, 808, (1/2).

Medve, J.; Stahlberg, J.; Tjerneld, F., Adsorption and synergism of cellobiohydrolase I and II of *Trichoderma reesei* during hydrolysis of microcrystalline cellulose. Biotechnology and bioengineering. 1994, 44, (9]).

Motoshima, H. et al. Analysis of the stabilization of hen lysozyme by helix macrodipole and charged side chain interaction. J. Biochem. (Tokyo) 1997 121, 1076-1081.

Nascimento, H J; Soares, V F; Bon, E P S; Silva, J G. Extracellular proteolytic processing of *Aspergillus awamori* GAI into GAII is supported by physico-chemical evidence. Appl. Biochem. Biotechnol. Spring 1998, v70-2 p 641-650 (10).

Nicholson, H., Anderson, D. E., Dao-pin, S. & Matthews, B. W. Analysis of the interaction between charged side chains and the alpha-helix dipole using designed thermostable mutants of phage T4 lysozyme. Biochemistry 1991, 30, 9816-9828.

Okada, H., Sekiya, T., Yokoyama, K., Tohda, H., Kumagai, H., and Morikawa, Y., Appl. Microbiol. Biotechnol., 1998, 49, 301-308.

Penttila, M. E., Andre, L., Lehtovaara, P., Bailey, M., Teeri, T. T., Knowles, J. K. C. Gene 1988, 63, 103-112.

Pjura, P. E., Matsumura, M., Wozniak, J. A. & Matthews, B. W. Structure of a thermostable disulfide-bridge mutant of phage T4 lysozyme shows that an engineered cross-link in a flexible region does not increase the rigidity of the folded protein. Biochemistry 1990, 29, 2592-2598.

Presta, L. G. & Rose, G. D. Helix signals in proteins. Science 1988, 240, 1632-1641.

Receveur, W.; Czjzek, M.; Schulein, M.; Panine, P.; Henrissat, B., Dimension, shape, and conformational flexibility of a two domain fungal cellulase in solution probed by small angle X-ray scattering. Journal of Biological Chemistry. 2002, 277, (43), 40887-40892.

Reinikainen, T., Rouhonen, L., Nevanen, T., Laaksonen, L., Kraulis, P., Jones, T. A., Knowles, J., and Teeri. T. Proteins, Structure Function Genetics 1992, 14, 475-482.

Reverbel Leroy, C; Pages, S.; Belaich, A.; Belaich, J. P.; Tardif, C, The processive endocellulase CelF, a major component of the *Clostridium cellulolyticum* cellulosome: Purification and characterization of the recombinant form. Journal of Bacteriology 1997, 179, (1), 46-52.

Richardson, J. S. & Richardson, D. C. Amino acid preferences for specific locations at the ends of alpha helices [published erratum appears in Science Dec. 23, 1988; 242 (4886): 1624]. Science 1988, 240, 1648-1652.

Rowan, A. E.; Thordarson, P.; Coumans, R. G. E.; Bijsterveld, E.; Nolte, R. J. M., Catalytic macromolecular rotaxanes: Towards mimicking nature's processive catalysts. Abstracts of Papers of the American Chemical Society 2003, 225, U637-U638.

Russell, R. J. M., Hough, D. W., Danson, M. J. & Taylor, G. L. The crystal structure of citrate synthase from the thermophilic Archaeon, *Thermoplasma acidophilum*. Structure 1994, 2, 1157-1167.

Sahasrabudhe, N. A.; Ranjekar, P. K., Cloning of the Cellulase Gene from *Penicillium-Funiculosum* and Its Expression in *Escherichia-Coli*. Ferns Microbiology Letters 1990, 66, (1-3), 291-293.

Sakon, J., Adney, W. S., Himmel, M. E., Thomas, S. R. & Karplus, P. A. Crystal structure of thermostable family 5 endocellulase E1 from *Acidothermus cellulolyticus* in complex with cellotetraose. Biochemistry 1996, 35, 10648-10660.

Shoemaker, S. P., 1996 In "The cellulase system of *Trichoderma reesei: Trichoderma* strain improvement and expression of *Trichoderma cellulases* in yeast" pp 593-600.

Siedenberg, D; Gerlach, S R; Schugerl, K; Giuseppin, M L F; Hunik, J. Production of xylanase by *Aspergillus awamori* on synthetic medium in shake flask cultures. Process Biochem. March 1998, v33 i4 p 429433 (5).

Sreerama, N.; Venyaminov, S. Y.; Woody, R. W., Estimation of protein secondary structure from circular dichroism spectra: Inclusion of denatured proteins with native proteins in the analysis. Analytical Biochemistry 2000, 287, (2), 243-251.

Stites, W. E., Meeker, A. K. & Shortle, D. Evidence for strained interactions between side-chains and the polypeptide backbone. J. Mol. Biol. 1994, 235, 27-32.

Taylor, M. E.; Drickamer, K., Introduction to Glycobiology. 2003, Oxford University Press, Inc.: New York.

Teeri, T. T., 1987, Doctoral Thesis, VTT Publications No. 38.

Van Arsdell, J. N., Kwok, S., Schweickart, V. L., Gelfand, D. H., and Innis, M. a. Bio/Technology 1987, 5, 60-64.

Van Gemeren, I A; Beijersbergen, A; Musters, W; Gouka, R J; van den Hondel, C A M J J; Verrips, C T. The effect of pre- and pro-sequences and multicopy integration on heterologous expression of the *Fusarium solani* pisi cutinase gene in *Aspergillus awamori*. Appl. Microbiol. Biotechnol. 1996, v45 i6 p 755-763 (9).

Van Gemeren, I A; Punt, P J; Drint Kuyvenhoven, A; Broekhuijsen, M P; vant Hoog, A; Beijersbergen, A; Verrips, C T; van den Hondel, C A M J J. The ER chaperone encoding bipA gene of black *Aspergilli* is induced by heat shock and unfolded proteins. Gene. Oct. 1, 1997, v198 μ 1-2 p 43-52 (10).

Van Pouderoyen, G.; Snijder, H. J.; Benen, J. A. E.; Dijkstra, B. W., Structural insights into the processivity of endopolygalacturonase I from *Aspergillus niger*. Febs Letters 2003, 554, (3), 462-466.

Van Gemeren, I A; Beijersbergen, A; van den Hondel, CAMJJ; Verrips, C T. Expression and secretion of defined cutinase variants by *Aspergillus awamori*. Appl. Environ. Microbiol. August 1998, v64 i8 p 2794-2799 (6).

Vanrot, A.; Schulein, M.; Davies, G. J., Structural changes of the active site tunnel of *Humicola insolens* cellobiohydrolase, Cel6A, upon oligosaccharide binding. Biochemistry 1999, 38, (28), 8884-8891.

Von Ossowski, I., Teeri, T., Kalkkinen, N., and Oker-Blom, C., Biochem. Biophysical Comm., 1997, 233, 25-29.

Von Ossowski, I.; Stahlberg, J.; Koivula, A.; Piens, K.; Becker, D.; Boer, H.; Harle, R.; Harris, M.; Divne, C; Mahdi, S.; Zhao, Y. X.; Driguez, H.; Claeyssens, M.; Sinnott, M. L.; Teeri, T. T., Engineering the exo-loop of *Trichoderma reesei* cellobiohydrolase, Cel7A. A comparison with *Phanerochaete chrysosporium* Cel7D. Journal of Molecular Biology 2003, 333, (4), 817-829.

Zurbriggen, B., Bailey, M. J., Penttila, M. E., Poutanen, K., and Linko, M. J. Biotechnol. 1990, 13, 267-278.

A number of patents, patent application publications, and scientific publications are cited throughout and/or listed at the end of the description. Each of these is incorporated herein by reference in its entirety. Likewise, all publications mentioned in an incorporated publication are incorporated by reference in their entirety.

Examples in cited publications and limitations related therewith are intended to be illustrative and not exclusive. Other limitations of the cited publications will become apparent to those of skill in the art upon a reading of the specification and a study of the drawings.

The words "comprise", "comprises", and "comprising" are to be interpreted inclusively rather than exclusively.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope. For example, the disclosure encompasses all possible permutations of the claims, as if they were multiple dependent claims.

What is claimed is:

1. An isolated *Penicillium funiculosum* cellobiohydrolase I (Cel7A) polypeptide comprising a mutation at position 196 of SEQ ID NO:110 that creates a new N-linked glycosylation site at the asparagine residue at position 194 of SEQ ID NO:110, wherein the mutation results in a mutant polypeptide with improved cellulase activity relative to the wild type Cel7A polypeptide, and wherein the wild type Cel7A polypeptide has the amino acid sequence of SEQ ID NO:110.

2. The isolated polypeptide of claim 1, wherein the polypeptide is produced by expressing the mutated polypeptide in a heterologous host cell.

3. The isolated polypeptide of claim 1, further comprising the substitution of one or more amino acid residues in the linker domain with a serine or threonine residue or the addition of one or more serine or threonine residues to the linker domain, wherein the one or more substitutions or additions results in increased O-linked glycosylation of the linker domain relative to the linker domain of the wild type Cel7A polypeptide without the one or more substitutions or additions.

4. A composition comprising the isolated cellobiohydrolase I (Cel7A) polypeptide of claim 1.

5. The composition of claim 4, wherein the polypeptide is produced by expressing the mutated polypeptide in a heterologous host cell.

6. A method of making an active *Penicillium funiculosum* cellobiohydrolase I (Cel7A) polypeptide, comprising modifying a wild type *Penicillium funiculosum* Cel7A polypeptide to increase cellulase activity of the wild type Cel7A polypeptide, wherein the modification comprises introducing a mutation at position 196 of SEQ ID NO:110 to create a new N-linked glycosylation site at the asparagine residue at position 194 of SEQ ID NO:110, and wherein the wild type Cel7A polypeptide has the amino acid sequence of SEQ ID NO:110.

7. The method of claim 6, wherein the modification is achieved using site-directed mutagenesis.

8. The method of claim 6, wherein the Cel7A polypeptide is further modified by the substitution of one or more amino acid residues in the linker domain with a serine or threonine residue or the addition of one or more serine or threonine residues to the linker domain, wherein the one or more substitutions or additions results in increased O-linked glycosylation of the linker domain relative to the linker domain of the wild type Cel7A polypeptide without the one or more substitutions or additions.

9. The method of claim 6, wherein the mutation is a substitution of the alanine residue at position 196 of SEQ ID NO:110 with a threonine residue.

10. The method of claim 6, wherein the mutation is a substitution of the alanine residue at position 196 of SEQ ID NO:110 with a serine residue.

11. The method of claim 10, wherein the Cel7A polypeptide is further modified by the substitution of one or more amino acid residues in the linker domain with a serine or threonine residue or the addition of one or more serine or threonine residues to the linker domain, wherein the one or more substitutions or additions results in increased O-linked glycosylation of the linker domain relative to the linker domain of the wild type Cel7A polypeptide without the one or more substitutions or additions.

12. The isolated polypeptide of claim 1, wherein the mutation is a substitution of the alanine residue at position 196 of SEQ ID NO: 110 with a threonine residue.

13. The isolated polypeptide of claim 1, wherein the mutation is a substitution of the alanine residue at position 196 of SEQ ID NO: 110 with a serine residue.

14. The isolated polypeptide of claim 13, further comprising the substitution of one or more amino acid residues in the linker domain with a serine or threonine residue or the addition of one or more serine or threonine residues to the linker domain, wherein the one or more substitutions or additions results in increased O-linked glycosylation of the linker domain relative to the linker domain of the wild type Cel7A polypeptide without the one or more substitutions or additions.

15. The method of claim 9, wherein the Cel7A polypeptide is further modified by the substitution of one or more amino acid residues in the linker domain with a serine or threonine residue or the addition of one or more serine or threonine residues to the linker domain, wherein the one or more substitutions or additions results in increased O-linked glycosylation of the linker domain relative to the linker domain of the wild type Cel7A polypeptide without the one or more substitutions or additions.

16. The isolated polypeptide of claim 12, further comprising the substitution of one or more amino acid residues in the linker domain with a serine or threonine residue or the addition of one or more serine or threonine residues to the linker domain, wherein the one or more substitutions or additions results in increased O-linked glycosylation of the linker domain relative to the linker domain of the wild type Cel7A polypeptide without the one or more substitutions or additions.

\* \* \* \* \*